(12) United States Patent
Hong et al.

(10) Patent No.: US 8,298,814 B1
(45) Date of Patent: Oct. 30, 2012

(54) DEGRADATION OF POLYCYCLIC AROMATIC HYDROCARBONS

(75) Inventors: P. K. Andy Hong, Salt Lake City, UT (US); David A. Wavrek, Salt Lake City, UT (US); Jiun-Chi Chao, Salt Lake City, UT (US); Yu Zeng, San Diego, CA (US)

(73) Assignees: David A. Wavrek, Salt Lake City, UT (US); University of Utah, Salt Lake City, UT (US)

( * ) Notice: Subject to any disclaimer, the term of this patent is extended or adjusted under 35 U.S.C. 154(b) by 1578 days.

(21) Appl. No.: 10/129,354

(22) PCT Filed: Nov. 6, 2000

(86) PCT No.: PCT/US00/30599
§ 371 (c)(1),
(2), (4) Date: Sep. 9, 2005

(87) PCT Pub. No.: WO01/32936
PCT Pub. Date: May 10, 2001

Related U.S. Application Data

(60) Provisional application No. 60/164,070, filed on Nov. 5, 1999, provisional application No. 60/164,071, filed on Nov. 5, 1999.

(51) Int. Cl.
*A62D 3/00* (2007.01)
*A62D 3/02* (2007.01)
*B09B 3/00* (2006.01)
*B09C 1/10* (2006.01)
*C02F 1/02* (2006.01)
*C02F 3/00* (2006.01)
*C02F 3/34* (2006.01)
*C10G 32/00* (2006.01)

(52) U.S. Cl. .............. 435/262; 435/262.5; 435/281; 435/809; 210/600; 210/601; 210/634

(58) Field of Classification Search ............. None
See application file for complete search history.

(56) References Cited

U.S. PATENT DOCUMENTS

| 4,329,254 A * | 5/1982 | Chmielowiec .............. 502/401 |
| 4,401,570 A * | 8/1983 | Blytas et al. ............... 210/639 |
| 4,405,448 A * | 9/1983 | Googin et al. ........... 208/262.5 |
| 5,254,255 A * | 10/1993 | Kalema et al. ............. 210/634 |
| 5,476,975 A * | 12/1995 | Ruddick et al. ............ 568/762 |
| 5,560,737 A * | 10/1996 | Schuring et al. ........ 405/128.45 |
| 5,656,246 A * | 8/1997 | Patapoff et al. ............ 422/187 |
| 5,849,201 A * | 12/1998 | Bradley ..................... 210/752 |
| 6,403,034 B1 * | 6/2002 | Nelson et al. ................ 422/32 |
| 7,124,030 B2 | 10/2006 | Ellis |
| 2006/0027505 A1 | 2/2006 | Hayes et al. |
| 2006/0163117 A1 | 7/2006 | Hong |
| 2009/0159536 A1 | 6/2009 | Hong |

FOREIGN PATENT DOCUMENTS

| AT | 409072 | 10/2008 |
| AU | 1471401 | 5/2001 |
| DE | 3905958 A1 | 8/1990 |
| EP | 1230400 A1 | 8/2002 |
| WO | WO 01/32936 A1 | 5/2001 |
| WO | WO 2003/072506 A2 | 9/2003 |
| WO | WO 2007/120735 A2 | 10/2007 |
| WO | WO 2009/059124 A2 | 5/2009 |

* cited by examiner

*Primary Examiner* — Debbie K Ware
(74) *Attorney, Agent, or Firm* — Kirton McConkie; David B. Tingey

(57) ABSTRACT

A method for the degradation of polycyclic aromatic compounds is disclosed that involves dissolving ozone in a bipolar solvent comprising a non-polar solvent in which is of sufficiently non-polar character to solubilized the polycyclic aromatic compounds, and a polar-water-compatible solvent which is fully miscible with the non-polar solvent to form a single phase with the non-polar solvent. The bipolar solvent with dissolved ozone is contacted with the polycyclic aromatic compounds to solubilize the polycyclic aromatic compounds and react the dissolved polycyclic aromatic compounds with the ozone to degrade the dissolved polycyclic aromatic compounds to oxygenated intermediates. The bipolar solvent is then mixed with sufficient water to form separate non-polar and polar phases, the non-polar phase comprising the non-polar solvent and the polar phase comprising the non-polar solvent and the oxygenated intermediates. The polar phase is then diluted and incubated with bacteria to biodegrade the oxygenated intermediates.

18 Claims, 34 Drawing Sheets

Formation of Oxygenated Intermediates

Fig. 24
A  Mixing Non-polar and Polar Organic Solvent
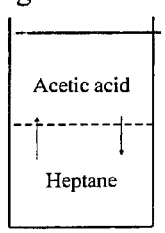
D  Crude Oil Reacts with Ozone in the Bipolar Solvent
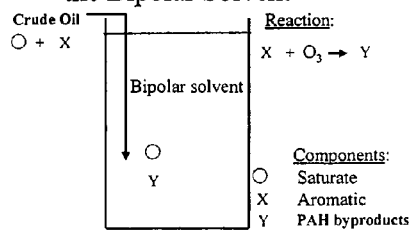
B  Miscible Phase = Bipolar Solvent
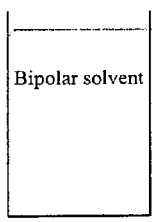
E  Water Separates Miscible Phase
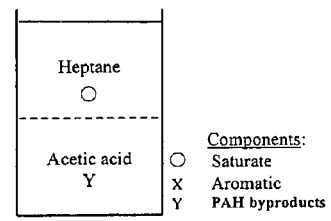
C  Saturate the Bipolar Solvent with Ozone
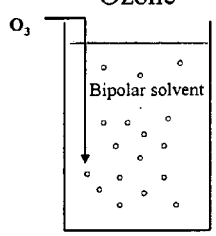

Fig. 25
a Initial Non-polar Organic Solvent with Crude oil
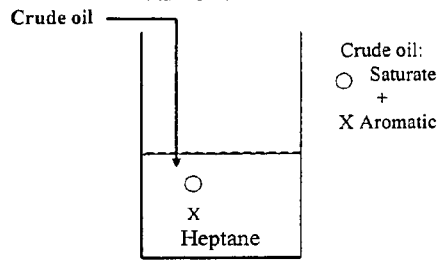
d Introduce $O_3$ with Selective Reaction of Aromatics
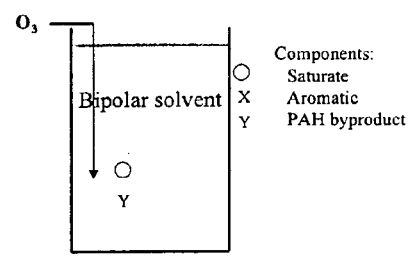
b Addition of Polar Solvent
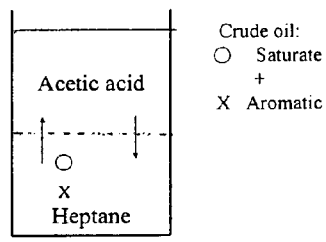
e Water Separates Miscible Phase
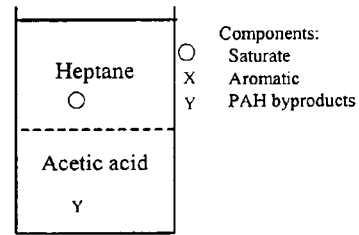
c Miscible Phase = Bipolar Solvent with Dissolved Crude oil
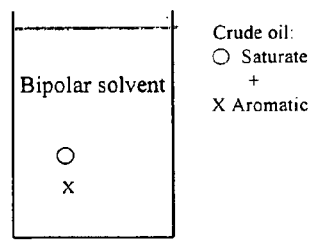

DEGRADATION OF POLYCYCLIC AROMATIC HYDROCARBONS

RELATED APPLICATIONS

This application has priority from International Application under the PCT number: PCT/US00/30599, international filing date Nov. 6, 2000, which has priority from U.S. Provisional Patent Applications 60/164,070 and 60/164,071, both filed Nov. 5, 1999.

STATEMENT REGARDING FEDERALLY SPONSORED RESEARCH OR DEVELOPMENT (Not applicable)

FIELD OF THE INVENTION

This invention relates to the chemical degradation of polycyclic aromatic hydrocarbons to render them available or biodegradation.

BACKGROUND OF THE INVENTION

Polycyclic aromatic hydrocarbons (PAHs) are a group of aromatic compounds containing two or more fused benzenoid rings in linear, angular, or cluster structure. They are ubiquitous compounds that are formed naturally during thermal geologic reactions, plant fossilization, and bacterial reactions, or formed anthropogenically during mineral production, combustion of fossil fuels in heat and power generation, refuse burning, coke oven, pyrolysis, and forest and agricultural fires. The major sources of PAHs are crude oil, coal, and oil shale. Hydrophobic, recalcitrant, and bio-accumulating, PAHs adsorb strongly to suspended particulates and biota, and accumulate in soil and sediment, resulting in serious soil contamination problems. Health concerns of PAHs arise from their toxicity, mutagenicity, and carcinogenicity. Of the 16 PAHs listed by the US EPA as priority pollutants due to their toxic and mutagenic nature, six are also known to be carcinogens. PAHs are known as active carcinogens. Their presence is an indicator of industrial pollution, and they are widely distributed in contaminated environments, particularly prevalent in burnt organic matter, air, and contaminated soil.

Both biological and chemical techniques have been used for the remediation of PAHs, although bioremediation is generally found to derive cost and technical advantages. While low-molecular-weight PAHs are susceptible to biodegradation, high-molecular-weight (HMW) PAHs that are highly mutagenic and carcinogenic remain recalcitrant. The refractory nature of HMW PAHs is partly attributed to their low aqueous solubility and bioavailability, with their degradation rates possibly limited by dissolution or desorption.

Chemical oxidation using electrophile $O_3$ has been seen as a treatment for PAH compounds in the aqueous phase or in solution. PAH compounds, such as benzo[a]pyrene, in organic solvents or in various aqueous solvents have been treated with ozone to form oxygenated products. However, these are limited in their utility for remediation because they required that the PAH compounds be in solution. Since the solubility of many PAH compounds is water is low, such solution treatment with ozone is limited as it treats only the more soluble compounds.

PAH compounds may be more soluble is certain organic solvents such as ethylene or methylene chloride, but these solvents in themselves present environmental problems and are accordingly undesirable for environmental remediation applications. In addition, the reaction products of the ozone and PAHs are often insoluble in these organic solvents, causing insoluble solid precipitates. Addition of water to these systems to solubilize the intermediates creates a multiphase system that is difficult to handle.

One of the more severe environmental problems involving PAHs is derived from oil spills. Oil spills are known for causing long-term and severe damage to environment. Biodegradation, volatilization, oxidation, and photochemical reactions alter a limited amount of the oil; the remainder of the oil is dissolved into water, and/or dispersed into soils. Many high molecular weight and hydrophobic compounds such as polycyclic aromatic hydrocarbons (PAHs) and aromatic sulfur compounds are accumulated due to their toxicity and poor water solubility, thus inaccessible to microbes and even to chemical oxidant such as $O_3$ in the aqueous phase.

Petroleum released into environments have been remediated with a wide range of chemical, physical, and biological processes. Different fractions of oil spills can transform or degrade through evaporation, plant uptake, and dissolution into water, adsorption by soil matrix, photo-oxidation, and biodegradation. Among all the attenuation phenomena, biodegradation is the primary mechanism for contaminant destruction. Biodegradation of oil in terrestrial and aquatic environments is currently the most widely accepted option for petroleum-contaminated sites. The biological degradation of oil can be taken place in aerobic or anaerobic environments, although aerobic biological oxidation is regarded as more efficient. In low oxygen conditions, such as in a oil-polluted ground water environment, the biotransformation of hydrocarbons can also occur when the nitrate, sulfate, carbon dioxide, and ferric iron were utilized as alternate electron acceptors. However, petroleum degradation under anaerobic condition is generally considered to be difficult due to the limited growth substrate, electron acceptors, and enzymatic activities. Accordingly, aerobic biological oxidation of hydrocarbons is considered to be the major biodegradation processes.

The preferential biodegradability of fractions in the crude oil spill has been reported as the n-alkanes>branch alkanes>cyclic alkanes>aromatics. In addition, volatile aromatic fractions (i.e. benzene and toluene) of oil have short residence times in the environment. Having a low preference for biodegradability with low bioavailability, low enzymatic activity, and a low volatility, high-molecular weight and hydrophobic compounds of petroleum accumulate. For example, the cyclic-alkanes and polycyclic aromatic hydrocarbons from oil spills will stay in the environment for a long period of time. Especially, PAHs are relatively stable and diagnostic constituents of petroleum. The biodegradability of polycyclic aromatic compounds are limited by their toxicity and water solubility because of most of the biodegradation occurring in the water or water-oil interface. Thus, the accumulation, persistence, and mobility/leaching potential of toxic PAHs even with effective bioremediation are still the major health and environmental concerns. In other words, although bioremediation can be a cost-effective method to remove considerable amounts of oil spills, the contaminant concentration cannot be completely eliminated because of these persistent PAH compounds.

Ozone for the oxidations of PAH compounds in aqueous solutions has been found to effective for those compounds in solution, but is not effective for these compounds that are essentially insoluble. Wastewater containing recalcitrant organic compounds has been successfully treated with ozone.

Many studies on degradation of PAHs by ozone proven can improve the solubility and decrease the toxicity of PAH compounds.

In summary, the prior-art shows (1) treatment of water soluble PAH compounds with ozone in water, generally for waste water treatment, (2) treatment of PAH in non-polar solvents with ozone, sometimes in conjunction with a non-miscible solvent to form two phases. The main problem with these systems is that non-soluble PAH compounds are not available to water solution and escape reaction with ozone. The problem with non-polar solvents is that such solvents are often toxic in themselves, and introduce their own environmental problems. In addition, the non-polar solvents do not effectively dissolve the oxygenated reaction products of ozone and the PAH compounds. Thus, these compounds can precipitate from the solvent and are not removed.

OBJECTS OF THE INVENTION

It is, therefore, an object of the invention to provide a more effective method for remediation of PAH pollutants.

Another object of the invention is to provide a method for the removal or degradation of PAH compounds that can successfully attack insoluble PAH compounds in-situ.

Another object of the invention is to provide a method of the degradation of PAH compounds the reduces the PAH compounds to readily disposable or mineralized products.

Further objects of the invention will become evident in the description below.

BRIEF SUMMARY OF THE INVENTION

The present invention involves the using an integrated approach for effective treatment of PAHs, which involves chemical oxidation as a pretreatment and biological treatment in the subsequent step. The chemical oxidation is through reactions of $O_3$ and its concomitant OH. radical with recalcitrant PAH compounds, causing ring-cleavage and producing hydroxylated intermediates such as aldehydes and acids that are more soluble. The intermediates are thus rendered more amenable to further chemical or biological degradation in the aqueous solution.

An important feature of the present invention involves the use of a bipolar solvent system, in conjunction with ozonation. The use of the bipolar solvents of the invention has been found to be more effective than the prior-art in treating and oxidizing high molecular weight and hydrophobic compounds such as polycyclic aromatic hydrocarbons (PAHs) and aromatic sulfur compounds that accumulated due to their toxicity and poor water solubility. While these compounds have previously been inaccessible to microbes and even to chemical oxidant such as $O_3$ in the aqueous phase, the practice of the present invention has allowed these compounds to be effectively treated.

The bipolar solvent system comprises (1) a non-polar hydrocarbon solvent, such as heptane, and (2) a polar, hydrophilic solvent, such as acetic acid. The non-polar component enables high concentrations of PAH molecules to be dissolved, while the polar hydrophilic solvent keeps the polar intermediates and byproducts in solution. This bipolar solvent system maintains effective exposure of all compounds to ozone throughout the course of reaction and prevents the formation of solid residues. Complete mineralization of PAHs, aromatic sulfur compounds and its daughter intermediates is possible by prolonged ozonation, or by biodegradation following a shorter duration of ozonation pretreatment.

A suitable non-polar solvent is one that solubilizes the non-polar PAH compounds. It should be immiscible in water, so that two phases will be formed upon mixture with water, and miscible with the polar solvent selected. Suitable solvents include, but are not limited to fully saturated hydrocarbons, such as liquid straight- or branch-chain hydrocarbons of 7 or more carbons, and halogenated hydrocarbons. Solvents, such as halogenated hydrocarbons that are toxic, are not preferred, but are contemplated when their use is appropriate. A suitable solvent is heptane or hexane.

The polar solvent has a sufficient hydrocarbon character such that it is miscible in the non-polar solvent, but also be sufficiently polar to be miscible in water such that it will partition into an aqueous polar phase with the polar compounds when the bipolar solvent system is mixed with water. The polar solvent should also solubilize the polar compounds that, are produced by the ozone reaction, as a function of the polar solvent in the bipolar solvent is to retain the polar reaction products in solution, and prevent their precipitation. Suitable polar solvents include organic acids such as acetic acid.

Ozone is dissolved in the bipolar solvent in sufficient quantity to react with the PAH compounds. Accordingly, the bipolar solvent should have sufficient ozone solubility to dissolve ozone in a reactive amount. The bipolar solvent stabilizes the ozone in solution to allow it sufficient time to react with the PAH compounds. For this reason, the bi-polar solvent constituents should be stable toward ozone, i.e., they do not significantly react with the ozone before it reacts with the PAH compounds. For this reason, alkane hydrocarbons, either straight or branched, are preferred for the non-polar solvent as these are stable toward ozone and have adequate ozone solubility.

To bring about bio-remediation, water is added to the reaction mixture resulting in the formation of two distinct phases. The lighter upper non-polar (heptane) phase contains any remaining parent PAHs, non-polar remnants of the PAHs, and little if any hydrophilic intermediates, whereas the heavier lower aqueous hydrophilic (acetic acid) solution accommodates a plethora of polar intermediates formed during ozonation. The amount of water is not critical, only sufficient need be added to create two-phases, which is only a small amount (usually about 5%). The aqueous phase contains only small polar hydrocarbon remnants of the PAH, which are comparatively harmless, and may be disposed of or treated by known methods. The non-polar phase may be treated to recycle the non-polar solvent.

The polar phase is mainly the polar solvent with dissolved intermediates. For bioremediation, the polar phase is separated from the non-polar phase and diluted to a degree where it can support appropriate microbes. After dilution, the polar phase is bioreacted in the presence of microbes, such as bacteria. The oxygenated intermediates are metabolized to simpler compounds. In many systems, the intermediates may be essentially mineralized (converted to non-organic compounds, such as carbon dioxide and water) if desired. The intermediates laden solution (usually about 95% water) has a high biodegradability and a low toxicity. According, inoculation or other exposure of the solution with common microbes for bioreaction, such as *E-coli*, will reduce the intermediates to smaller molecular weight compounds that are readily disposable.

Ozonation as a pretreatment for PAH deposits (such as oil spills) has potential to eliminate the toxic portion of the deposit and provide more bioavailable and water-soluble degraded PAHs as well as biodegradable saturated fractions for subsequent biological attenuation. The bipolar solvent accommodates higher ozone concentration as well as being a stable solvent for ozone. This system also provides the hydrophilic polar solvent constituent that accommodates well the polar intermediates produced by the ozonation.

The steps of the method of the invention can be executed in any order, as long as the objective of solubilizing the PAHs achieved. The basic steps include the combination of polar solvent, non-polar solvent, ozone, and contact with the PAH compounds. The PAH compounds may be in a variety of forms, such as dissolved species to the solid state. An example of an embodiment of the invention is shown in FIG. 24, which shows (a) mixing of non-polar and polar organic solvent (b) to create a miscible phase bipolar solvent, (c) saturating the bipolar solvent with ozone, (d) reacting PAHs with the ozone by adding PAH containing materials (crude oil) to the bipolar solvent, and (e) adding water to separate the miscible phase into non-polar and polar phases. In FIG. 25 is shown an alternate embodiment which shows, (a) dissolving PAHs (in crude oil) in a non-polar solvent, (b) adding a polar solvent to (c) form a single miscible phase with dissolved crude oil constituents, (d) introducing $O_3$ into the solution to react the PAH compounds, and (e) adding water to separate the miscible phase into a polar phase and a nonpolar phase. The result, in any case, is a bipolar solvent containing dissolved oxygenated intermediates.

An application of the present invention involves the treatment of spilled oil by ozone dissolved in a miscible non-polar solvent and polar solvent system to break the aromatic rings of the polycyclic aromatic hydrocarbons (PAH) to make them more adaptable to biodegradation by bacteria. As described above, the non-polar solvent serves to dissolve the crude oil compounds and to carry off the non-polar substances. The polar solvent assists in carrying the ozonated intermediates into an aqueous phase where they are more available to bacterial attack. The PAH compounds are thus reacted to form products that can be more easily broken down to harmless product and metabolized by microbes. The present invention provides a method of the treatment of PAH compounds in oil spills that are toxic, solid and insoluble in water, which otherwise would render these compounds difficult to remove and difficult for bacteria to metabolize. The ozone reacts with the PAH to open aromatic rings, making them more available as a food source, and increases oxygen functional groups which increase water solubility.

The ozone is dissolved in a solution of miscible non-polar and polar solvents. The non-polar solvent dissolves the non-polar PAH compounds and reaction products, making them available to attack by the ozone to form polar products, which are water-soluble. The non-polar solvent dissolves the crude oil, i.e., hydrophobic and non-polar compounds, which renders the oil accessible to ozone treatment.

The ozone dissolved in the bipolar solvent reacts with PAH compounds dissolved in the bipolar solvent, as well with the surface of the undissolved PAH compounds. Reaction at the solid PAH surface also serves to form more soluble compounds that can then be dissolved in the bi-polar solvent, thus degrading the solid surface. This increases the surface subject to reaction, as well as releasing more soluble compounds into the solvent. Solid hydrocarbon residues usually contain materials other than PAHs, such as mineral scale and wax deposits. While these other materials are not attacked as well be ozone, removing and solubilizing the PAH compounds can remove the physical integrity of the deposit, allowing it to break up and be carried off in the solvent in small particles. In summary, the bipolar solvent with dissolved ozone reacts PAH compounds dissolved in the bipolar solvent, with solid PAHs at the surface of solid residues, and with PAHs in free-floating particles freed from the solid surface.

The presence of the polar solvent allows the polar reaction products that are formed to be solubilized. Otherwise, these materials would precipitate out of the non-polar solvent, forming undesired solid residues. The presence of the polar solvent maintains the reaction compounds in solution, which allows further breakdown by reaction with ozone or biodegradation.

After contacting the ozone/non-polar/polar solvent system with the petroleum residues, water is added to solvent system to form two phases. The first phase contains mostly the non-polar solvent and non-polar, hydrophobic constituents and products. The second phase contains mostly water, the polar solvent and the polar products formed from reaction with the ozone. The water increases the biodegradability of the polar materials by creating an aqueous phase.

The invention is applicable for treatment PAH deposits that occur in underground hydrocarbon reservoirs, such as bitumen deposits and tar mats, as well as oil reservoirs, gas wells, and gas storage facilities.

For treatment of tar mats, the process of the invention could be modified to use a different system to contact the tar mat with ozone by injecting ozone into the water layer below the oil reservoir with its bottom tar mat. The ozone is conveyed up through the water to the mat layer of solid polycyclic aromatic hydrocarbons (PAH) underlying the reservoir where it breaks the aromatic rings. The mat can prevent the hydrostatic pressure of the water from acting on the reservoir. Treatment causes the mat to become more permeable to water, allowing the underlying hydrostatic pressure to act on the oil reservoir and aid in oil recovery. A solvent is preferred to stabilize the ozone until it reaches the mat layer. The solvent is immiscible in water, non-polar, lighter than water, and organic.

The ozone is injected in the water layer or aquifer that underlies the PAH tar mat at the bottom of an oil reservoir. Preferably, the ozone is injected alone or in the form of a solution of a non-polar solvent. The ozone rises through the water aquifer (and possibly through the non-polar solvent layer) and contracts the mat layer. There it attacks the PAH to form polar products that are partitioned into the water phase. Thus, the reaction of the ozone with the PAH compounds in the mat layer solubilizes these compounds and increases the permeability of the mat layer. The increased permeability allows the hydrostatic pressure of the water to act on the oil reservoir above the mat layer, thus increasing productivity of the oil reservoir.

The solvent helps convey the ozone to the mat layer and stabilized the ozone. The solvent also solubilizes non-polar compounds in the mat, making them more available for reaction with the ozone. The solvent is buoyant in water, and immiscible with water so that it will rise through the water to PAH layer. Suitable solvents are any buoyant material that solubilized PAH and non-polar materials, and are immiscible in water. Suitable solvents include, but are not limited to fully saturated hydrocarbons, such as straight-chain or branch-chain hydrocarbons of 7 or more carbons, and halogenated hydrocarbons.

BRIEF DESCRIPTION OF THE DRAWINGS

FIG. 24 A schematic of an embodiment of the invention.

FIG. 25 Another schematic of another embodiment of the invention.

DETAILED DESCRIPTION OF THE INVENTION

Example A

Degradation of Pyrene

Figure 1A:
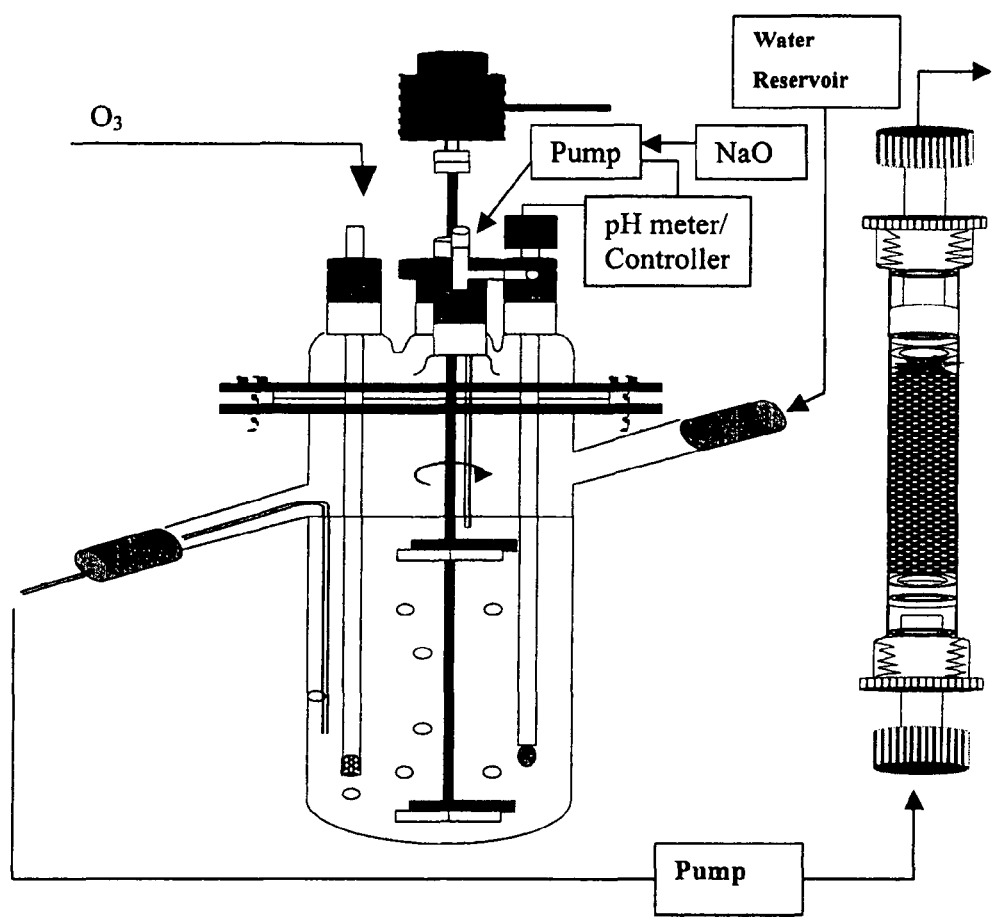
FIGS. 1a and 1b. A schematic of a reactor setup used in the examples, (a) packed column reactor fed by an ozonated water reservoir; (b): batch reactor.

This example focuses on an integrated approach for the degradation of pyrene involving chemical oxidation followed by biological treatment. The objectives were to: 1) provide mechanistic details in the degradation of pyrene subject to ozone treatment, 2) test the combined technique of ozone pretreatment followed by biological degradation, and 3) test a pretreatment column to promote efficient use of chemical oxidants and biodegradability. Batch and packed column reactors were used to examine the degradation pathways of pyrene subject to ozonation in the aqueous phase. After different ozonation times, samples containing reaction intermediates and byproducts from both reactors were collected, identified for organic contents, and further biologically inoculated to determine biodegradability. The $O_3$-pretreated samples were incubated for 5, 10, 15, and 20 days, after which biochemical oxygen demand (BOD), chemical oxygen demand (COD), and toxicity tests along with qualitative and quantitative GC/FID and GC/MS analyses of pyrene, intermediates, and products were performed. Intermediates identified at different stages included 4,5-phenanthrenedialdehyde, 2,2',6,6'-biphenyltetraaldehyde, and long-chain aliphatic hydrocarbons, which suggested that the degradation of pyrene was initiated by $O_3$ via ring cleavage at the 4,5- and 9,10-bonds and that further oxidation ensued via reactions with both $O_3$ and OH. until complete mineralization. Intermediates formed during chemical oxidation were biodegradable with a measured first-order rate constant ($k_0$) of 0.243 day$^{-1}$. The integrated chemical-biological system appeared to be feasible for treating recalcitrant compounds, and a chemical pretreatment column was particularly useful in promoting soluble intermediates from otherwise highly insoluble, inaccessible pyrene.

Materials and Methods

Chemicals

Ozone (~1% w/w ozone in air) was generated from filtered, dry air by an ozonator (Model T-816, Polymetrics Corp.). Pyrene (99%, Aldrich Chemical Co.) was washed with distilled-deionized (DD) water three times, extracted by dichloromethane (DCM), and the solvent evaporated by a gentle stream of nitrogen gas. Stock and working indigo blue solutions were prepared from potassium indigo trisulfonate ($C_{16}H_7N_2O_{11}S_3K_3$, Aldrich Co.) per Standard Methods (APHA et al., 1992a). Polyseed (Hach Co.) was used in dilution water for biochemical oxygen demand (BOD) measurements per Standard Methods (APHA et al., 1992b). Inoculum for toxicity test was prepared according to a Hach method (HACH, 1988-1995b). COD digestion solutions (0-15,000 mg/L, 0-40 mg/L range, Hach Co.), ToxTrak™ reagent powder pillows, and ToxTrak™ accelerator solution (Hach Co.) were purchased and used according to the manufacturer's methods without further processing. Low-organic (<15 ppb as TOC), low-ion (resistivity >18 MΩ-cm), and non-pyrogenic (up to 4-log reduction with reverse osmosis pretreatment) DD water was used in all procedures (4-stage Mill-Q Plus system, Millipore Co.). Dichloromethane (Fisher Scientific) of HPLC grade was used in liquid-liquid extraction procedures. Other chemicals used in this research were of reagent grade.

Analytical Methods and Equipment

Aqueous concentration of ozone in the reactor was determined by sample absorbance at 600 nm using a 1-cm quartz cell with a HP-8452 Spectrophotometer (HP-8452 UV-Vis Spectrophotometer, Hewlett Packard Co.) according to the Indigo Blue Method (APHA, et al., 1992a). The following formula was used for our modified procedure based on weighing:

$$O_3 \text{[mg/L]} = ((SW+IW)/SW) \times ((DF \times A_{blank}) - A_s)/f$$

Where:
SW [g]=sample weight ($W_{I+S} - W_I$),
$W_{I+S}$ [g]=weight after adding indigo blue solution (7 mL) plus sample (~3 mL),
$W_I$ [g]=weight after adding indigo blue solution (7 mL),
IW [g]=weight of indigo blue solution ($W_I - W_{emp}$),
$W_{emp}$ [g]=weight of the empty test tube,
$A_{blank}$ [#]=absorbance at 600 nm of the indigo blue analytical solution without the sample,
$A_s$ [#]=absorbance at 600 nm of the indigo blue analytical solution plus the sample,
DF [#]=dilution factor, DF=IW/(SW+IW),
f=0.42.

Sample COD determinations were made per Hach COD method (HACH, 1988-1995a) using a COD reactor (Hach Co.) and a direct reading spectrometer (DR/2000, Hach Co.) or the HP-8452 spectrophotometer for ultra-low range COD measurement at $\lambda$=356 nm. Sample BOD determinations with required controls were made per Standard Methods (APHA et al., 1992b) using an oxygen meter/electrode system (YSI Model 57 oxygen meter with oxygen electrode, YSI Co.). Sample toxicity was quantified based on a colormetric method of measuring the reduction of the redox-active dye resazurin by bacterial respiration (HACH, 1988-1995b) with the spectrometer (DR/2000, Hach Co.).

Quantification of Organics

Extraction. Typically a 200-ml sample containing pyrene and/or organic products was extracted three times using a total of 100 ml DCM. The combined extract was concentrated to 4 ml by evaporation using a Kuderna-Danish evaporator (ACE glass Inc.) followed by further evaporation to 0.2 ml using a gentle stream of $N_2$ gas. The extract was stored at −12° C. until analysis.

Quantification and identification. Extracted samples containing pyrene, intermediates, and products were analyzed using a gas chromatograph (GC) (HP 5890, Hewlett Packard Co.) equipped with a capillary column (RTX-1 non-polar column, 30 m×0.25 mm×0.25 μm, Baxter Co.) and a flame ionization detector (FID). The GC was interfaced and programmed with the HP Chemstation software (Hewlett Packard Co.). Quantification was based on an external standard and calculation using a pyrene calibration curve. A 5:1 split injection was used with an oven temperature from 50° C. (1 min) to 300° C. (60 min) at a 5° C./min ramp.

Tentative identification of intermediates and oxidation products were performed using a GC (HP 6890) with a capillary column (DB-1 non-polar column, 60 m×0.25 mm×0.25 μm, J & W Co.) and a mass spectrometry detector (MS) (HP 6890) interfaced and programmed with the HP Chemstation software (Hewlett Packard Co.). A split ratio of 5:1, solvent delay at 12 min, and scan range from m/z 15 to m/z 500 at 1.4 scan/sec were used. The oven temperature was set from 50° C. (1 min) to 300° C. (60 min) at 5° C./min ramp. The HP Chemstation library (Hewlett Packard Co.) was used for species identification as a supplement to mass spectral and retention time characteristics. All library-matched species exhibited the degree of match better than 90%. In addition, comparison of parent compound structure and interpretation of mass spectra of the intermediates from ion fragmentation information were performed particularly for the identification of key intermediates 4,5-phenanthrenedialdehyde and 2,2',6,6'-biphenyltetraaldehyde.

Reactors and Procedures

Reservoir of Ozonated Water

Figure 1B:
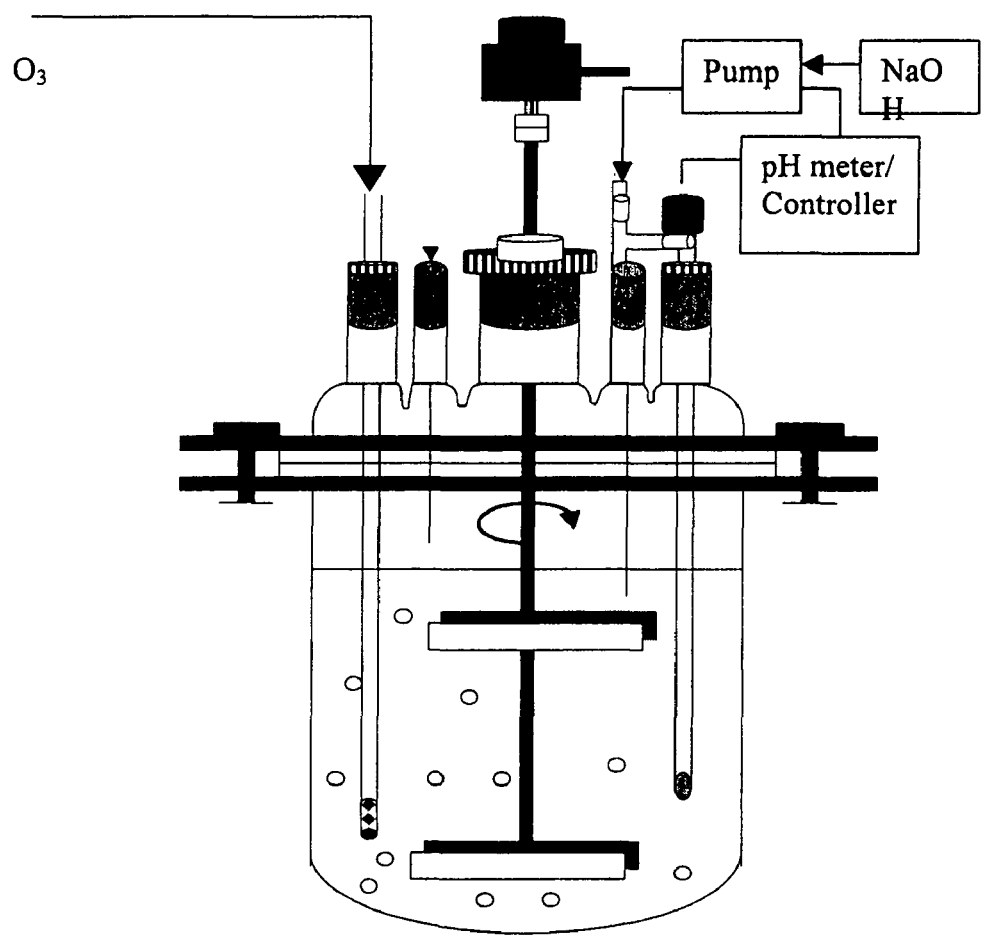

Ozone, generated at an applied voltage of 120 V and air flow rate of 2 L/min, was spared into a mixed flow-through reservoir (CSTR type) holding a water that was slowly overflowing but at a constant volume of about 3 L (FIG. 1). The pH of this reservoir was maintained at 7 by automatic delivery of concentrated NaOH via a peristaltic pump connected to a pH probe/meter/controller system (Cole Parmer Co.). During ozonation, slowly overflowing (50 mL/min) water was passed through, ozonated in, the reservoir and the dissolved ozone concentration was continually monitored. After the aqueous ozone reached the steady-state concentration, the ozonated water was introduced into the packed column reactor by a peristaltic pump (Masterflex computerized drive, Cole Parmer Co.) (FIG. 1).

Packed Column Reactor

Weighted glass beads (~150 g) of ca. 1-mm diameter were washed with concentrated $K_2Cr_2O_7/H_2SO_4$, concentrated $HNO_3$, DD water, acetone, and DCM sequentially, then dried at 400° C. overnight. About 1 g of pyrene was weighted and dissolved into 20 ml DCM, the solution was added with the pretreated glass beads. The mixture was agitated and DCM evaporated completely by blowing of $N_2$ gas. The glass beads mixed with recrystallized pyrene solid were packed into a glass column (Adajusta-Chrom 0.9839"×300 mm glass column, ACE glass, Inc.). The length of the packed zone was about 7.5 in. During the course of reaction, water carrying dissolved $O_3$ was passed through the packed column in the upflow direction using a peristaltic pump at 44 mL/min, as shown in FIG. 1. Samples were collected at the column outlet at various time intervals, filtered through a 0.45-1 μm filter, and analyzed for $O_3$ as well as organic contents. Tests of $BOD_5$, 20-day BOD, COD, toxicity, and qualitative and quantitative analyses of pyrene, intermediates, and products of both chemical and biological treatments were performed simultaneously.

Batch Reactor

A glass batch reactor with a working volume of 1,700 mL was used (ACE glass Inc.). Mixing of this reactor was provided by two TEF agitators (ACE glass Inc.) driven by a variable speed controller/motor (ACE glass Inc.) through a flexible drive cable. Ozone gas was sparged into the reactor near the bottom through a glass dispersion tube (ACE glass Inc.) Constant pH during reaction was maintained at 7 automatically. After about 1 g of pyrene solid was added into the reactor filled with 1,700-ml water, ozone was sparged into the batch. The dissolved ozone concentration was continually monitored. Samples were collected after 2, 4, 6, 8, 10 min of ozonation and filtered through a 0.45-μm filter. Tests of $BOD_5$, COD, toxicity, and qualitative and quantitative analyses of pyrene, intermediates, and products before and after chemical and biological treatments were performed simultaneously.

Results and Discussion

Ozonation of pyrene was carried out in batch and column reactors to study: 1) the effect of reactor on intermediates and products formation, 2) the degradation pathway of pyrene under ozonation, 3) the biodegradability of intermediates, and 4) the feasibility of a combined chemical-biological treatment system for pyrene. Reaction solutions during ozonation and biodegradation processes at different stages were collected and the intermediates and byproducts identified by GC/MS techniques.

1. Effects of the Reactor Type on Intermediates and Products Formation

To delineate the influence of reactor configurations on the formation of intermediates and products, ozonation experiments using aqueous and excess pyrene were carried out in batch and packed column reactors. $BOD_5$ and COD were measured for three ozonated, filtered solutions: 1) a saturated aqueous solution of pyrene (~0.13 ppm), 2) the solution after ozonation of an excess pyrene suspension (1 g/1.7 L), and 3) the effluent of a column packed with excess pyrene solid (1 g) and glass beads (7.5 in. in bed-length). The saturated pyrene solution was prepared by allowing excess pyrene solid to reach dissolution equilibrium in water overnight followed by removal of the excess solid using a 0.45-μm filter. The ozonated batch solution was obtained after 10 min of ozonation and filtered, while the effluent was collected from the packed column fed with ozonated water over a 4-hr period. Table A-I shows the results of $BOD_5$ and COD measurements. The $BOD_5$ for the saturated pyrene solution approximates over 80% of the COD value, suggesting that pyrene in its dissolved form is amenable to biodegradation, albeit in small quantity. The aqueous phase COD from the ozonated batch reactor increased after ozonation possibly due to occurrence of intermediates or pyrene-derivatives that are more soluble in water as a result of ozonation. The new, lower $BOD_5$/COD ratio of 66% appeared to suggest either that a larger amount of degradable substrates was available after ozonation that resulted in lower $BOD_5$, or more likely that the biodegradability of the ozonated solution decreased as a result of ozonation possibly due to formation of slightly more recalcitrant intermediates. Following the reasoning of increased aqueous COD due to abundance of more soluble intermediates, the measured COD for column effluent would imply that it contained much more intermediates and byproducts. The new $BOD_5$/COD ratio registered a slightly smaller value of 0.53. These ratios are well within those commonly observed for domestic wastewater and do not seem to signify toxicity.

Figure 2:
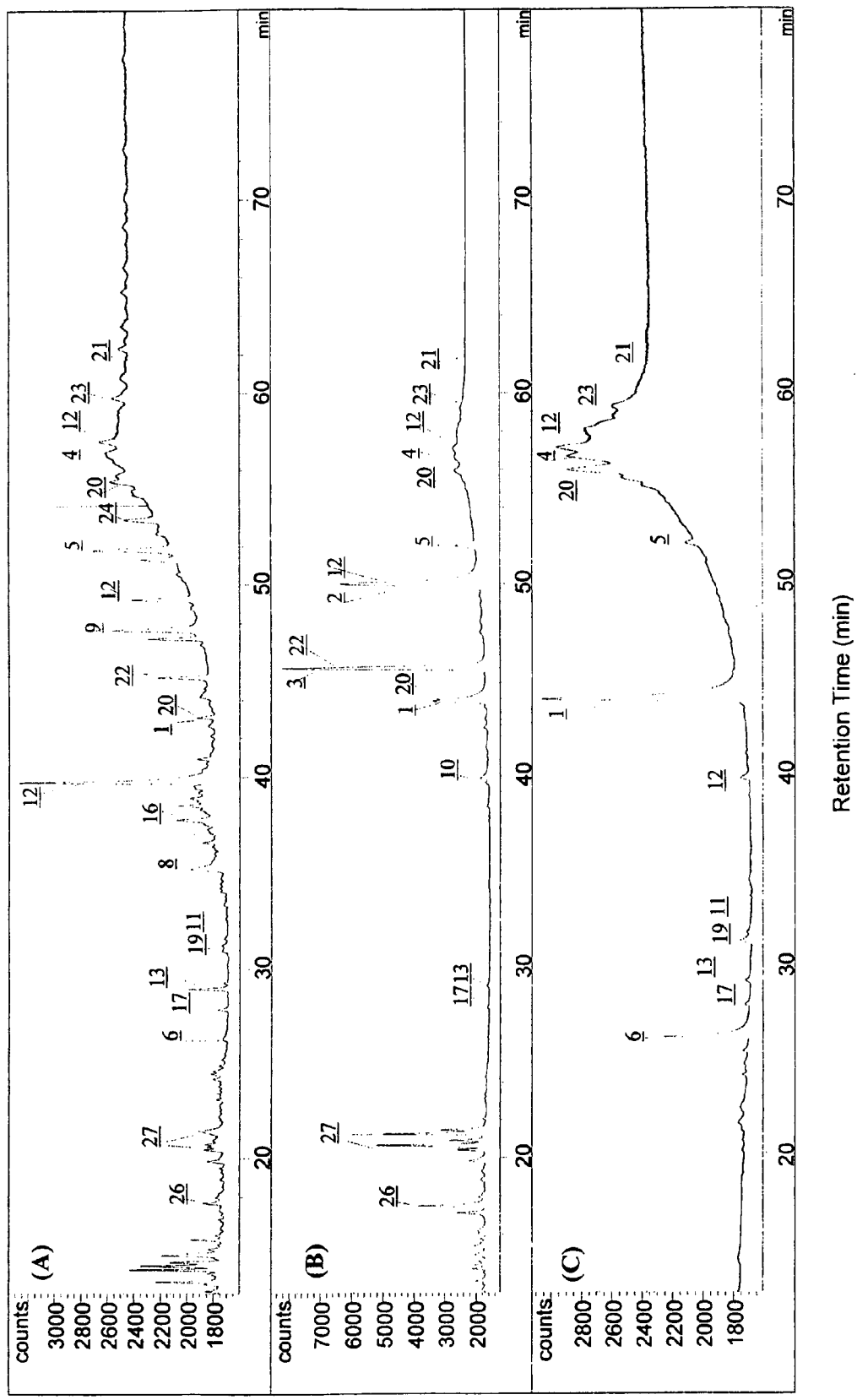
FIG. 2. Gas chromatographs of intermediates and products from pyrene in effluents of: (a) column reactor prior to ozonation, (b) column reactor after 1 hr of ozonation, and (c) batch reactor after 1 min of ozonation.
Identified: compounds include 1-pyrene, 2-4,5-phenanthrenedialdehyde, 3-2,2',6,6'-biphenyltetraaldehyde, 4-1,2-benzenedicarboxylic acid, diisooctyl, 5-benzylbutyl phthalate, 6-diethyl phthalate, 8-4H-cyclopenta[def]phenanthrene, 10-xanthone, 11-butylate hydroxytoluene, 2-dibutyl phthalate, 13-nonyl phenol, 16-hexadecanoic acid, 17-tetradecane, 19-hexadecane, 20-henicosane, 21-6-propyl tridecane, 22-docosane, 23-hexacosane, 24-pentacosane, 26-unknown (m/z=154), and 27-unknown (m/z=139).
Figure 3A:
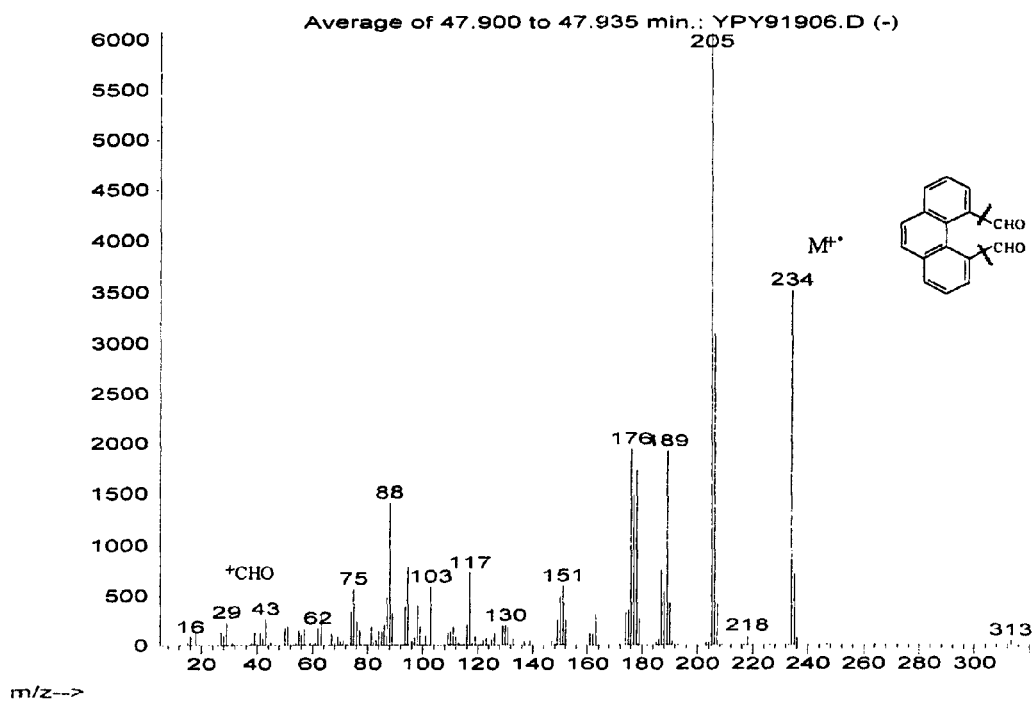
FIG. 3. Mass spectra of (a) 4,5-phenanthrenedialdehyde, and (b) 2,2',6,6'-biphenyltetraaldehyde.
Figure 3B:
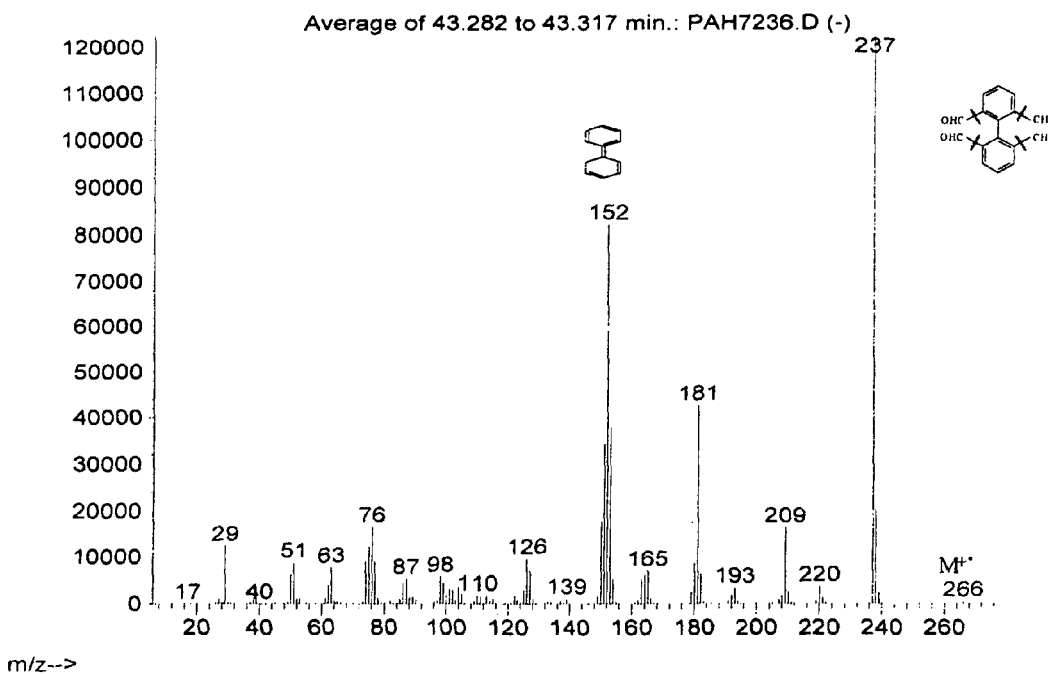

Parallel to $BOD_5$ and COD measurements of the ozonated reaction media, the effects of reactors on intermediates formation were further probed using GC/FID and GC/MS identification techniques. FIG. 2 shows the gas chromatograms of parent and identified intermediate compounds in 1) the aqueous pyrene solution without ozonation, 2) ozonated column effluent, and 3) ozonated batch solution. Despite its low solubility, the parent pyrene (peak 1 as labeled) was found in all solutions. As listed in Table A-II, twenty-five other compounds were found in the column effluent, and except for two of them were identifiable by MS library comparison. Two important intermediates 4,5-phenanthrenedialdehyde (species 2) and 2,2',6,6'-biphenyltetraaldehyde (species 3) were found in the ozonated column effluent but not in the ozonated batch solution. The mass spectra of these two intermediates, species 2 (m/z 234) and 3 (m/z 266), are shown in FIGS. 3(*a*) and (*b*), respectively.

In the ozonated batch solution, found in place of the di- and tetra-aldehydes was a variety of benzenedicarboxylic acids, which apparently are subsequent byproducts in the oxidative chain of events. Comparison of gas chromatograms (b) and (c) of FIG. 2 shows that the column effluent contained an abundance of intermediates (such as species 2 and 3) whereas the ozonated batch solution contained less intermediates but more fragments that were products further down the degradation process. These identifications are consistent with the higher COD measurement in the column effluent than that in the batch solution.

Figure 4:
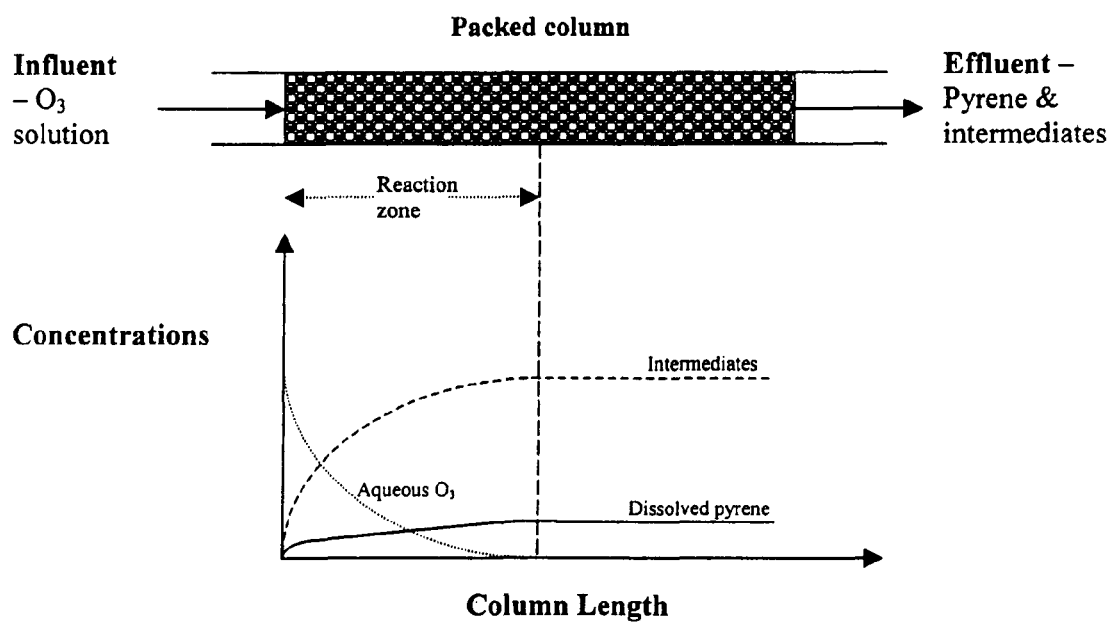
FIG. 4. Schematic diagram illustrating concentration profiles of reactants and intermediates in a flow-through column reactor.

These results indicated that ozone was capable of degrading pyrene via ring opening, as evidenced by intermediates dialdehyde and tetraaldehyde (species 2 and 3 in the column effluent), and further oxidation by ozone (and other oxygenated radicals to be discussed) to other fragments and byproducts (such as 1,2-benzenedicarboxylic acid, diisooctyl 4, benzylbutyl phthalate 5, hexacosane 23, henicosane 20, and nonyl phenol 13 in the batch solution) if the intermediates were to remain exposed to ozone. These results underscored the importance of the role that the reactor configuration played in determining the kinds and amounts of intermediates and byproducts to be found after ozonation. The influence of a column reactor on the types and amounts of intermediates and byproducts formed are illustrated in FIG. 4. A batch reactor readily subjects the intermediates from pyrene to continual $O_3$ attack and further degradation, whereas the column reactor allows the intermediates to be eluted from the $O_3$-rich area, i.e., the reactive zone. Thus, to promote the formation of intermediates that could be subsequently biodegraded rather than relying upon ozone as the sole oxidant in the complete degradation of pyrene, a column reactor was used to collect effluent that was rich in partially treated intermediates for further mechanistic and biodegradability studies.

Degradation Pathway of Pyrene in Ozonated Water

Figure 5:
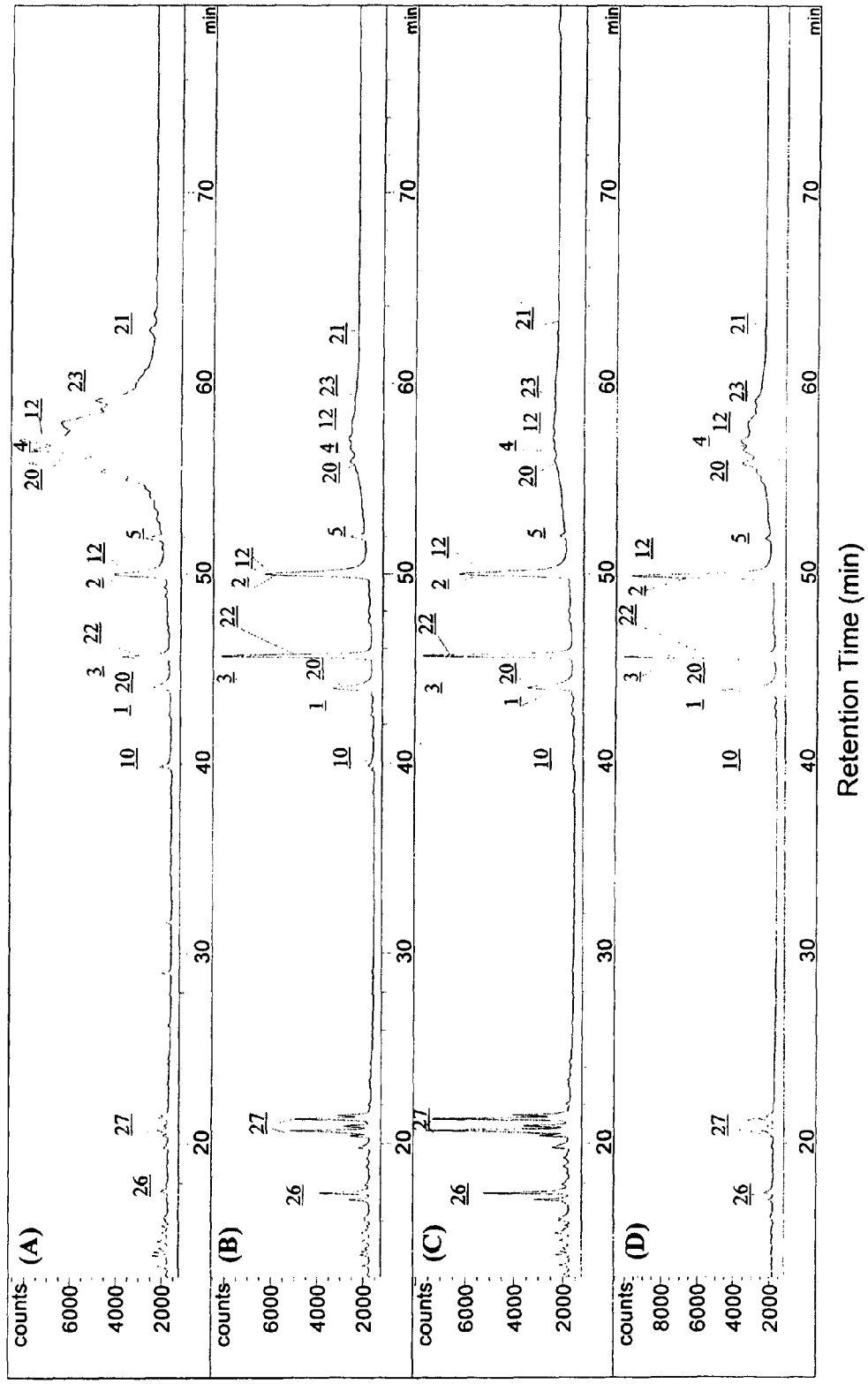
FIG. 5. Products from pyrene in ozonated column effluents collected at different time periods: (a) First 0.5 hr; (b) 0.5-1.0 hr; (c) 1.0-1.5 hr; and (d) 1.5-2.0 hr.
Identified: 1-pyrene, 2-4,5-phenanthrenedialdehyde, 3-2,2',6,6'-biphenyltetraaldehyde, 4-1,2-benzenedicarboxylic acid, diisooctyl, 5-benzylbutyl phthalate, 10-xanthone, 12-dibutyl phthalate, 20-henicosane, 21-6-propyl tridecane, 22-docosane, 23-hexacosane, 26-unknown (m/z=154), and 27-unknown (m/z=139).

The effluent from a pyrene-packed column fed with ozonated water was collected and identified for intermediates and byproducts via GC/FID and GC/MS. The up-flow influent water contained 5 mg/L $O_3$ while the effluent none, indicating that complete consumption of $O_3$ occurred in the column. The filtered (through 0.45 μm) effluents exhibited yellowish intermediate compounds that were not apparent in previous samples from ozonated batch solutions. The absence of colored compounds in the batch reaction was attributed, as explained previously, to continual degradation of the colored intermediates by $O_3$. FIG. 5 identified species found in the effluents collected at different time intervals. These identified species, including the dialdehyde (2) and tetraaldehyde (3) intermediates, resembled those identified in FIG. 2. In addition to the molecular ion peaks, other fragments including m/z 205, 176 and 29 corresponding to the loss of —CHO groups were noticeable in the mass spectra in the case of 4,5-phenanthrenedialdehyde, and m/z 237, 29 of 2,2',6,6'-biphenyltetraaldehyde. A biphenyl fragment was found at m/z 152 in FIG. 3(b), which suggested the presence of a biphenyl structure as 2,2',6,6'-biphenyltetraaldehyde.

FIG. 2a showed a substantial variety of (unozonated) compounds eluted from the column even prior to the start of ozonation. These compounds were in many cases similar to that after ozonation as shown in FIG. 5a. This was attributed to the occurrence of autooxidation (reaction with molecular oxygen), which is also an oxidation process albeit at a much slower rate than of oxidation by ozone, resulting in similar intermediates and products. Autooxidation of pyrene could have occurred during storage on the shelf or by dissolved oxygen after being dispersed and thinly packed in the column. The latter was more likely as calibration runs prior to column loading did not reveal the intermediates. However, clearly discernable was that these intermediate and product peaks intensified pronouncedly after the ozone oxidant was introduced, as evident in comparison of FIG. 5a with FIG. 2a. Data estimation suggested that oxygenated compounds such as 5, 8, 9, 11, 12, 13, and 16 increased by 1290%, 1160%, 690%, 1130%, 60%, 20%, and 200%, respectively, while aliphatic compounds such as 17, 18, 20, 22, 23, and 24 increased by 410%, 1410%, 3530%, 3530%, 2670%, 4140%, respectively.

Figure 6:
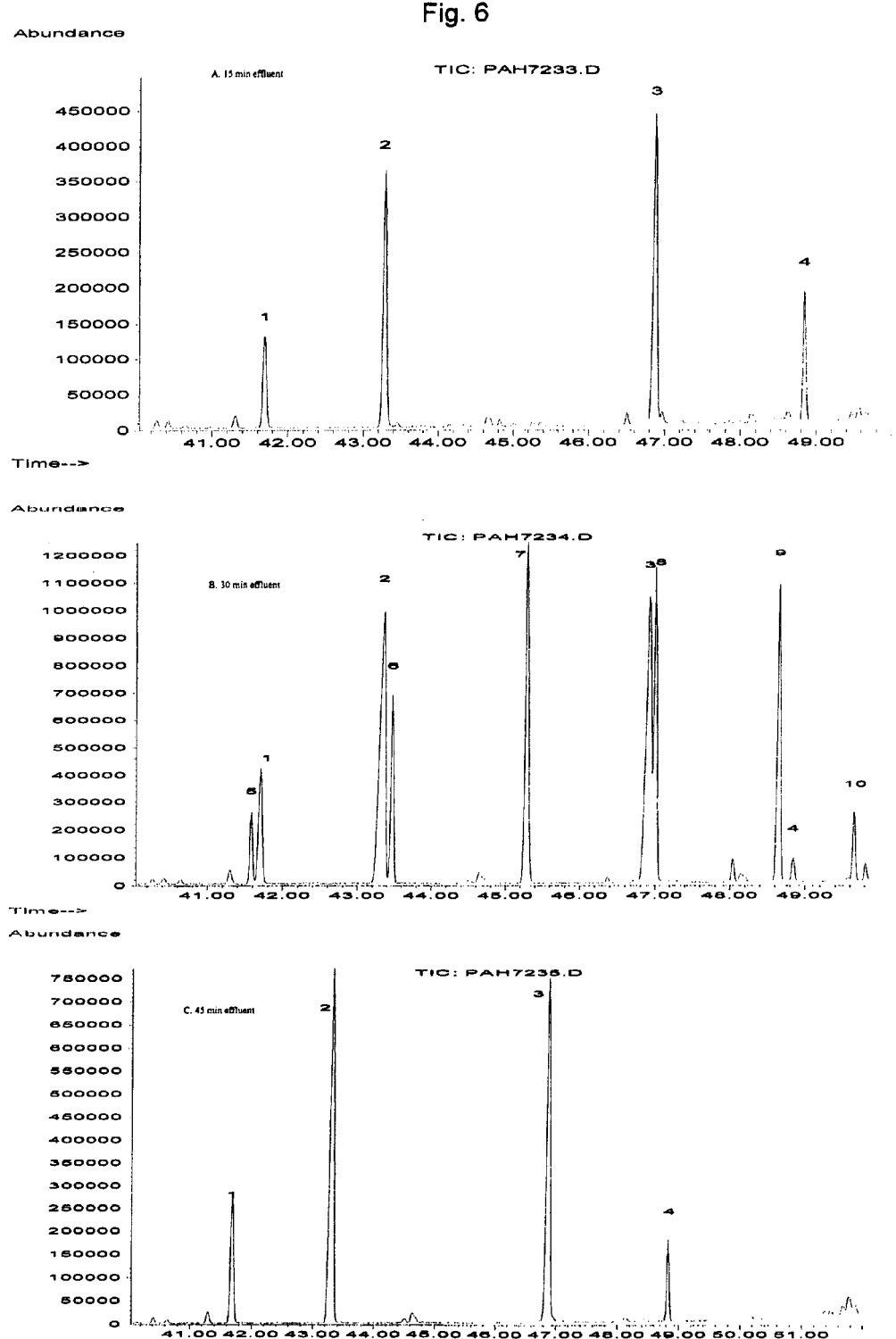
FIG. 6. Gas chromatograms of different intermediates from pyrene (suggestive of free-radical reactions) identified at different treatment stages: (a) compounds 1-4 during first 15 min; (b) 5-10 in addition to 1-4 during 15-30 min; and (c) 1-4 during 30-45 min.
Identified: 1-pyrene, 2-2,2',6,6'-biphenyltetraaldehyde, 3-4,5-phenanthrene dialdehyde, 4-1,2-benzenedicarboxylic acid, diisooctyl, 5-henicosane ($C_{21}$), 6-docosane ($C_{22}$), 7-tricosane ($C_{23}$), 8-tetracosane ($C_{24}$), 9-pentacosane ($C_{25}$), 10-hexacosane ($C_{26}$).

FIG. 6 identified intermediates found in ozonated column effluents collected by more frequent samplings. The gas chromatograms as shown focused on species with retention times of 40-50 min, which consisted mainly of pyrene, 2,2',6,6'-biphenyltetraaldehyde (2), 4,5-phenanthrenedialdehyde (3), and 1,2-benzenedicarboxylic acid, diisooctyl (4). In addition to these major species, spectrum (b) of FIG. 6 also identified long-chain aliphatic carbon compounds, including $C_{21}$, $C_{22}$, $C_{23}$, $C_{24}$, $C_{25}$, and $C_{26}$, shown as species 5 to 10, respectively. These long-chain hydrocarbons disappeared as the column effluent established steady-state levels of intermediates; henceforth only four major intermediates (1 to 4) remained after 45 min., as shown by chromatogram of FIG. 6(c). The presence of long-chain aliphatic hydrocarbons that have more carbons than the 16-C pyrene parent is suggestive of, during ozonation, the involvement of free-radical pathways in which radical recombinations are prevalent. The decomposing of $O_3$ in water is known to occur through a series of free radical chain reactions that involve reactive radicals including $OH./O.^-$, $HO_3./O_3.^-$, and $HO_2./O_2$. These reactive radicals are potent oxidants that can react with organic molecules leading to their mineralization.

Figure 7A:
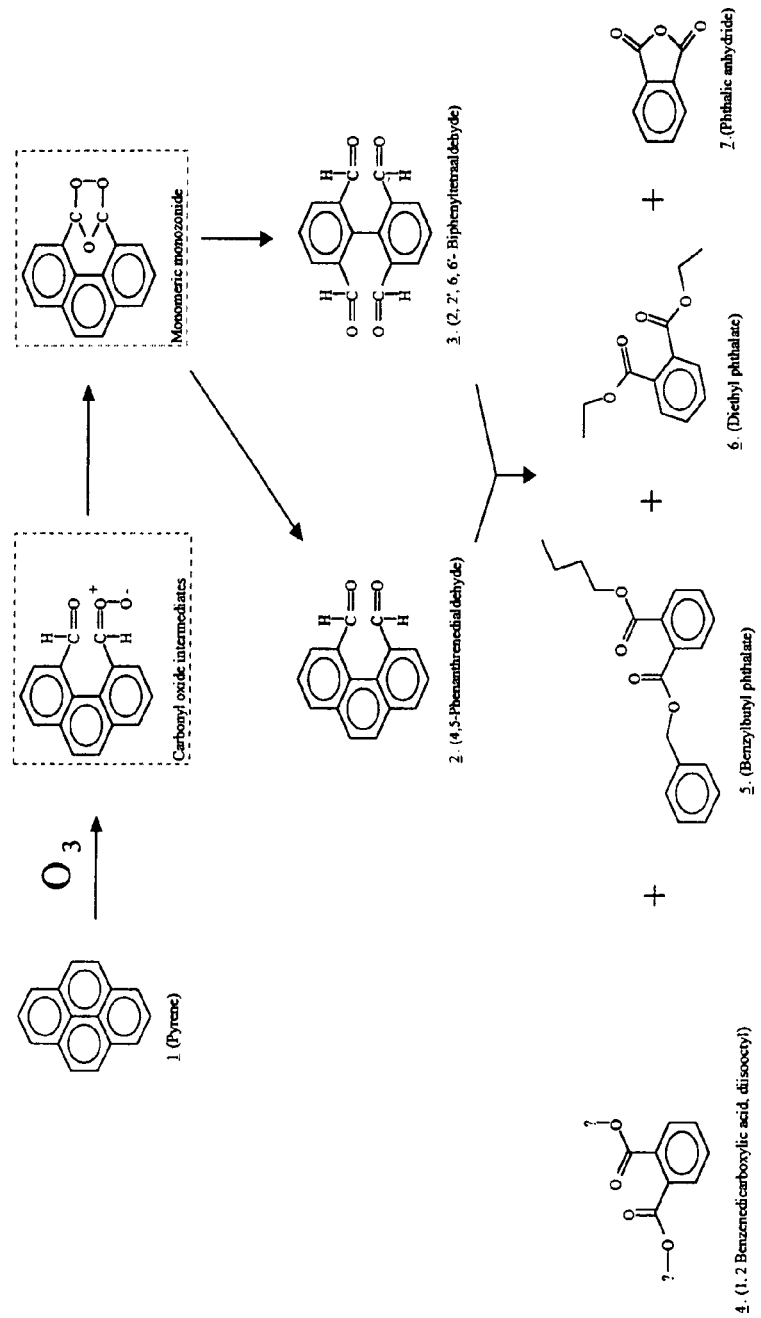
FIGS. 7a-7d. Proposed degradation mechanism of pyrene illustrating proposed intermediates as well as identified intermediates and products during ozonation.
Figure 7B:
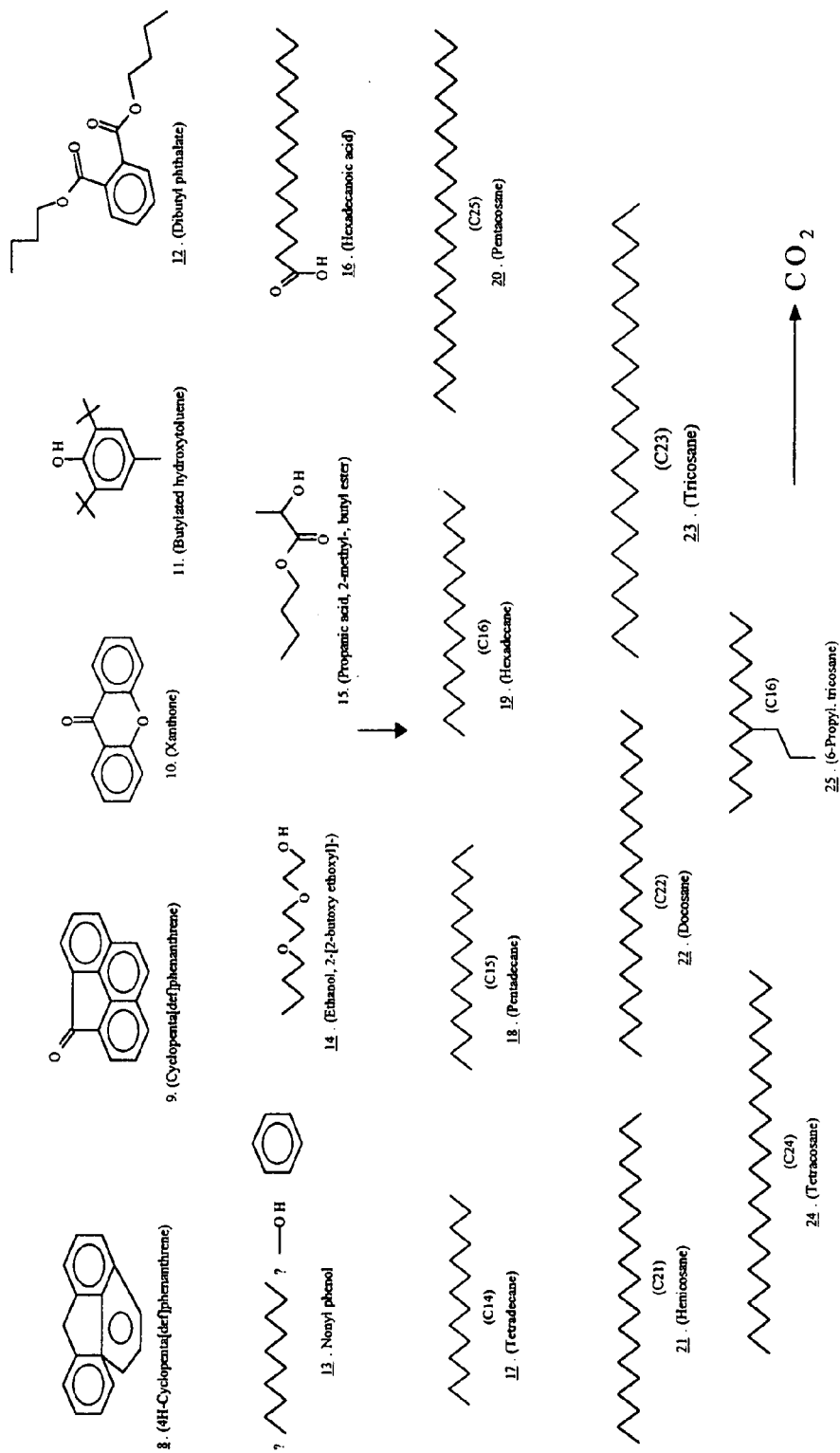
Figure 7C:
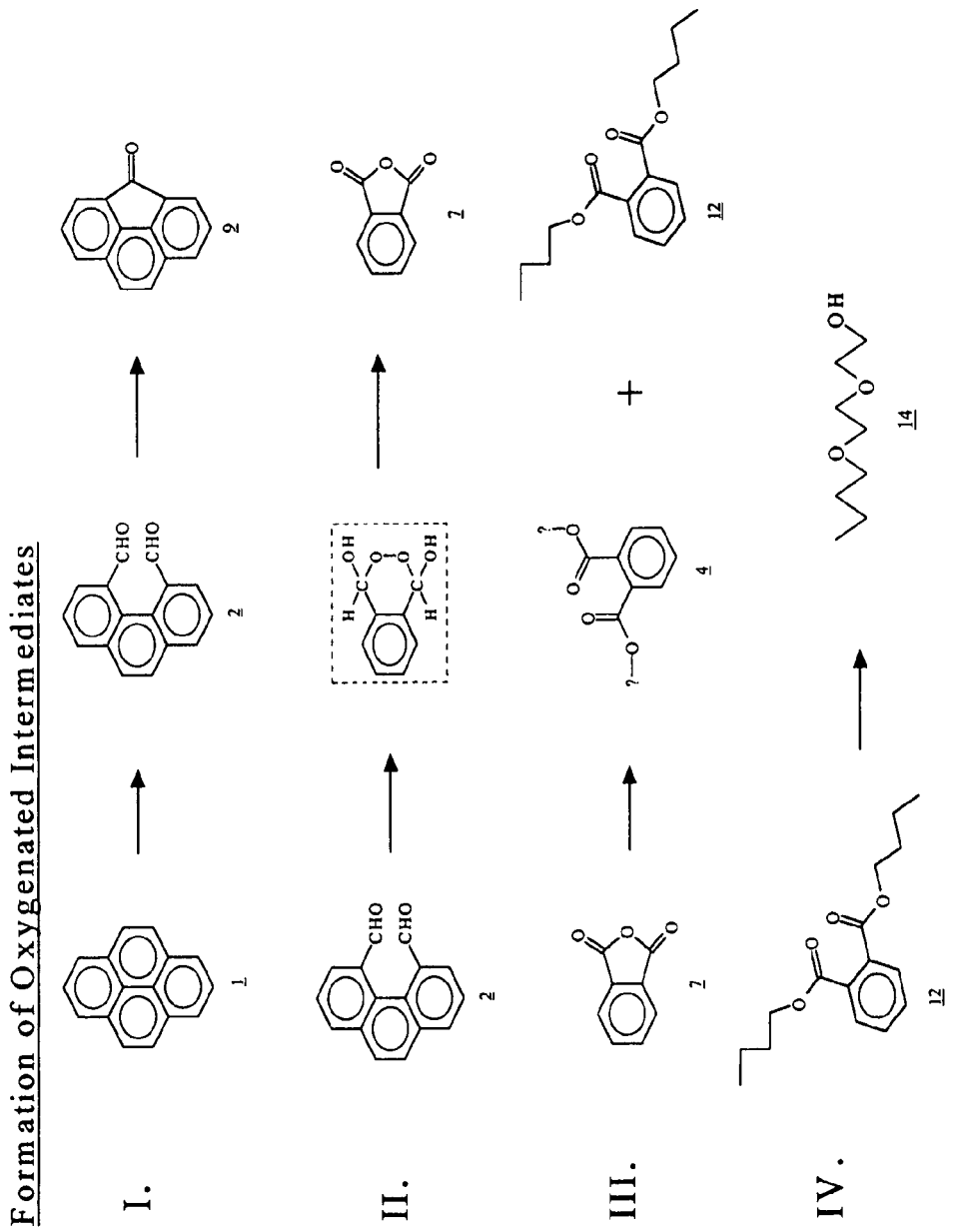
Figure 7D:
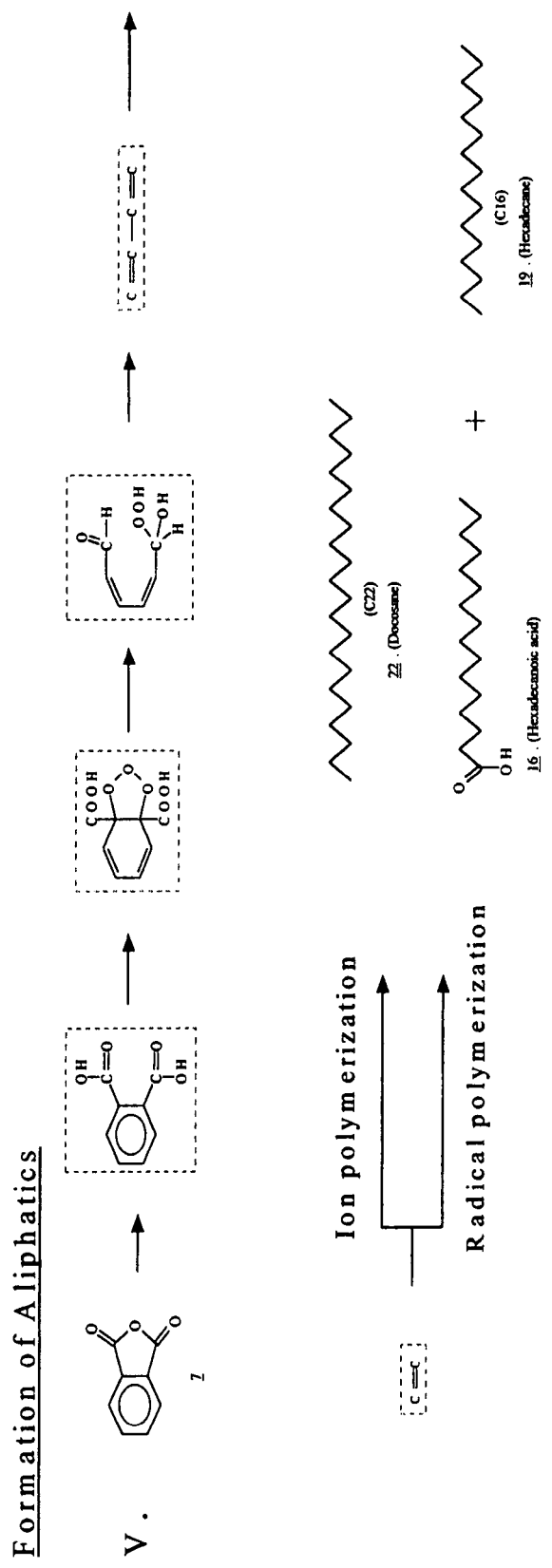

With identified intermediates and byproducts, in FIGS. 7a and 7b (the top of 7b continues from the bottom of 7a) is shown a proposed mechanism depicting the degradation pathway of pyrene under ozonation. As shown, the degradation was initiated by electrophilic attack of $O_3$ on one of the electron-rich conjugate rings of the pyrene molecule resulting in the formation of dialdehyde (2) and, upon another ring-opening attack, tetraaldehyde (3). Pyrene has an asymmetrical fused-ring structure. The bonds between fused angular rings, as in 4,5- and 9,10-bonds (referred to as the K-regions), have the highest bond order (0.833) and shortest bond length (1.367) in the pyrene molecule (Harvey, 1997). These bonds show considerable double-bond character and are more reactive than other bonds, consistent with K-regions being the first activated reaction sites in metabolic oxidation. The preferential attack of $O_3$ on the 4,5-bond of the pyrene molecule is also explained in terms of localization energy that marks the site as being most reactive (Bailey, 1982). Subsequent reactions of intermediates with $O_3$ or oxygenated radicals (e.g., OH., $O_2.^-$, $O_3.^-$) resulted in additional intermediates (4)-(16). The production of long-chain aliphatic hydrocarbons, compounds (13) through (25), was attributed to oxidation reactions prompted by $O_3$, OH., and other free radicals. With proposed intermediates and identified ones, FIGS. 7c and 7d details the formation and destruction of some of these compounds based on known reaction pathways reported in the literature. As shown, these reactions produced alkyl radicals that further propagated chain reactions and eventually led to polymerization via recombination of the organic radicals. Thus, the formation of many oxygenated intermediates (4, 7, 9, 12, 14, 16) as well as n-alkanes (19, 22) could be accounted for by FIGS. 7c and 7d.

Another observation supporting the involvement of free radicals was the disappearance of these long-chain alkanes if the effluent was subject to prolonged ozone hydrolysis. Long-chain alkanes are characteristically resistant to electrophilic attack by $O_3$ yet susceptive to OH. oxidation. Simpler short-chain polar aliphatic compounds were expected but not found in the reaction mixture; their absence was attributed to analytical extraction and preparation procedures that failed to retain compounds with less than six carbons. As $O_3$ undergoes hydrolysis during ozonation, both $O_3$ and OH. are available for the degradation of pyrene. It is plausible that the degradation pathway is initiated mainly via ring opening by $O_3$, continued in fragmentation by both $O_3$ and OH., and ultimately brought to complete mineralization primarily via OH. radicals.

Biodegradation of Ozonated Column Effluent

Figure 8:
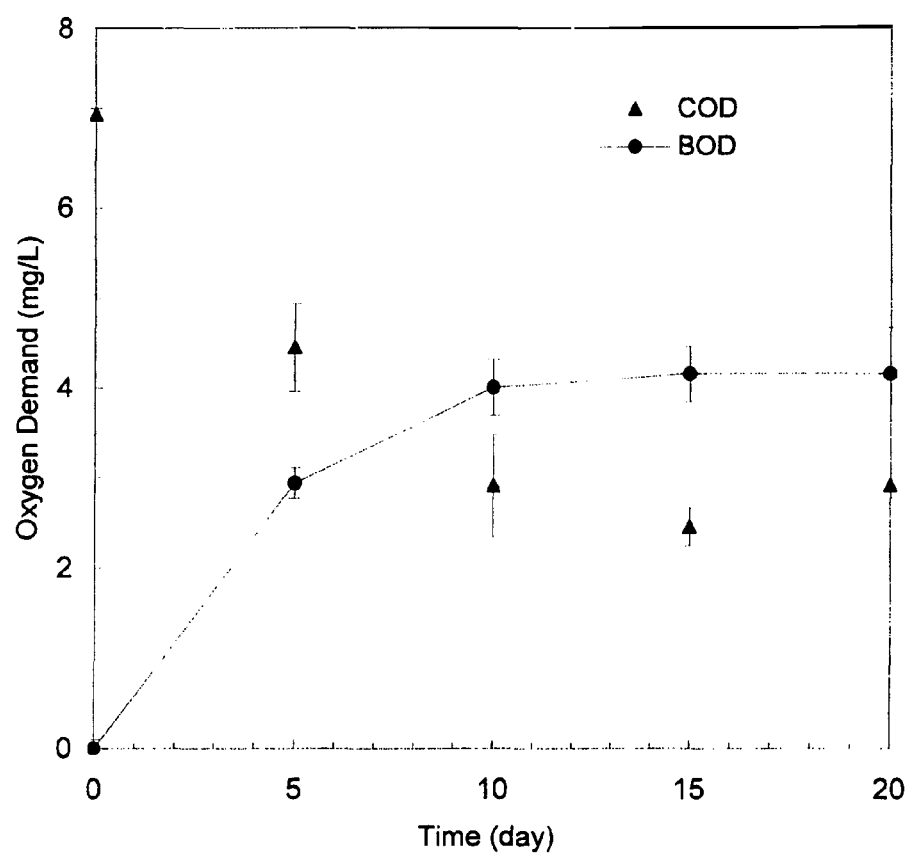
FIG. 8. Changes in BOD and COD throughout the 20-day biotreatment test (means of BOD triplicates and of COD duplicates with standard deviation bars).

The biodegradability of the ozonated column effluent was tested by incubating the effluent over a 20-day period throughout which the COD and BOD of the flasks were monitored. FIG. 8 shows the measurements taken after 0, 5, 10, 15, and 20 days. The results indicated an increase of BOD from 0 to 4.2 mg/L during the first 10 days and leveling off over the remaining. The measured COD exhibited a complimentary curve showing a decrease in COD from 7.0 mg/L to 3.1 mg/L over the first 10 days and a constant level afterward. These results suggested that biodegradable organic compounds in the effluent were biodegraded over the first 10 days. The BOD curve was fitted with first-order kinetics using the least-square method with a first-order rate constant $k_0$=0.243 day$^{-1}$ and an ultimate BOD $L_0$=4.25 mg/L. The obtained value of $k_0$ approximates closely that of domestic wastewater routinely treated by biological unit processes.

Figure 9:
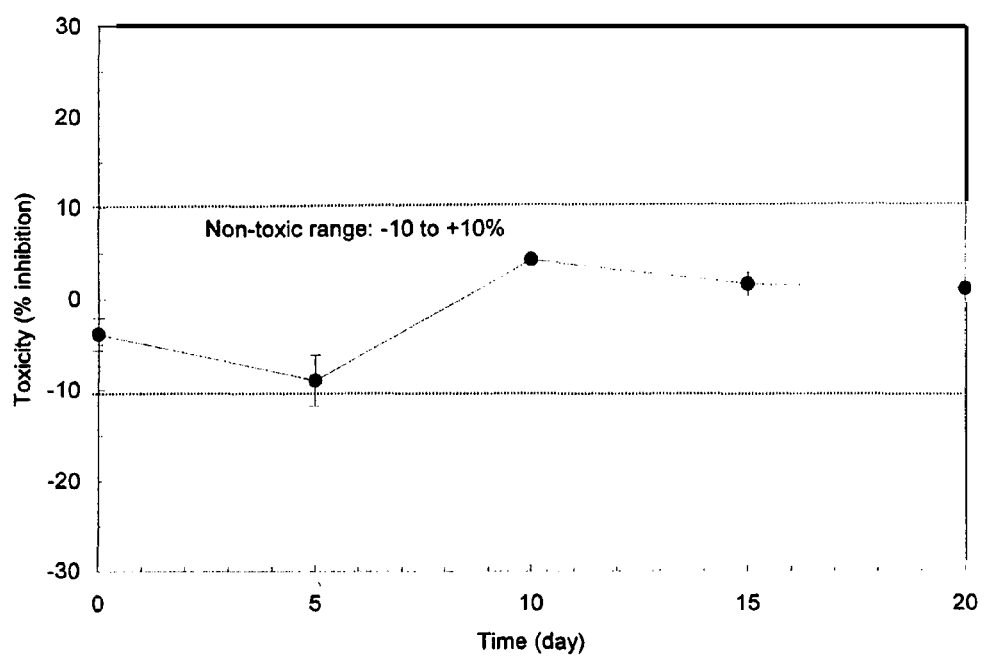
FIG. 9. Measured toxicity of the ozonated column effluent throughout the 20-day biotreatment test (means of duplicates with standard deviation bars).

The acute aqueous toxicity during the 20-day incubation period was also monitored using a standard effluent toxicity test (HACH, 1988-1995b). FIG. 9 shows the percentage inhibition value (% inhibition) of the incubated samples over the same intervals. The measurements registered inhibition values within ±10% that was within the nontoxic range of the method. This means that the effluent was nontoxic to the receiving *E-Coli* bacteria, and that the effluent contained biodegradable intermediates and byproducts, including biodegradation products, which possessed no acute toxic effects to the bacteria.

Figure 10:
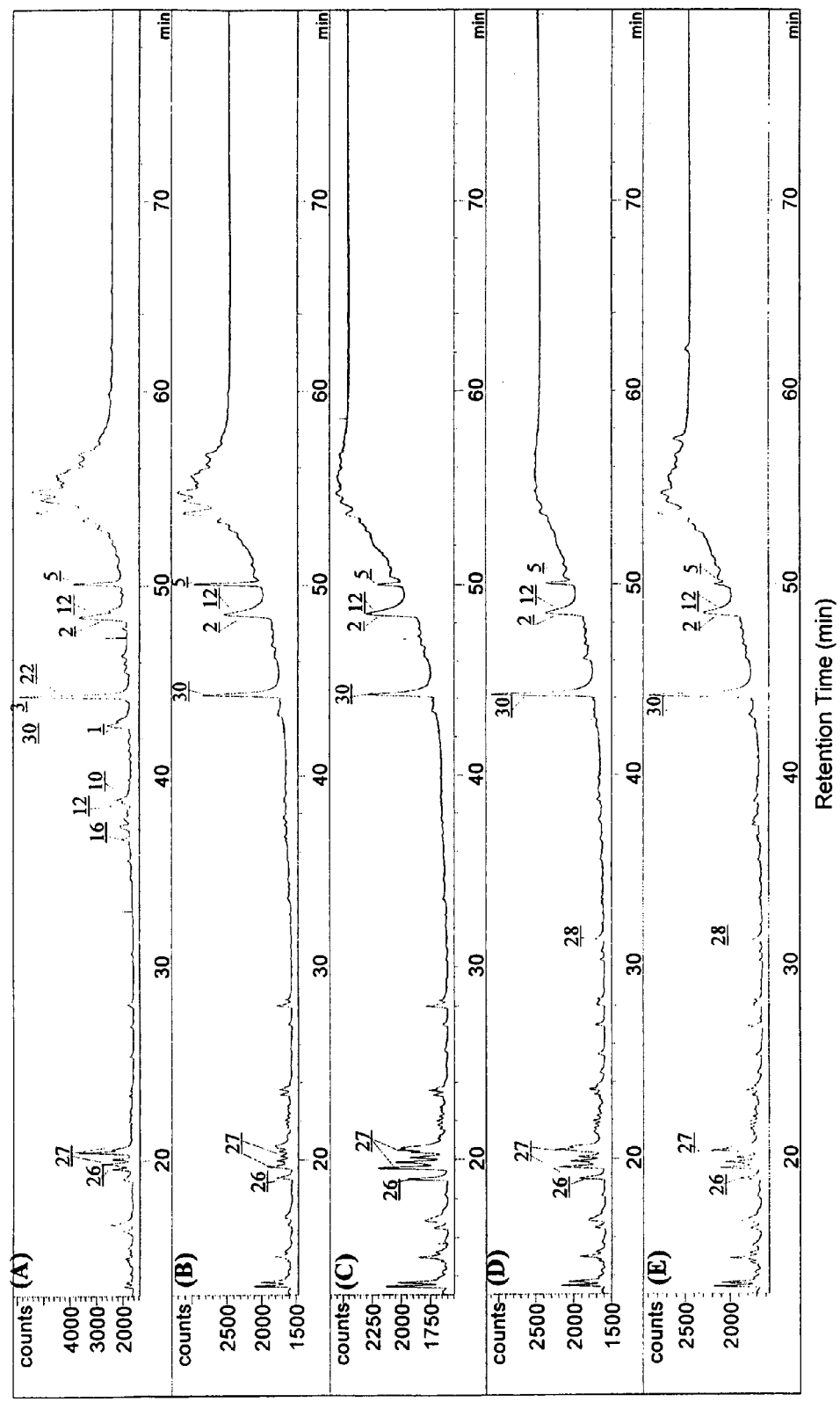
FIG. 10. Intermediates and products identified at different stages of the 20-day biotreatment test (on the ozonated column effluent): (a) prior to biotreatment; (b) after 5-day biotreatment; (c) after 10-day biotreatment; (d) after 15-day biotreatment; and (e) after 20-day biotreatment.
Identified: 1-pyrene, 2-4,5-phenanthrenedialdehyde, 3-2,2', 6,6'-biphenyltetraaldehyde, 5-benzylbutyl phthalate, 10-xanthone, 12-dibutyl phthalate, 16-hexadecanoic acid, 22-docosane, 26-unknown (m/z=154), 27-unknown (m/z=139), 28-phosphoric acid tributyl ester, and 30-biological culture (m/z=226).

Concurrent to measurements of COD, BOD, and toxicity was the GC/FID/MS identification of various intermediates and byproducts present in the flask over the same incubation period. FIG. 10 shows compounds found after 0, 5, 10, 15, and 20 days of incubation. The changes of speciation in the incubated effluent are more clearly tracked by Table A-III. The disappearance of 11 intermediates, including species 1, 3, 7, 8, 10, 13, 15, 16, 19, 21, and 22, during the first 5 days of incubation was most notable. Dissolved parent compound pyrene (1) and intermediates dialdehyde (2), tetraaldehyde (3), and other benzenedicarboxylic acids either disappeared or decreased in concentrations over the incubation period. The significant disappearance of many intermediates in the first 5 days is consistent with the much more rapid changes in BOD and COD during the initial period. After 5 days, virtually all other compounds remained detectable throughout the incubation, which signaled that these compounds could not be further biodegraded, consistent with relatively mild changes in BOD and COD. Also detected after 15 and 20 days was the phosphoric acid tributyl ester with a structure similar to high-energy phosphoanhydride bonds, which indicated that biosynthesis of ATP might have occurred along with the biodegradation processes.

Oxidant Balance for Column Ozonation

To determine the efficacy of ozone treatment, COD contents in a pyrene-packed column and in the effluent before and after ozonation were measured to establish a COD balance. In this experiment, the column was packed with glass beads and 0.147 g pyrene that amounted to a total demand of 432 mg $O_2$ as determined by COD test. Ozonated water was eluted through the column at 44 mL/min over 4 hours with a total throughput of 10.5 L. Influent and effluent $O_3$ concentrations were frequently measured at 5.05 mg/L and 0.0 mg/L, respectively; major parent and intermediate compounds, i.e., pyrene, 4,5-phenanthrenedialdehyde, and 2,2',6,6'-biphenyltetraaldehyde, in the effluent and in the column before and after ozonation were quantified. The results are shown in Table A-IV.

The total amount of $O_3$ consumed in this 4-hr experiment was 1.1 mmol or 53.0 mg (i.e., 5.05 mg/L×10.5 L), which would mineralize up to 0.09 mmol or 18.1 mg pyrene according to this stoichiometric equation: $C_{16}H_{10}+12.3\ O_3=16\ CO_2+5\ H_2O$. The amount of $O_3$ consumed could reduce the COD of the system by 18 to 53 mg of $O_2$ demand depending on the number of oxygen atoms of $O_3$ involved in the oxidation. The total amount of pyrene degraded in this experiment was 73.8 mg or 0.365 mmol. The mole ratio of consumed ozone to consumed pyrene was 1.1/0.365=3.3; thus, three moles of ozone were consumed for each mole of pyrene degraded. This observed ratio of 3.3 is clearly lower than that of 12.3 theoretically required for the complete mineralization of pyrene. Thus, significant amounts of intermediates and byproducts would be expected either in the effluent or as residuals in the column, which were indeed observed and evidenced by the higher measured COD due to intermediates in the effluent.

The COD measurements of Table A-IV also indicated a reduction of COD in the system (column residual plus effluent) by 36 mg $O_2$. This value lies well within 18 to 53 mg $O_2$ afforded by $O_3$ over the experiment duration. This means that the supplied $O_3$ was primarily consumed in converting parent pyrene to intermediates thereby reducing system COD, and that $O_3$ had not been wasted in decomposing via hydrolysis.

From the viewpoint of applying biological treatment following ozonation, it is desirable to have a lower ratio in consumed ozone to consumed pyrene but higher COD and BOD values in the effluent. Such a system will chemically pre-treat the largely insoluble pyrene to dissolved intermediates that are accessible and effectively biodegraded. It appears that an ozonated column pretreatment system can be better tuned to produce more intermediates for a sequential chemical-biological treatment system than a batch reactor that rely more on $O_3$ to mineralize intermediates.

Conclusions

This example examined the feasibility of an integrated chemical-biological system for the treatment of highly recalcitrant pyrene. The refractory nature of pyrene was thought at least in part due to its low solubility that limited access by microbes. Despite limited water solubility, pyrene can be made more soluble if one or more of its fused rings were hydroxylated with hydroxyl group (—OH) or cleaved with aldehyde group (—CHO), i.e., pyrene can be transformed into more soluble derivatives by reaction with OH. resulting in hydroxylation or with $O_3$ resulting in ring cleavage. Whereas in a batch reactor $O_3$ and its radical oxidants are capable of mineralizing pyrene and its derivatives, a column ozonation system makes more effective use of $O_3$ by generating more oxidation intermediates that can be subsequently biodegraded. This is evident from that the column effluent contained 4 times as much COD and 90% of which was biodegraded with 10 days. Mechanistically, the degradation of pyrene under ozonation was found, as supported by identified intermediates and byproducts, to proceed via initial ring cleavage by $O_3$ at the 4,5- and 9,10-bonds and continued oxidation by $O_3$ and OH. For otherwise scantly accessible pyrene, the combined chemical-biological treatment scheme appears to promote efficient use of chemical oxidant in pretreatment and effective biodegradation of the nontoxic, abundant, biodegradable intermediates.

Example B

Degradation of benzo[a]pyrene

This example focuses on an integrated treatment of benzo[a]pyrene involving sequential chemical oxidation and biological degradation. The objectives are to: 1) provide mechanistic details in the ozone-mediated degradation of benzo[a]pyrene in the aqueous phase, 2) test the biodegradability of resultant intermediates, and 3) test the feasibility for the coupled chemical-biological treatment of the 5-ring PAH. Batch and packed column reactors were used to examine the degradation pathways of benzo[a]pyrene subject to ozonation in the aqueous phase. After different ozonation times, samples containing reaction intermediates and byproducts from both reactors were collected, identified for organic contents, and further biologically inoculated to determine their biodegradability. The $O_3$-pretreated samples were incubated for 5, 10, 15, and 20 days; afterward biochemical oxygen demand (BOD), chemical oxygen demand (COD), and E-Coli toxicity tests were conducted along with qualitative and quantitative determinations of benzo[a]pyrene, intermediates, and reaction products by GC/FID and GC/MS methods. Prevalent intermediates identified at different stages included ring-opened aldehydes, phthalic derivatives, and aliphatics. The degradation of benzo[a]pyrene is primarily initiated via $O_3$-mediated ring-opening, followed by $O_3$ and hydroxyl radical fragmentation, and ultimately brought to complete mineralization primarily via hydroxyl radicals. Intermediates formed during chemical oxidation were biodegradable with a measured first-order rate constant ($k_0$) of 0.18 $day^{-1}$. The integrated chemical-biological system seems feasible for treating recalcitrant compounds, while pretreatment by chemical oxidation appears useful in promoting soluble intermediates from otherwise highly insoluble, biologically inaccessible benzo[a]pyrene.

Materials and Methods

Descriptions of sections on Chemicals, Analytical Methods and Equipment, and Reactors and Procedures were identical to Example A. Only deviations from Example A are highlighted here. Benzo[a]pyrene (BaP) (98%, Aldrich Chemical Co.) in place of pyrene was used and purified as described. A typical sample size for analysis is 150 ml and the storage temperature awaiting analysis −12° C. With the same GC/MS system, a split ratio of 5:1, solvent delay at 6 min, and scan range from m/z 15 to m/z 500 at 1.4 scan/s were used. Comparison of parent compound structure and interpretation of mass spectra of the intermediates from ion fragmentation information were performed particularly for the identification of key intermediates 7-propanal-8-methylpyrene, 7-ethyl-8-ethanalpyrene, and 4-methyl-5-hydroxylchrysene. Reactor systems (FIG. 1) were identical to ones previously used except that 0.15 g benzo[a]pyrene was prepared and loaded into the packed column reactor. Samples during batch reaction were taken at 2, 10, 20, 30, and 50 min. Sample BOD and toxicity were determined in triplicates and duplicates, respectively. Previous analytical efforts for pyrene were redirected toward benzo[a]pyrene.

Results and Discussion

The degradation pathway, biodegradability of intermediates, and oxidant balance during ozonation of BaP will be addressed in turn.

Degradation Pathways of Ozonated Benzo[a]pyrene

COD measurements were made for three solutions: 1) a saturated aqueous solution of BaP, 2) the solution after ozonation of a batch of excess BaP suspension (0.150 g/1.7 L), and 3) the effluent of a column packed with excess BaP solid (0.149 g) and glass beads (7.5 in. in bed-length). The saturated BaP solution was prepared by allowing excess BaP solid to reach dissolution equilibrium in water overnight followed by removal of the excess solid using a 0.45-μm filter. The ozonated batch solution was obtained after 50 min of ozonation and filtered, while the column effluent was collected from the packed column fed with an ozonated water over a 4-hr period and filtered. Table B-I shows the results COD measurements of all solutions and one $BOD_5$ measurement for the column effluent. The saturated solution of BaP, due to its very limited aqueous solubility, registered a negligible COD value compared to that of the ozonated batch solution or the ozonated column effluent. In both the batch and column solutions, much higher COD values were measured after ozonation, which indicated dissolution of daughter compounds of BaP into the aqueous phase as a result of ozonation. A relatively biochemical oxygen demand high $BOD_5$-to-COD ratio of 0.43 was observed for the column effluent, which suggested the intermediates were susceptible to biodegradation, a point of further discussion later.

Figure 11:
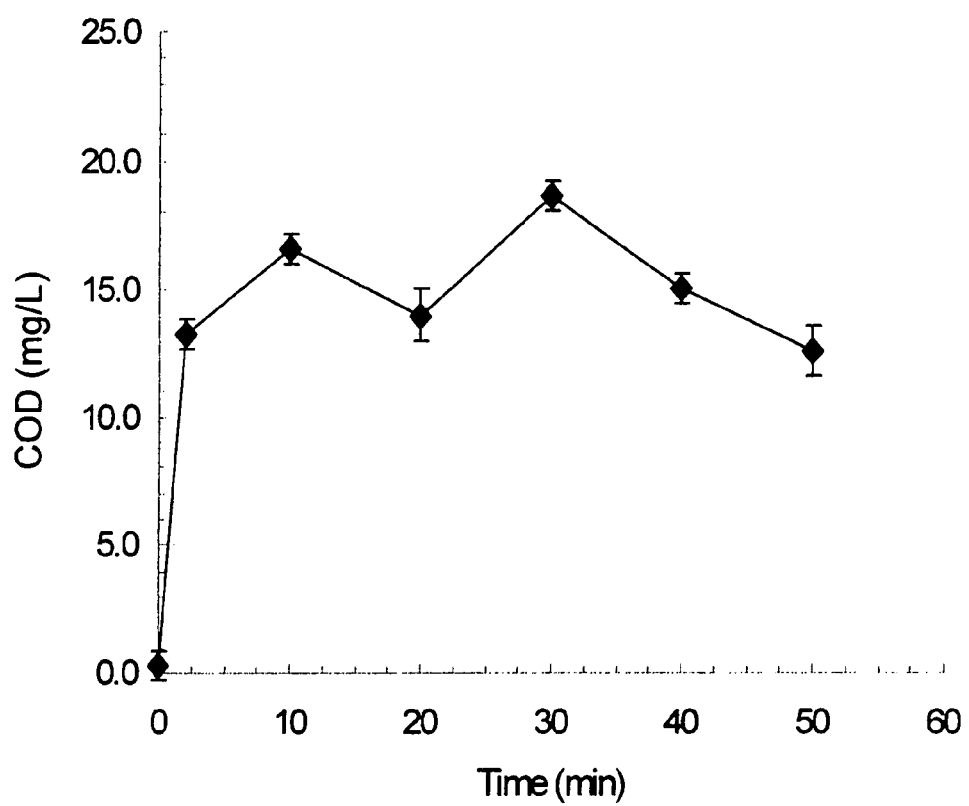
FIG. 11. Measured COD of the ozonated batch effluent throughout 50 min. of ozonation time, mean±standard deviation of triplicates shown.

The COD values in the batch solution were relatively stable at about 15 mg/L during the 50-min ozonation period, as shown in FIG. 11. This seemingly steady-state level of COD could be indicative of the relatively constant quantity of intermediates that were continually added to the aqueous phase via oxidation of the parent BaP solid, as well as continually being removed via further mineralization by ozone.

The aqueous intermediates after ozonation were identified and quantified by GC/MS techniques. Over sixty compounds were identified as intermediates and products in this example. Table B-II lists the identified compounds in the order of increasing retention time in the GC column, and labels them numerically in the like order. Among the myriad of those identified are five intermediates including ring-opened aldehyde (28), phthalic derivatives (29 and 38), and alkane/alkene (34, 12). These products would likely abound at different stages of ozonation, i.e., with the aldehyde and acid more prevalent in the initial stage of ozonation and the alkene and alkane the later stage.

Figure 12:
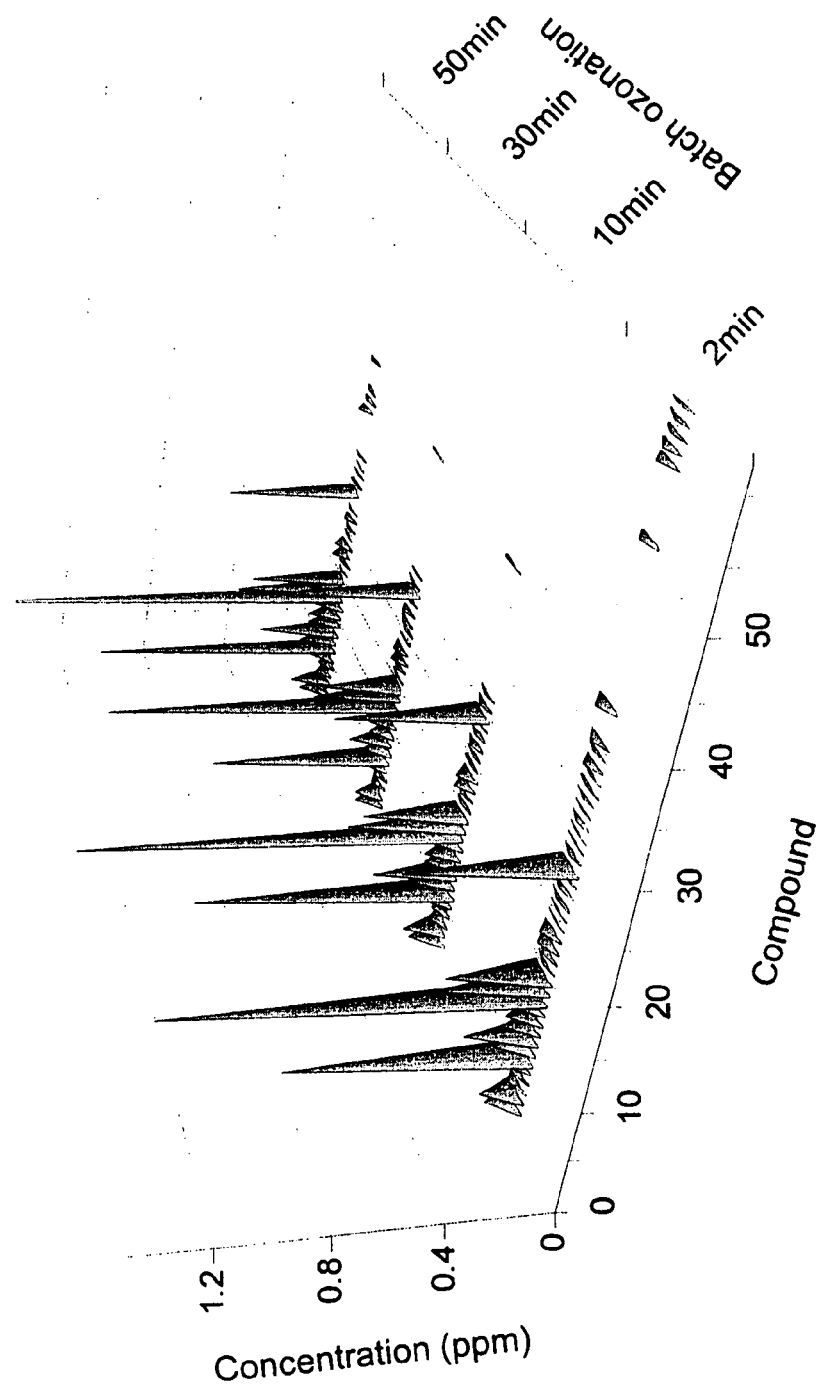
FIG. 12. Intermediates and products identified and quantified in a batch reactor containing a benzo[a]pyrene suspension after being ozonated for (a) 2 min; (b) 10 min; (c) 30 min; and (d) 50 min. (All species are listed in Table B-II.)

FIG. 12 shows the identified, quantified species during 50-min ozonation of a BaP batch suspension. Salient of this figure is the largely absence, particularly beyond initial minutes, of compounds with longer column retention time (e.g., >20 min; or compound 27 or higher) that are typical of intermediates found in the early stages of ozonation or shortly after ring-opening of BaP. The absence is indicative of further oxidation of early intermediates such as phthalic acids into other products. Furthermore, that those compounds with shorter column retention times (e.g., compound 26 and lower) remained relatively constant over the ozonation period was consistent with the relatively stable COD measurements of FIG. 11 shown for the same period. Long-chain aliphatic alkanes such as compounds 58 to 61 eventually disappeared with ozonation treatment longer than 2 minutes, as they were likely fragmented by secondary free-radical oxidants such as the OH. Therefore, FIG. 12 indicates a steady-state conversion of the excess BaP solid into more water-soluble intermediates such as aldehydes and acids that are rapidly converted to various alkane and alkene mainly by radical reactions discussed below. That, the reaction rates of oxidants (both $O_3$ and secondary oxidant OH.) with the earlier intermediates such as oxygenated compounds being relatively faster than those with later intermediates such as alkenes and alkanes, would explain the absence of the former intermediates but an abundance of the latter during the seemingly steady-state mineralization.

Figure 13A:
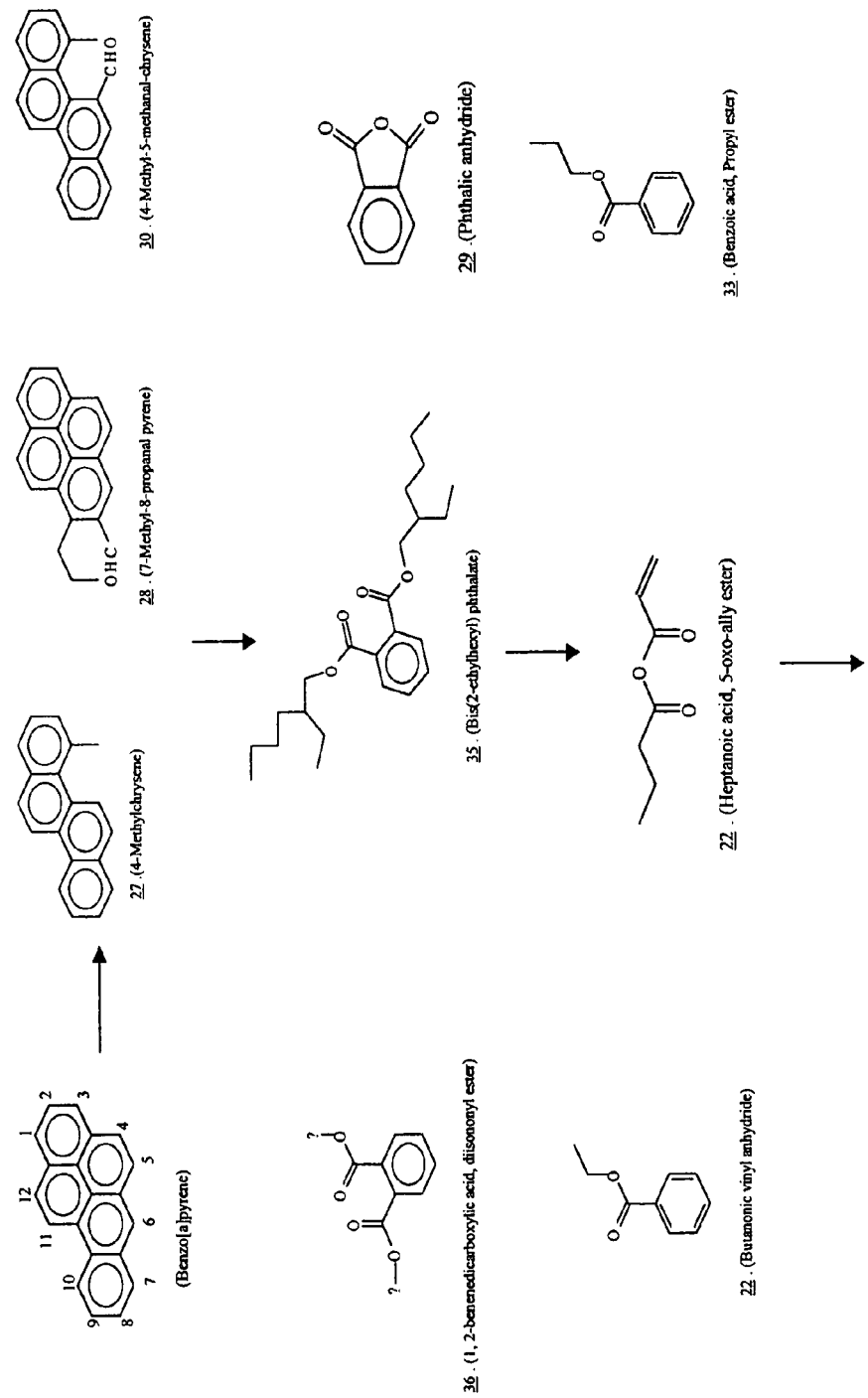
FIGS. 13a to 13d. Degradation pathways of ozonated benzo[a]pyrene: (a) overall pathways showing major identified intermediates and products; (b) proposed mechanistic steps in the formation of oxygenated intermediates; and (c) proposed mechanistic steps in the formation of aliphatic products.
Figure 13B:
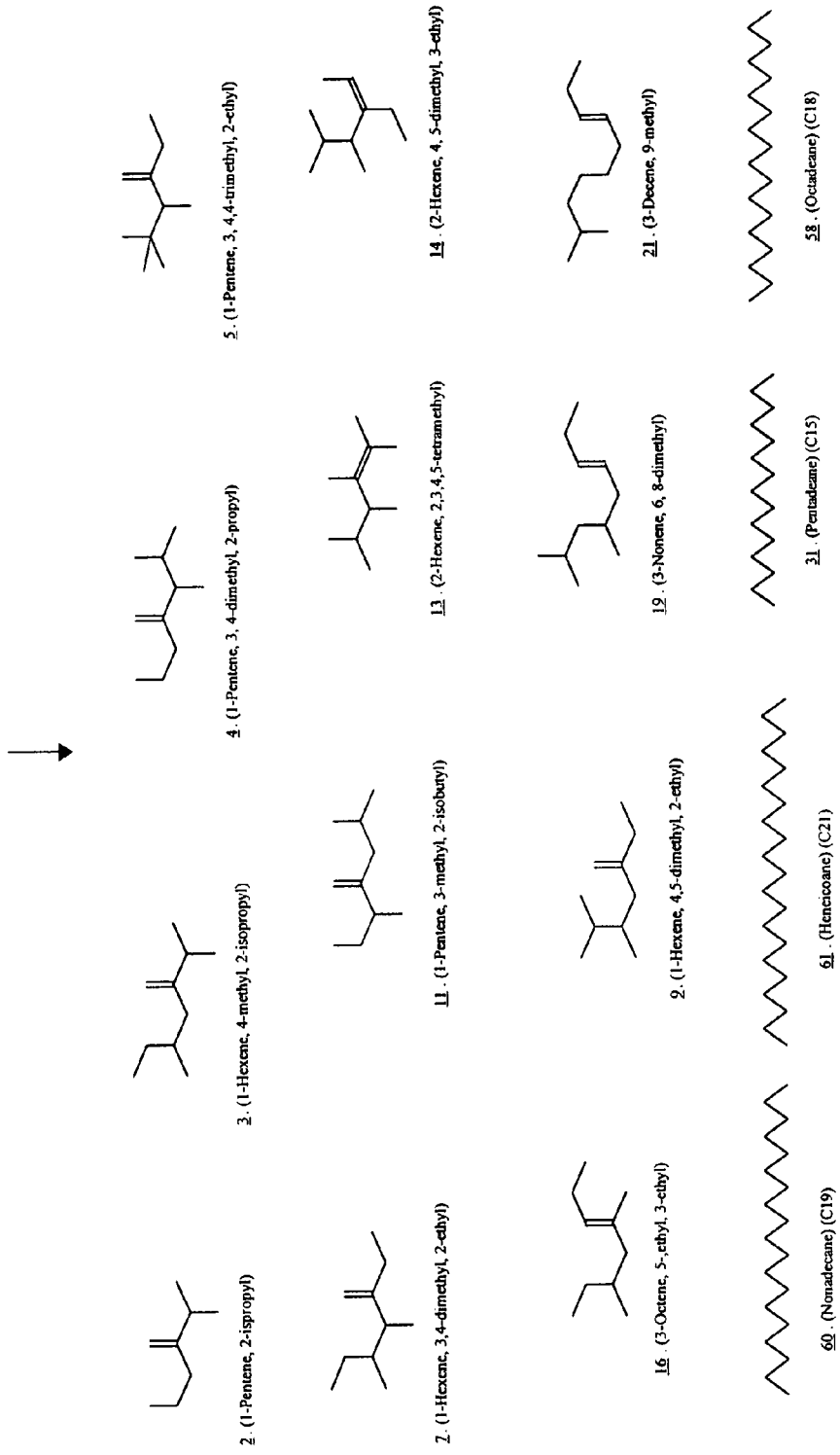

FIGS. 13a and 13b outline (with the top of 13b starting at the bottom of 13a) a general degradation pathway of BaP subject to ozonation in the aqueous phase based on actual identified compounds. In general, the earlier reaction stage is populated with aromatic, oxygenated intermediates, while the latter stage with alkenes and alkanes. In more details, FIGS. 13b and 13c proposed mechanistic steps leading to the formation of various oxygenated intermediates (Sequences I to IV) and aliphatic compounds (Sequences V and VI), respectively. The underlined, numerated species were identified whereas the curly-bracketed ones were proposed intermediates. As shown in FIGS. 13a and 13b, the degradation was initiated by electrophilic attack of $O_3$ on one of the electron-rich conjugate rings of the BaP molecule resulting in the formation ring-opening products 27 and aldehydes 28 and 30. Subsequent reactions of intermediates with $O_3$ or its concomitant oxygenated radicals (e.g., OH., $O_2.^-$, $O_3.^-$) resulted in additional oxygenated intermediates such as 36, 35, 29, 22, 32, 33. The production of alkenes (e.g., compounds 2, 3, 4, 5, 6, 7, 9, 11, 13, 14, 16, 17, 19, and 21) and long-chain aliphatic alkanes (e.g., compounds 60, 61, 31, 58) was attributed to oxidation reactions prompted by $O_3$, OH., and other free radicals. It should be noted that the formation of secondary radical oxidants including $O_2.^-$, $O_3.^-$, OH. as well as $H_2O_2$ resulting from hydrolysis of $O_3$ has been extensively documented.

Figure 13C:
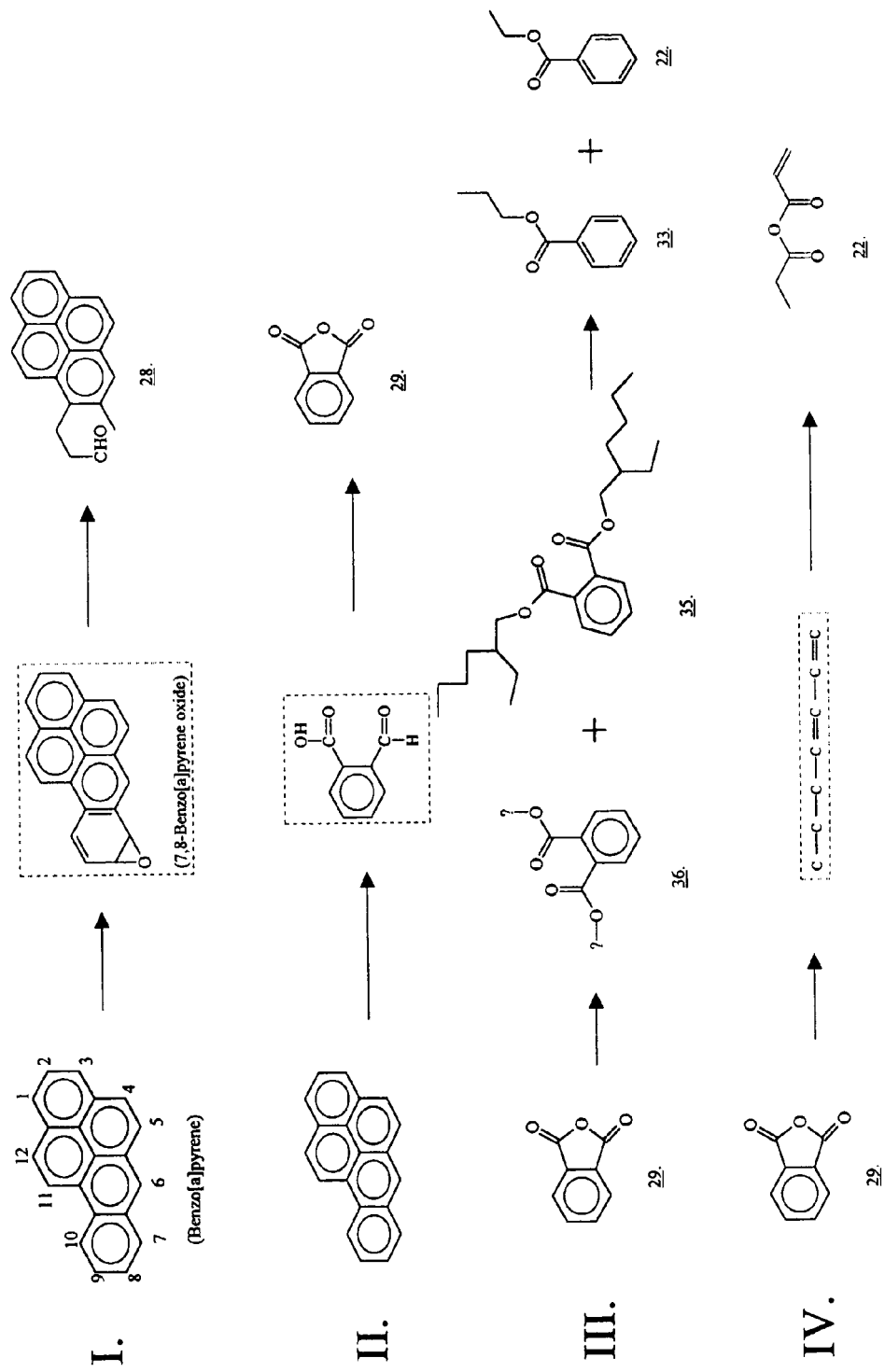

FIGS. 13b and c explain the formation of observed products (species numbers underlined) via proposed intermediates (shown in curly brackets), many of which have been reported as plausible elsewhere and their reaction steps are cited with italicized numerals. Sequence I of FIG. 13c shows upon ozonation of BaP the formation of 7-methyl-8-prypanal-pyrene (28) via epoxidation at 7,8-bond, followed by bond breakage resulting the aldehyde, followed by further epoxidation at the 9,10-position resulting in the dihydrodiol that further reacts with $O_3$ and with loss of $H_2O_2$ ultimately leads to compound 28. The 4,5- and 7,8-bond cleavage products (30 and 28, respectively) were found in this example. These bonds have lowest localization energy and thus are sites most susceptible to epoxide formation.

Sequence II produces phthalic anhydride (29) via 1,6-quinione of benzeno[a]pyrene and 1,2-anthraquinonedicarboxylic acid intermediates. Further ozonation of intermediates results in the primary ozonide structure and secondary peroxidic intermediates, phthaladehydic acid, then ultimately phthalic anhydride 29.

Sequence III suggests that continued ozonation of phthalic anhydride 29 leads to identified intermediates 35 and 36 via phthalic acid and its radical that subsequently recombines with other alkyl radicals. The breakage of fragile R—O bonds in 35 and 36 further leads to 32 and 33. Ozonation of phthalic anhydride 29 can also cleave the molecule at the 1,2-position, resulting in a primary ozonide structure. Alternatively, Sequence IV suggested continued ozonation of phthalic anhydride leads to a primary ozonide and peroxidic intermediates (as in Sequence III), followed by loss of $-CO_2$ and $-CO$ groups resulting in the formation of 1,3-diene intermediate, which upon renewed $O_3$ attacks as shown leads to the formation of ester 22.

Figure 13D:
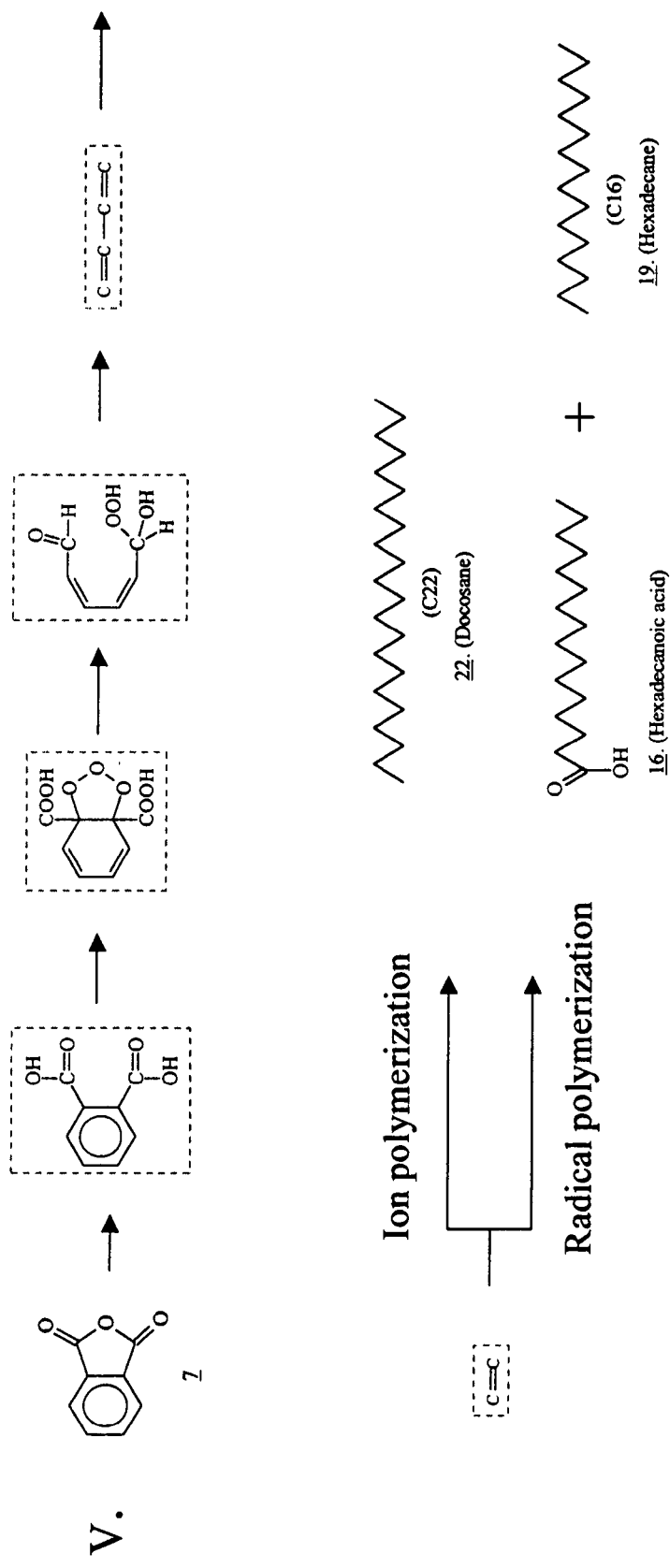

Sequence V of FIG. 13*d* shows ring-opening products as phthalic acid derivatives, which upon OH. attack form alkene radicals. These radicals undergo additional free-radical reactions with other alkene fragments, and their eventual radical recombinations lead to alkene products such as 7 and 19. Appearing prima facie puzzling was an abundance of alkenes and alkanes observed amid the panoply of oxidized products in the ozonated, highly oxidizing environment, which might have suggested them products of reduction reactions. Similar products were observed in Examples A for the ozonation of pyrene. Other alkanes, alkenes, and related compounds were previously observed as products from ozonation of hydrocarbons as well. Nonanal and nonanoic containing straight chain carbons were reported as oxidation products from ozonation of PAHs (20, 21). Decane, decene, and epicosane were obtained from ozonation of 1-dodecene (38). These aliphatic compounds were attributed to free radical mechanisms at work. It is well accepted that as $O_3$ undergoes hydrolysis during ozonation, both $O_3$ and OH. are available for reactions with species in the reaction medium. Sequence VI proposes a polymerization pathway for the formation of long-chain alkanes by the actions of $O_3$ and OH. radical. As shown, it is initiated by ring opening of intermediates such as 29, followed by fragmentation into ethene and diene that undergo ionic and/or radical polymerization in the presence of OH., resulting in identified alkanes such as tridecane (34) and henicosane (61).

An observation supporting the involvement of free radicals was the disappearance of these long-chain alkanes if the effluent was subject to prolonged ozone hydrolysis. Long-chain alkanes are characteristically resistant to electrophilic attack by $O_3$ yet susceptive to degradation by OH. produced via $O_3$ hydrolysis. Simpler short-chain polar aliphatic compounds were expected but not found in the reaction mixture; their absence was attributed to analytical extraction and preparation procedures that failed to retain compounds with less than six carbons.

As already mentioned, the presence of organic co-solvent and the concentration of $O_3$ play an important role in determining product formation and distribution.

In summary, this example demonstrates that the degradation mechanism of BaP is, as reconstructed based on about 60 observed intermediates and products, initiated primarily via ring-opening by $O_3$ at the onset, continued in fragmentation by both $O_3$ and OH., and ultimately brought to complete mineralization primarily via OH. radicals.

Biodegradation of Intermediates from Ozonated Benzo[a] pyrene

Figure 14:
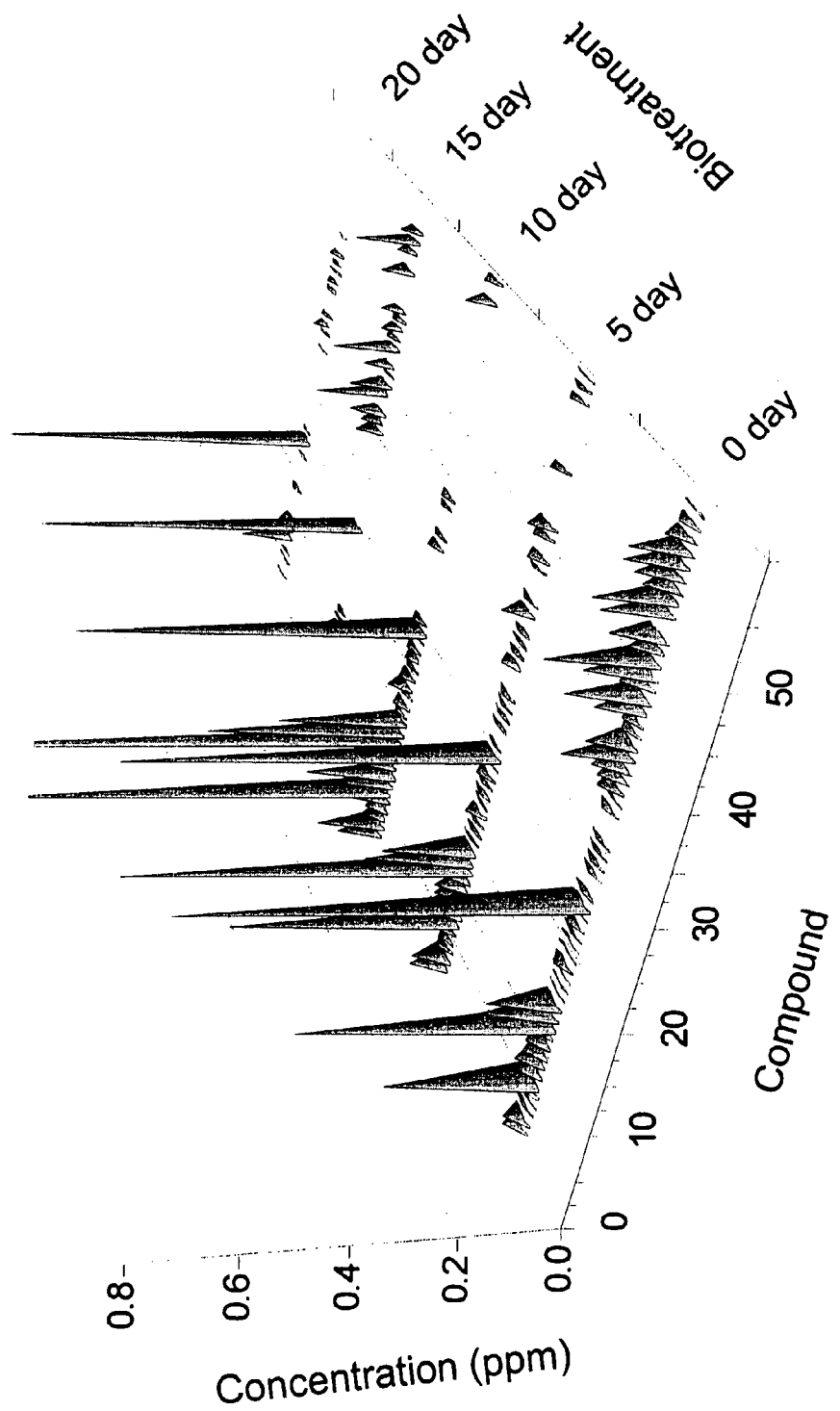
FIG. 14. Biodegradation intermediates and products identified and quantified during a 20-day biological incubation of a pretreated effluent obtained from a benzo[a]pyrene-packed column fed with ozone-laden water. (a) Before incubation; (b) after 5-day incubation; (c) after 10-day incubation; (d) after 15-day incubation; and (e) after 20-day incubation. (All species are listed in Table B-II.)

The biodegradability of intermediates resulting from ozonation of BaP was tested by incubating the ozonated column effluent for a 20-day period throughout which the intermediates were qualitatively and quantitatively determined. The effluent was collected from a BaP-packed column fed with ozonated water. The up-flow influent water contained 4.77 mg/L $O_3$ while the effluent none, indicating that complete consumption of $O_3$ occurred in the column. FIG. 14 identifies intermediates and byproducts present in the flask throughout the incubation period at 0, 5, 10, 15, and 20 days. At day-0, the speciation in the column effluent already differs from that in the ozonated batch solution. The column effluent contains a larger presence of compounds 30 and higher (i.e., early-stage intermediates with longer GC-column retention times), which are attributed to the flow-through column configuration. A batch reactor readily subjects the intermediates from pyrene to continual $O_3$ attack and further degradation, whereas the column reactor allows the intermediates to be eluted from the $O_3$-rich area, i.e., the reactive zone. Thus, the column effluent contained a larger abundance of intermediates and the contents of the partially treated intermediates were chosen for test of their biodegradability.

FIG. 14 appears to show that the early products of ozonation (e.g., Compounds 25 or higher) either decreased over the incubation period or disappeared, whereas the later products such as alkenes 5 and 7 appeared to increase from 0 to 10 days but decrease or disappear by day-20. Overall, most intermediates and by-products in the column effluent either significantly decreased or disappeared by the end of the 20-day incubation period. It should be noted that compound 24, decafluorobiphenyl, was the added internal standard for the GC analytical procedures. Therefore, the results seem to suggest that ozonation makes available from otherwise highly insoluble, inaccessible BaP a plethora of water-soluble intermediates that are biodegradable.

Figure 15A:
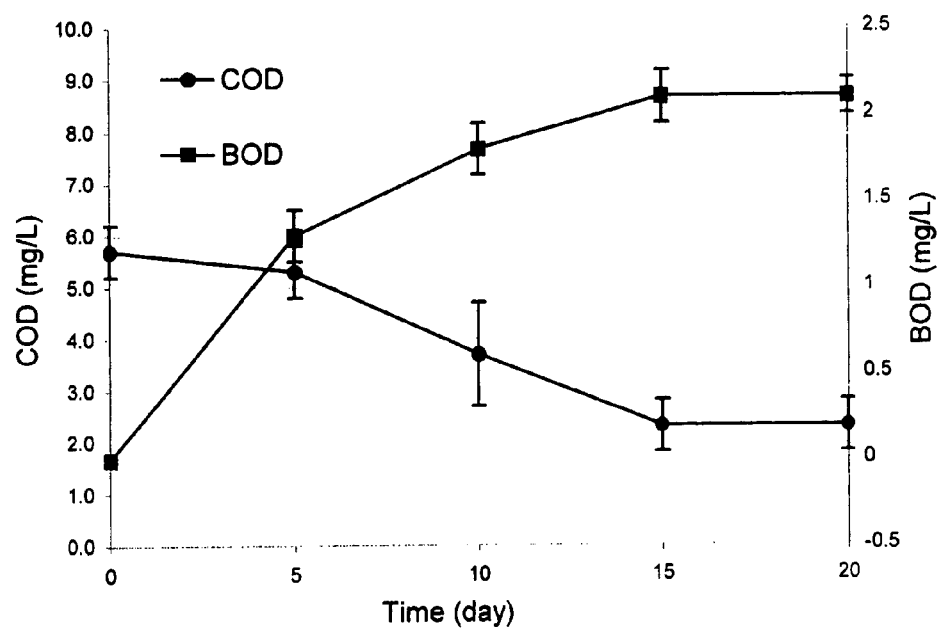
FIG. 15. (a) BOD and COD changes during the 20-day biological incubation of the ozone-pretreated column effluent (as in FIG. 5); shown are mean and standard deviation of triplicate COD, and mean and range of duplicate BOD. (b) Toxicity assessed during the 20-day biological incubation of the ozone-pretreated column effluent (as in FIG. 5), with mean and range of duplicates shown.

Concurrent to GC identification and quantification procedures during the incubation period, measurements of COD, BOD, and toxicity were made. FIG. 15*a* shows the BOD and COD changes after 0, 5, 10, 15, and 20 days. The results indicated an increase of BOD from 0 to and leveling at 2 mg/L over the 20-day period. The measured COD exhibited a complimentary curve showing a decrease in COD from 5.5 mg/L to 2.2 mg/L over the same period. These results suggested that biodegradable organic compounds in the ozonated column effluent were biodegraded over the incubation period, consistent with the quantification results of GC of FIG. 14. The BOD curve was fitted with first-order kinetics using the least-square method with a first-order rate constant $k_0 = 0.18$ day$^{-1}$ and an ultimate BOD $L_0 = 2.2$ mg/L. The obtained value of $k_0$ approximates that of domestic wastewater routinely treated by biological unit processes.

Figure 15B:
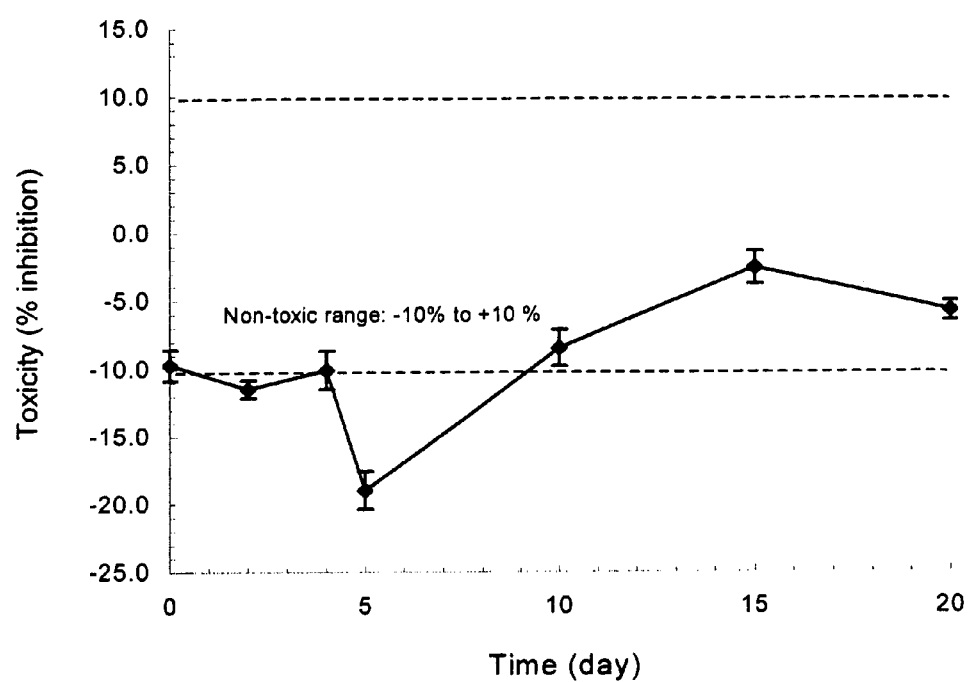

The acute aqueous toxicity during the 20-day incubation period was also monitored using a standard effluent toxicity test described previously. FIG. 15*b* shows the percentage inhibition value (% inhibition) of the incubated samples over the same period at 0, 3, 4, 5, 10, 15, and 20 days. The heightened acute toxicity at day 5 (−19%) appeared to be an outlier as it was not supported by speciation and quantification results of FIG. 14. In general, the measurements registered inhibition values mostly within ±10% that was within the nontoxic range of the method. This means that the effluent was nontoxic to the receiving *E-Coli* bacteria, and that the effluent contained biodegradable intermediates and byproducts, including biodegradation products, which possessed no acute toxic effects to the bacteria.

The integrated chemical-biological system being investigated is useful for treating highly recalcitrant BaP, the refractory nature of which has been thought at least in part due to its low solubility that limited access by microbes. The present process rendered BaP more soluble and thus biologically accessible by cleaving one or more of the fused rings resulting in intermediates containing aldehyde (—CHO) or carboxylic (—COOH) groups, i.e., BaP was transformed into water-soluble, biodegradable derivatives by reaction with $O_3$ and secondary radical oxidants.

Oxidant Balance for Column Ozonation

To determine the efficacy of ozone treatment, COD contents in a BaP-packed column and in the effluent before and after ozonation were measured to establish a mass balance. In this experiment, the column was packed with glass beads and 150 mg BaP that amounted to a total demand of 436 mg $O_2$ as determined by COD test. Ozonated water was eluted through the column at 44 mL/min for 4 hours with a total throughput of 9.75 L. Influent and effluent $O_3$ concentrations were frequently measured at 4.77 mg/L and 0.0 mg/L, respectively. Parent compound in the column was measured before and after ozonation, and none was found in the effluent. The COD contents in the column were measured before and after ozonation, as well as that in the effluent. The results are shown in Table B-III.

The total amount of $O_3$ consumed in this 4-hr experiment was 0.97 mmol or 46.5 mg (i.e., 4.77 mg/L×9.75 L), which would mineralize up to 0.063 mmol or 15.9 mg BaP according to this stoichiometric equation: $C_{20}H_{12}+15.3\ O_3=20\ CO_2+6\ H_2O$. The amount of $O_3$ consumed could reduce the total COD of the system by 15.5 to 46.6 mg of $O_2$ demand depending on the number of oxygen atoms of $O_3$ involved in the oxidation. The total amount of BaP degraded in this experiment was 32.5 mg or 0.128 mmol. The mole ratio of consumed ozone to consumed pyrene was 0.97/0.128=7.6; thus, 7.6 moles of ozone were consumed for each mole of BaP degraded. This observed ratio of 7.6 is lower than that of 15.3 theoretically required for the complete mineralization of BaP. Thus, significant amounts of intermediates and byproducts would be expected either in the effluent or as residuals in the column, which were indeed observed and evidenced by the higher measured COD due to intermediates in the effluent. The larger equivalents of $O_3$ consumed per BaP degraded must be recognized with the fact that many observed compounds were products evidently from repeated attacks by $O_3$ or its secondary radicals, which inevitably required higher than unit molar equivalent of $O_3$.

The COD measurements of Table B-III also indicated a reduction of COD in the system (column residual plus effluent) by 36 mg $O_2$. This value lies well within 18 to 53 mg $O_2$ afforded by $O_3$ over the experiment duration. This means that the supplied $O_3$ was primarily consumed in converting parent BaP to intermediates thereby reducing the system COD, although decomposing of $O_3$ via hydrolysis was also occurring.

From the viewpoint of applying biological treatment following ozonation, it is desirable to have a lower ratio in consumed ozone to consumed BaP but higher COD and BOD values in the effluent. Such a system will chemically pre-treat the largely insoluble BaP into dissolved intermediates that are accessible and biodegradable. Whereas $O_3$ and its radical oxidants are capable of mineralizing BaP and its derivatives as in a batch reactor, the pretreatment of BaP with $O_3$ as in a flow-through system makes effective use of chemical oxidation by generating intermediates that can be subsequently biodegraded. For otherwise scantly accessible BaP solid, the combined chemical-biological treatment scheme promotes efficient use of chemical oxidant for pretreatment and viable biodegradation of the resulting nontoxic, water-soluble, biodegradable intermediates.

Example C

Degradation and Remediation of Oil Spills

Materials and Methods

The Bipolar Homogenous Solvent System

In this work example, an innovative treatment is developed for spilt oils from southern Kuwait desert that involves ozonation in a homogeneous solvent system. The solvent is constituted of miscible n-heptane and acetic acid (1:1 by volume), both of that are relatively inexpensive, environmentally benign, and biodegradable. The solvent system allows dissolution of oil in its non-polar heptane constituent, while the hydrophilic acetic acid keeps the progressively more polar intermediates and byproducts being formed from ozonation of oil in solution as the reaction continues. The n-heptane and acetic acid were chosen because of their relatively slow reaction rate with ozone ($k_{O3}[M^{-1}\ s^{-1}]$ about $10^{-3}$~1 for alkanes and $3\times10^{-5}$ for acetic acid.

The amount of oil to be employed in the bipolar solution was determined by its solubility in n-heptane and bipolar solvent. With an addition of 2.5 ml of distilled deionized water (about 5%) to a homogenous solution 50 ml of n-heptane and 50 ml of acetic acid, the solution was separated into two distinct phases: the n-heptane containing PAHs and other hydrophobic intermediates, and acetic acid phase (95% of acetic acid/5% DD water) containing the hydrophilic byproducts. In this example, about 480 mg/L of oil in the bipolar solvent was ozonated for different durations and the solution contents were analyzed accordingly. Both byproducts in the n-heptane phase and in the 95% acetic acid phase were analyzed by GC/FID, GC/FPD, and GC/MS after the separation. Ozone stability in different solvents: bipolar solvent, n-heptane, 95% acetic acid/5% DD water, and pure acetic acid were also tested by stopping after 20 minutes of ozonation and monitoring the ozone concentration immediately after.

Ozonation Reaction Kinetics in Bipolar Solvent

Ozonations were performed at room temperature (about 20° C.), and reactions were monitored over periods of 15 seconds to 3 hours. The pseudo-first order rate constants were evaluated by linear regression of all data according to the equations given below. The reaction of ozone with contaminants can be expressed as a second order reaction:

$$-dCA/dt=kCA[O_3] \quad (1)$$

where:
−dCA/dt=rate of reaction of contaminant
k=reaction rate constant
CA=concentration of contaminant
[$O_3$]=concentration of ozone In the present of excess and constant ozone concentration, the rate law for the reaction can be considered as pseudo-first order:

$$-dCA/dt=k'CA \quad (2)$$

where
−dCA/dt=rate of reaction of contaminant
k'=pseudo-first order rate constant
CA=concentration of contaminant.

Chemicals

Degraded spilt oil comes from oil lakes in the southern desert of Kuwait. N-Heptane (Fisher Scientific) of HPLC grade and acetic acid (99%, Mallinckrodt) were used as cosolvents in a batch reactor. Stock and working indigo blue solution were prepared from potassium indigo trisulfanate ($C_{16}H_7N_2O_{11}S_3K_3$, Aldrich Co.) for ozone concentration measurements per Standard Methods. Low-organic (<15 ppb as TOC), low-ion (resistivity >18 M$\epsilon$-cm), and nonpyrogenic (up to 4 log reduction with reverse osmosis pretreatment) distilled-deionized water was used in all procedures (4-stage MILL-Q Plus system, Millipore Co.). Other chemicals used in this research were of reagent grade.

Analytical Methods and Equipment

Ozone was generated by an ozone generator (Model T-816, Polymetrics Corp.) from dry and filtered air at an applied voltage of 65V an air flow rate of 2 L/min. The concentration of ozone in the bipolar solvent was determined by absorbance at 270 nm with a spectrophotometer (HP 8452 UV-Vis spectrophotometer, Hewlett Packard Co.) using a predetermined extinction coefficient of 1955 $M^{-1}$ $cm^{-1}$. This extinction coefficient was obtained by correlation with actual ozone concentrations in the bipolar solvent, which were measured by contacting 10 mL of $O_3$-saturated bipolar solvent with 50 mL of standard Indigo Blue solution in a separatory funnel, following calibration procedures at 600 nm similar to the Indigo Blue method.

Samples containing oil and intermediates in n-heptane, 95% acetic acid, and bipolar solvent were analyzed respectively using a gas chromatograph (GC). GC/FID analyses were carried out using a HP 5890 (Hewlett Packard Co.) fitted with a capillary column (DB-1 non-polar column, 60 m×0.25 mm×0.25 um, J&W Co.) and a flame ionization detector (FID). The GC/FID was interfaced and programmed with the HP Chemstation software (Hewlett Packard Co.) A 5:1 split and 1 uL sample injection were used. The chromatographic oven was held at 35° C. for 1 min then linearly increased at 5° C. per min to 300° C. with a 30 minutes hold.

Samples were analyzed with a GC (HP 6890) with a capillary column (DB-1 non-polar column, 60 m×0.25 mm×0.25 um, J&W Co.) interfaced to a mass spectrometry detector (MS) (HP6800) and programmed with the HP Chemstation software (Hewlett Packard Co.). A split ratio of 5:1, solvent delay at 10 minutes, and scan range from m/z 15 to m/z 550 at 1.4 scan/sec were used. The oven temperature was held at 35° C. for 1 min then linearly increased at 5° C. per min to 300° C. and held for 30 minutes. The HP Chemstation library (Hewlett Packard Co.) was used for tentative identification of peaks as a supplement to mass spectral and retention time characteristics. In addition, comparison of parent compound structure and interpretation of mass spectra of the intermediates from ion fragmentation were performed particularly for the identification of key intermediates.

Samples were also analyzed with a GC/FPD (HP 5890) for bulk characterization of sulfur-containing compounds. GC/FPD analyses were carried out using a HP 5890 (Hewlett Packard Co.) fitted with a capillary column (DB-1 non-polar column, 60 m×0.25 mm×0.25 um, J&W Co). The GC/FPD was interfaced and programmed with the HP Chemstation software (Hewlett Packard Co.) A 10:1 split and 1 uL sample injection were used. The chromatographic oven was held at 35° C. for 2 min then linearly increased at 4° C. per minute to 225° C. and continuing increased at 8° C. per minute to 300° C. with a 40 minutes hold.

Batch Reactor

A glass batch reactor with a working volume of 300 mL was used. Mixing in the reactor was provided by a magnetic mixer operating at 250 rpm. After preparing about 50 ml of 960 mg of oil per liter of n-heptane, 50 ml of acetic acid was added into the reactor (resulting in a 480 mg/L solution of oil in the bipolar solvent). Ozone was sparged into the reactor near the bottom through a glass dispersion tube (ACE glass Inc.) Reaction batches were stopped after 0.25, 0.5, 1, 2, 3, 4, 5, 10, 20, 40, 60, 120, and 180 minutes of ozonation. Residual ozone was removed from solution by purging with a gentle $N_2$ stream for 1 min. Samples were kept in 2-mL vials and preserved at 5° C. if necessary prior to GC analysis. Qualitative and quantitative analyses of oil and oxidized oil were performed simultaneously. All samples were concentrated by a gentle stream of $N_2$ gas to best retain the intermediates with lower molecular weights.

Results and Discussion

The oxidative degradation of different fractions of hydrocarbons by ozonation in the bipolar solvent, the reactivity of aromatic sulfur compounds in ozonated environment, and the biodegradability of ozonated oil will be discussed. All major compounds discussed are illustrated in Table C-1.

Ozonation of Saturate Factions of Spilt Oil

Figure 16:
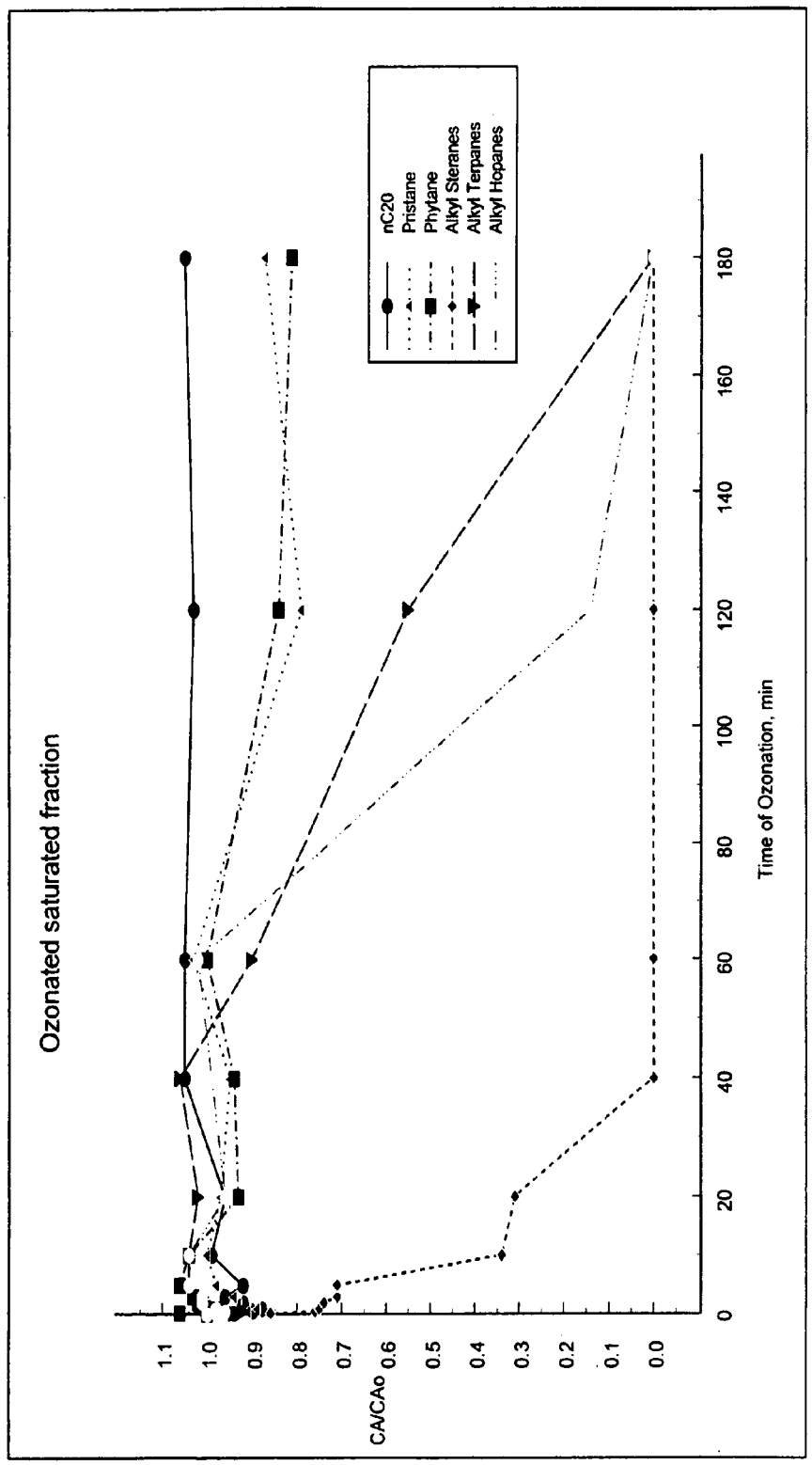
FIG. 16. A graph showing the ozonation results of various alkane and saturated ring compounds.

The saturate factions are normal, iso-paraffin (branched alkanes) and cyclic alkanes of the spilt oil. The n-icosane (about 6% estimated wt %), pristane and phytane are chosen to represent normal alkanes and branched alkanes respectably. The ozonation results of these three compounds in the bipolar solvents are shown in FIG. 16. The n-icosane was shown more resistant to ozone than pristane and phytane. The tentative estimated pseudo-first order rate constants (as shown in Table C-2) for n-icosane, pristane, and phytane in the complex mixture are $1.98 \times 10^{-3}$, $1.30 \times 10^{-2}$, and $1.78 \times 10^{-2}$ $s^{-1}$ respectively.

Cyclic alkanes with long alkylated chain were also degraded by ozonation as depicted in FIG. 16. Steranes and terpanes with four cyclic saturated rings and hopanes with five cyclic saturated rings are detected by GC/MS (about 3.0% estimated wt %). Alkyl steranes were depleted through ozonation much faster than alkyl hopanes and terpanes. The reason to choose steranes, terpanes, and hopanes to represent saturated cyclic compounds is that they are not only the common constituents in the crude oil but also very resistant to biodegradation. The length of the alkylated chain does not have significant influence on the rate of reaction with ozone in this example. The degradation of n-icosane, pristane, phytane, steranes, and hopanes during the ozonation are illustrated in FIG. 16 and the tentative estimated pseudo-first order rate constants are shown in Table C-2. It is noticed that saturated cyclics (k'=$2.57 \times 10^{-1}$ $s^{-1}$) undergo much faster ozonation than branched alkanes (k'=$1.54 \times 10^{-2}$ $s^{-1}$); and normal alkanes (k'=$1.98 \times 10^{-3}$ $s^{-1}$) were last readily oxidized by ozone. Small amounts of the normal alkanes will likely degraded into alkenes, alcohols, ketones, and esters during 3 hours of ozonation. They observed no substantial change in the percent amount of n- and iso-paraffin carbons, but a noticeable increase in naphthenic carbon (cyclic alkanes). They explained that the formation of such saturated structures could be due to possible condensation reaction catalyzed by Cu metal in metal catalyzed oxidation processes.

Ozonation of Aromatic Factions of Spilt Oil

The bipolar solvent system consists of both non-polar heptane and hydrophilic acetic acid. The heptane component enables high solubility of PAHs and the acetic acid keeps the polar intermediates and by products in solution. The bipolar solvent system maintains effective exposure of all compounds to ozone throughout the course of reaction and prevents the formation of sludge residues. The aromatic factions of spilt oil discussed in this example are polycyclic aromatic hydrocarbons, such as alkylnaphthalenes, alkylphenanthrenes, and alkylbenzenes; and sulfur heterocycles such as alkylbenzothiophines (ABTs), alkyldibenzothiophines (ADBTs), and alkylbenzonaphthothiophines (ABNTs).

Figure 17A:
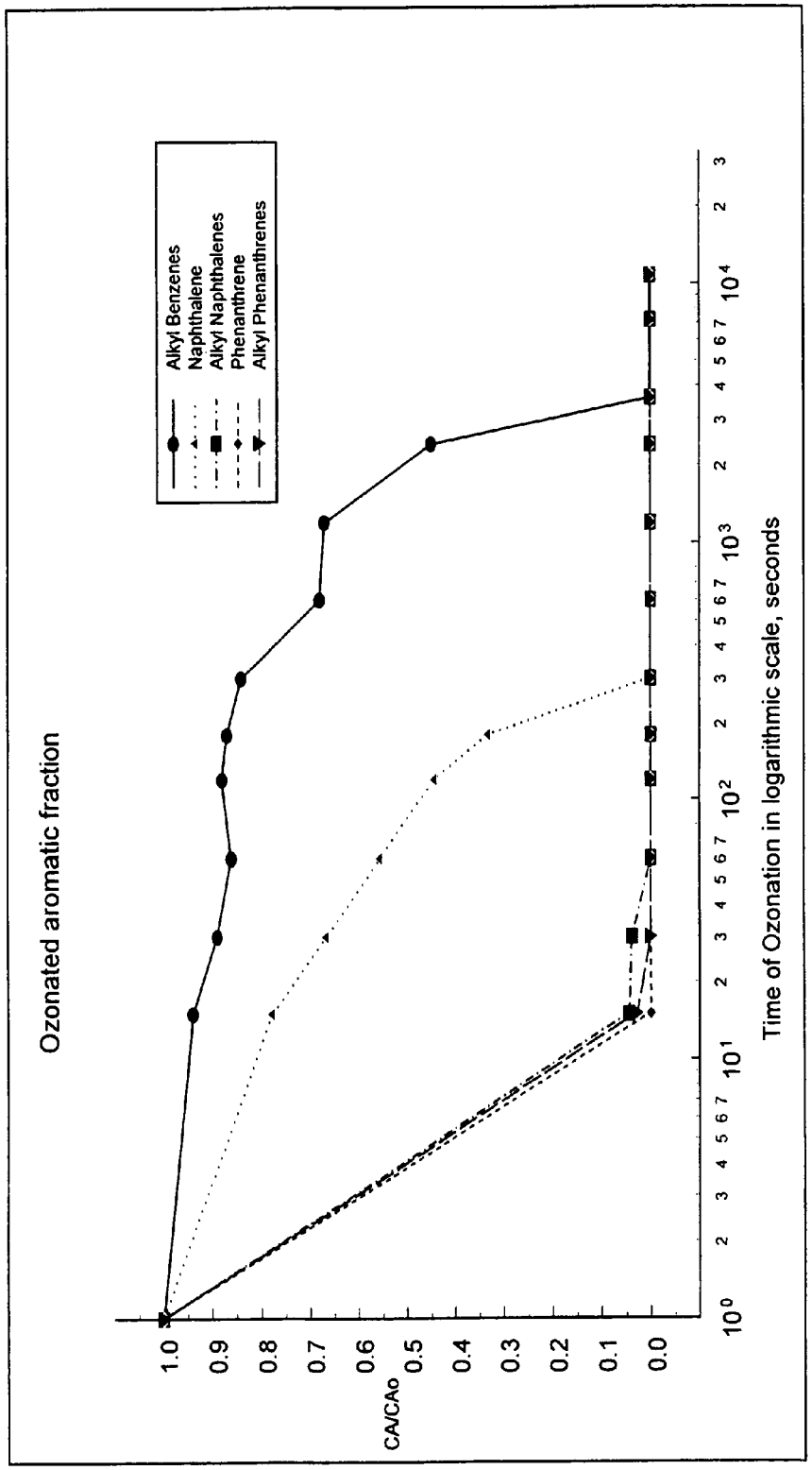
FIGS. 17a and 17b. A graph showing the ozonation results of various aromatic compounds FIG. 18 A graph showing the ozonation results of alkyl benzenes in a bipolar solvent.
Figure 17B:
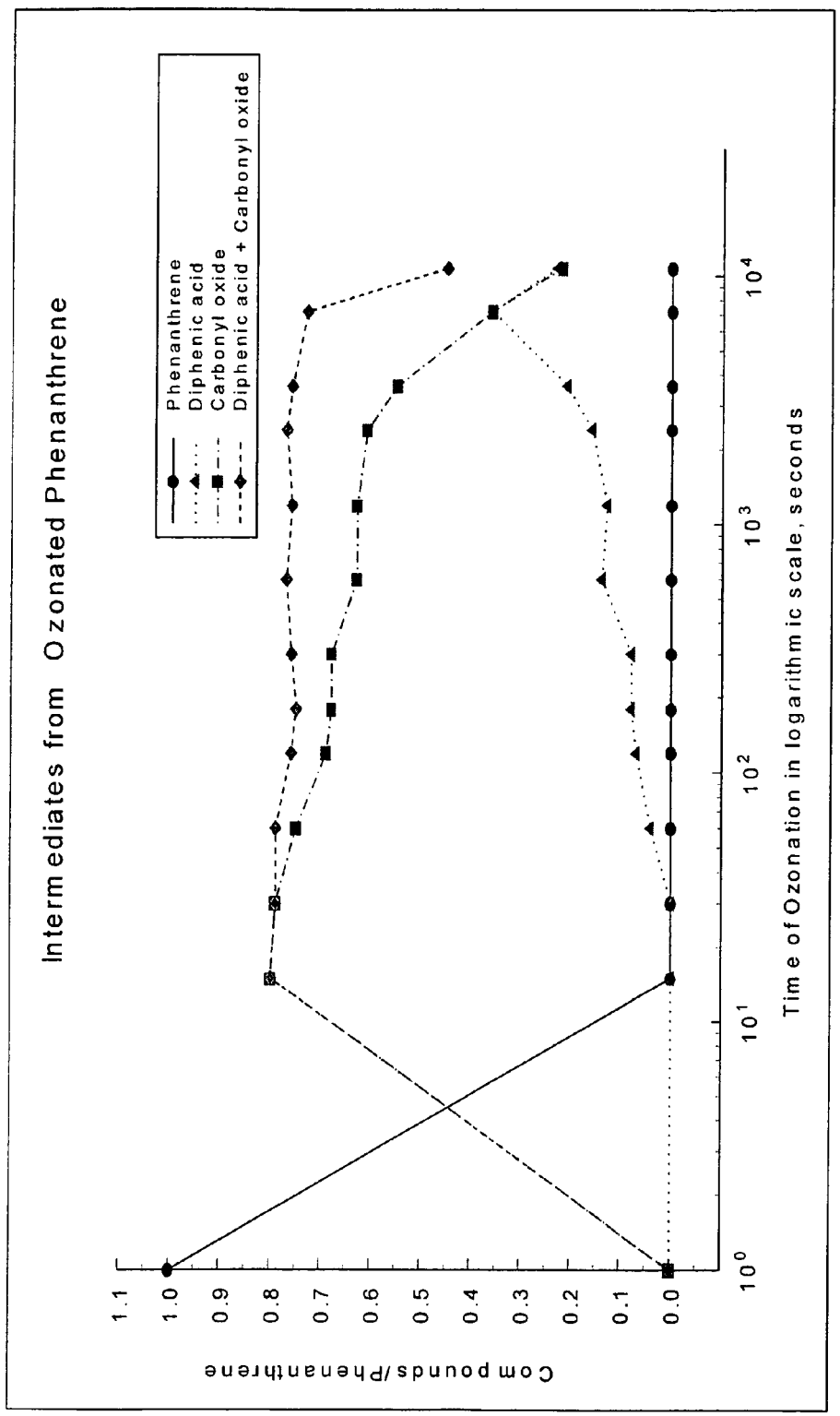

The naphthalenes, alkylnaphthalenes, phenanthrenes, and alkylphenanthrenes ozonated in the bipolar solvent are presented in FIG. 17a. All of the naphthalenes and phenanthrenes destroyed by ozone within 30 seconds. The number of the aromatic rings does affect the rate of reaction of ozone electrophilic attacks. In general, the phenanthrenes with 3 aromatic rings, lower aromaticity, and with higher electron density will likely more reactive with electrophilic ozone than naphthalenes. As shown in Table C-2, phenanthrenes ($k'=1.12\times10^2$ $s^{-1}$) are depleted faster than naphthalenes ($k'=1.11\times10^1$ $s^{-1}$). The ring cleavages of PAHs on the bond and/or atoms with lowest localization energy by ozone molecule in the bipolar solvent has been observed in Examples A and B for pyrene and benzo[a]pyrene. The more hydrophilic intermediates and byproducts, such as aldehydes, ketones, lactones, and carboxylic acids have been generated during the ozonation. Oxygenated biphenyls, one type of the significant intermediates in ozonation of 3 or more rings' aromatics has been observed in the system after the degradation of phenanthrenes as presented in FIG. 17b. Both diphenic acid and carbonyl oxide was primary intermediates from ozonated phenanthrene in the non-participating solvent. The long alkyl chain based alkylbenzenes (less than 2.0% estimated wt %) have also been degraded in the bipolar solvent via ozonation (as see in FIG. 18). The long alkyl chain with 17 to 21 carbons on the alkylbenzenes ($k'=1.75\times10^{-1}$ $s^{-1}$) made them much like normal alkanes being relatively more resistant to ozone than naphthalenes and phenanthrenes.

Table C-2 present the tentative estimated rate of degradation of all the saturate compounds and aromatic compounds in spilt oil during the ozonation in the bipolar solvent system. Naphthalenes, phenanthrenes, benzothiophenes, and benzonaphthothiophenes were very oxidized in the bipolar solvent. Dibenzothiophenes, alkylbenzenes, steranes, and hopanes were substantially stay in solvent in first five minutes, and then degraded rapidly. N-icosane, pristane, and phytane were relatively resistant to ozonation. In this example, both saturated and aromatic hydrocarbons in the oil decreased via ozonation result in the formation of oxygenates (polar compounds). The aldehyde, ketone, lactone, carboxylic acid, alkene, alcohol, ketone, and ester type of intermediates and byproducts have been generated during the ozonation and observed in GC/MS.

Figure 21:
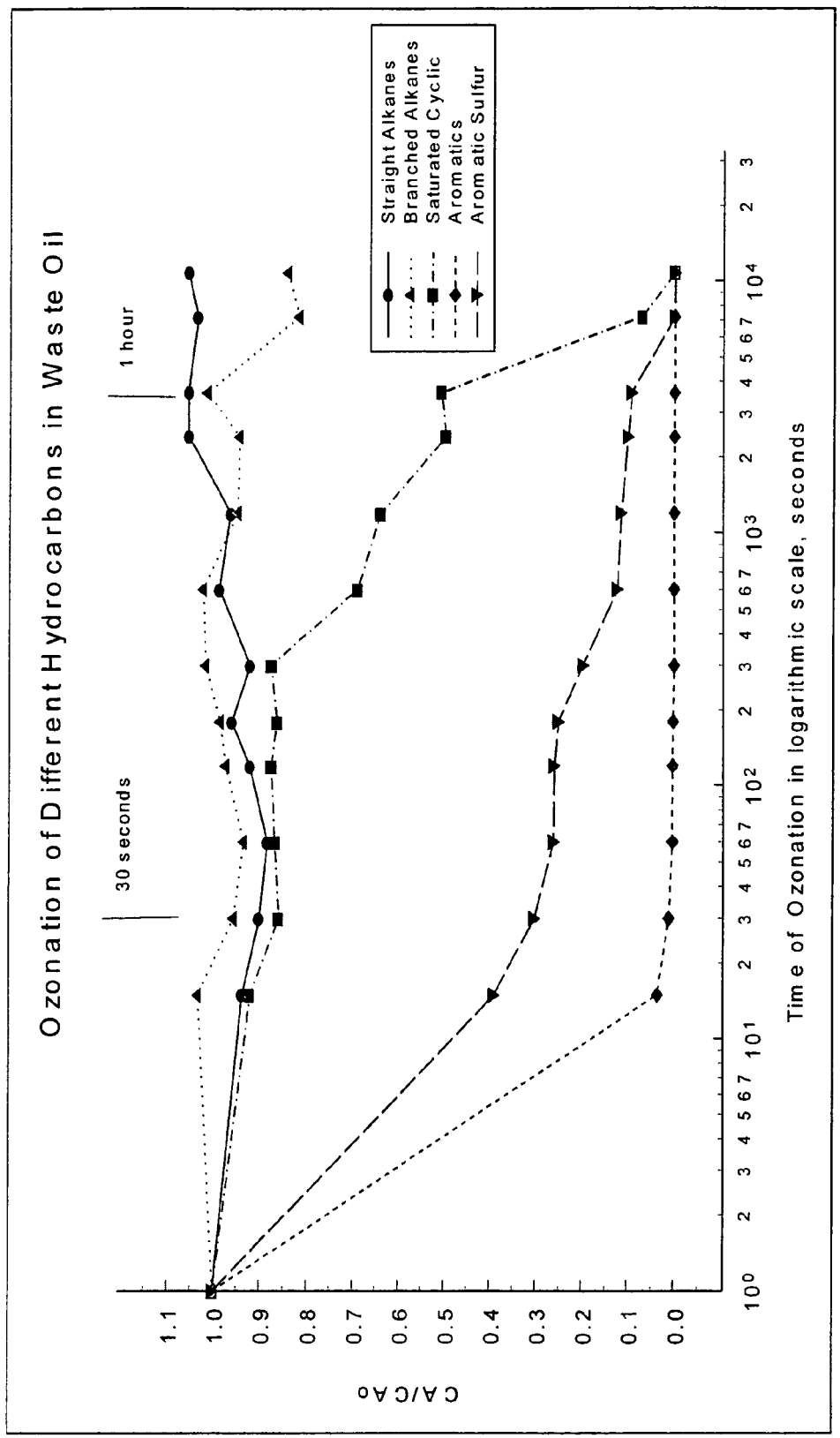
FIG. 21. A graph showing the ozonation results of saturated and unsaturated fractions in waste oil.

These compounds usually are more hydrophilic and mainly sludge precursors in single organic solvent systems. However, all hydrophobic and hydrophilic compounds/intermediates will stay in dissolved form to further ozonation in the bipolar solvent. The results from FIG. 21 and Table C-2 indicated that polycyclic aromatic compounds in the spilt oil undergo more oxidative degradation than saturated compounds. The preferential degradation order of ozonation in the bipolar solvent on the oil constituents was observed as follow: the aromatics (i.e. PAHs and thiophines)>cyclic alkanes (i.e. steranes, terpanes, and hopanes)>branch alkanes (i.e. pristane and phytane)>n-alkanes (i.e. icosane). This result suggested that ozonation as a pretreatment for spilt oils can preferentially eliminate or convert recalcitrant fractions such as aromatics and aromatic sulfur into more bioavailable and water-soluble compounds to be with saturated fraction of oil for subsequent biological degradation.

Ozonation of Aromatic Sulfur Compounds

After carbon and hydrogen, sulfur is typically the third most abundant element in petroleum, ranging from 0.05 to 5% w/w in crude oil. The sulfur-containing compounds in the petroleum are responsible for the air pollution caused by diesel exhaust gas ($SO_x$). Thiophine compounds are also found in some waste streams particularly in wastewater from oil refineries. Condensed thiophines comprise a significant portion of the organosulfur compounds in petroleum. Thiophenes, the model compounds in biodegradation studies, are refractory polycyclic aromatic sulfur compounds present in coal and crude oil. The alkyl-substituted dibenzothiophines were reported as the most recalcitrant to biodegradation within the aromatic fraction of petroleum.

From FIGS. 19a and 19c, the benzothiophines and benzonaphthothiophines were completely eliminated by ozonation in the bipolar solvent systems within 1-minute. However, dibenzothiophenes stay in bipolar solvent for about two hours of ozonation (in FIG. 19b). In the reaction with electrophiles such as ozone under non-participated solvent, attack on carbon of thiophines is the predominant mode of reaction rather than reaction on sulfur. This feature suggested the ozonation of these three sulfur contained compounds will be similar to ozonation of aromatics. The 3 aromatic rings fused benzonaphthothiophenes with less aromaticity, higher frontier electron density, and lower localization energy on atoms and bonds will undergo more rapid reaction with ozone. In comparison with ozonation of benzothiophines and dibenzothiophines, the reaction rates of these were separated by position order of reactivity via electrophiles. The position order of reactivity on benzothiophine was determined to be 3>2>6>5>4>7, which indicated sulfur containing ring are more reactive to electrophiles than benzene. The electrophilic substitutions on dibenzothiophines occur predominantly at the position para- to the sulfur atom such as position −2 and −8, which is mainly on both fused benzenes. Since the benzene rings are less readily attacked by ozone than sulfur-fused rings, benzothiophines with exposed sulfur fused ring undergo much severe oxidation than dibenzothiophines.

Even the catalytic hydrodesulfurization (HDS) method employed in the refining processes has difficulty in the desulfurization of dibenzothiophene and its derivatives among sulfur-containing compounds in the light oil. The ozonated thiophines in non-participating solvent as bipolar solvent likely will form o-hydroxybenzene sulfonic acid, o-sulfobenzoic acid, and homophthalic acid. The mass spectra of ozonated thiophines showed fragments of m/z 60 and 73 corresponding to the underivatized acids.

Figure 18:
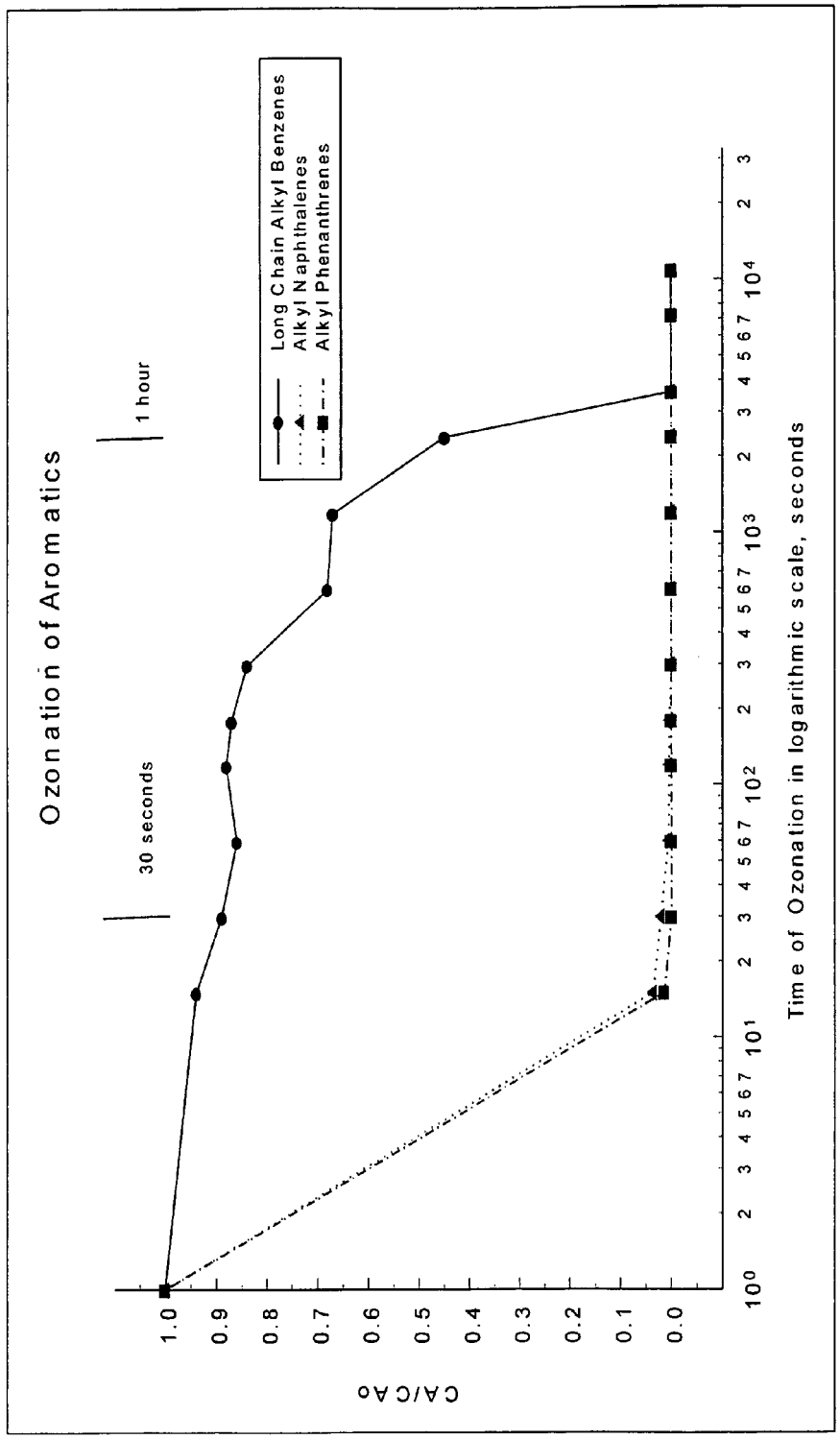
Figure 19:
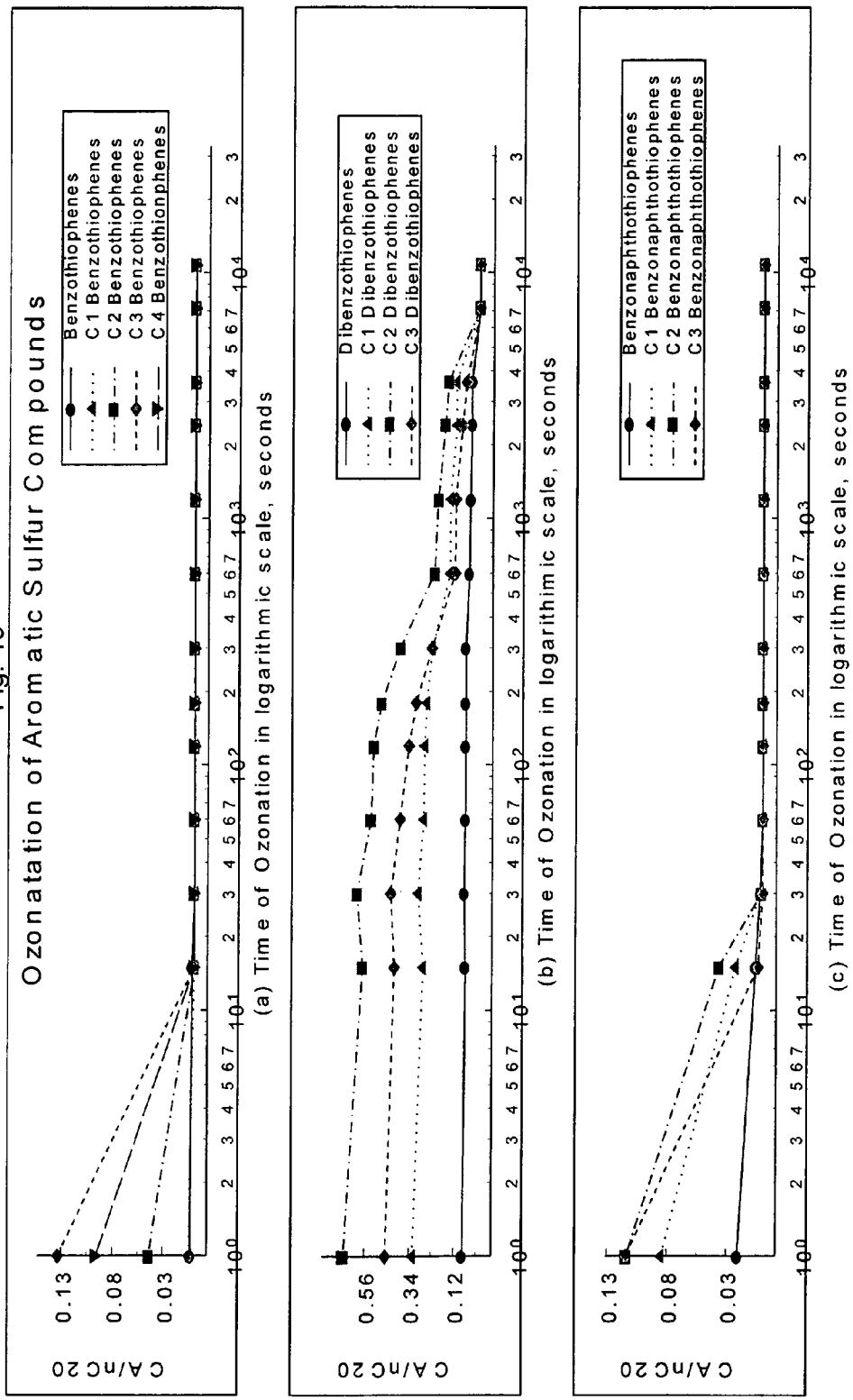
FIG. 19 A graph showing the ozonation results of aromatic sulfur compounds.
Figure 20:
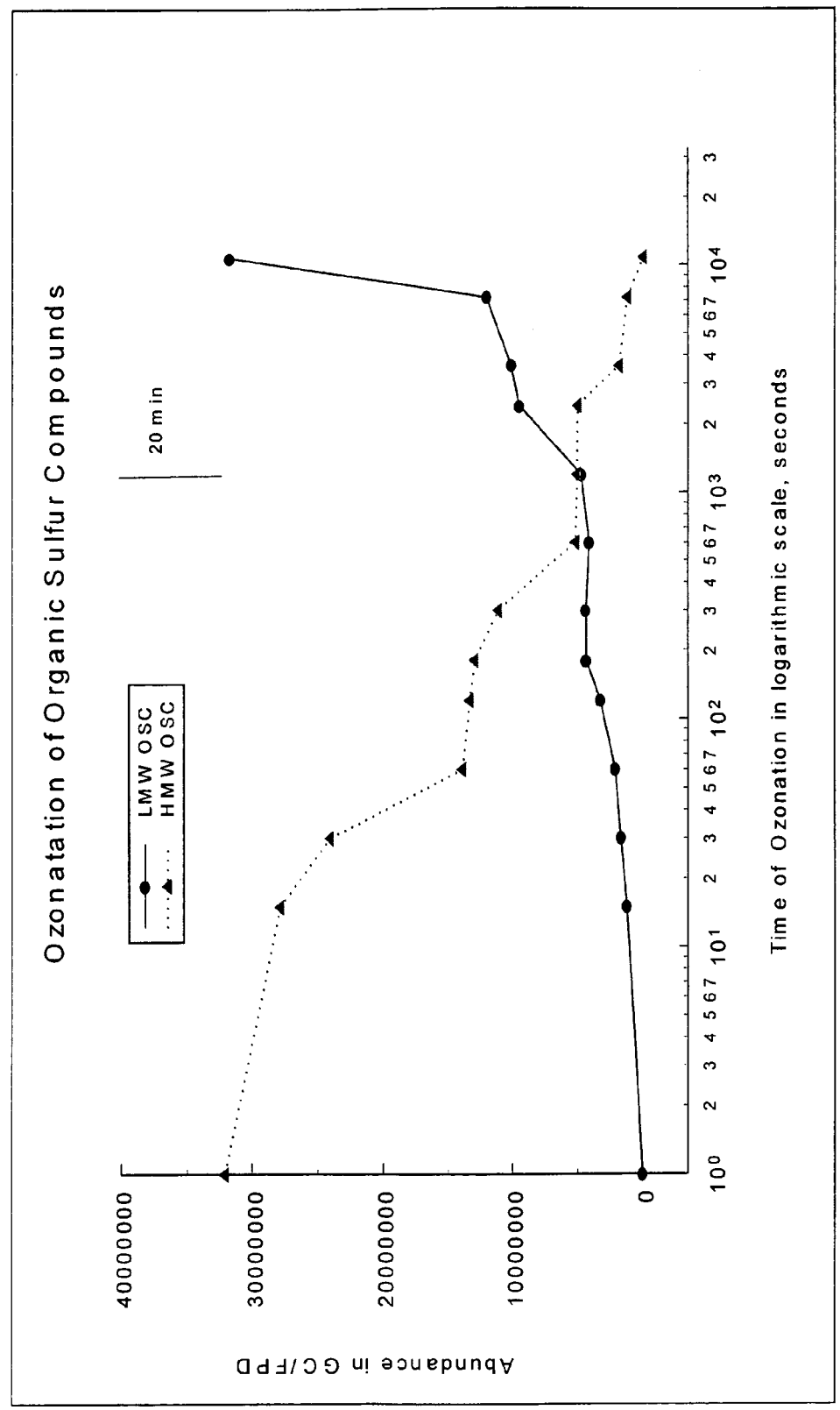
FIG. 20. A graph showing the results of ozonation of high-molecular weight and low molecular weight sulfur compounds.

Bulk characterization of sulfur-containing compounds in GC/FPD can effectively separate the low molecular weight organic sulfur compounds that mainly are organic polysulfides from the high molecular weight organic sulfur compounds that mainly represent high molecular weight resins (more than six condensed-ring aromatics with heteroatoms contents and polar compounds) and asphaltenes (the mixture of polydispersed-condensed polyaromatic units, with heteroatoms contents, bearing alicyclic sites, and substituted and connected with each other via aliphatic chains) besides the alkylated thiophines, dibenzothiophines, and benzonaphthothiophines. FIG. 20 monitored the low molecular weight sulfur compounds cumulated along with ozonation, and the high molecular weight sulfur compounds are gradually decrease with ozonation. This result from FIGS. 18 and 19 showed that the high molecular weight OSC were mineralized into low molecular weight OSC by ozonation in the bipolar solvent.

Biodegradability of Ozonated Oil

Figure 23:
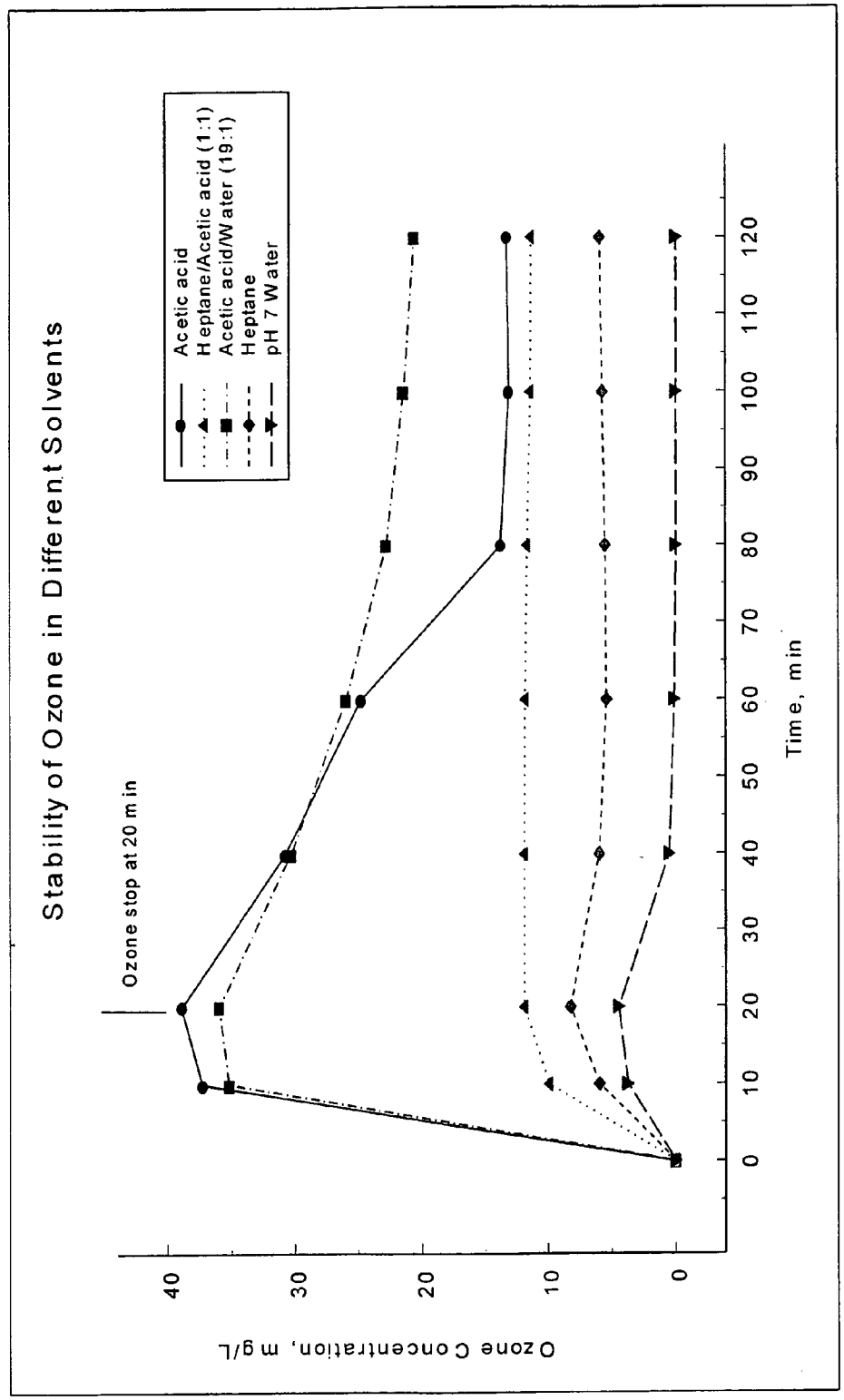
FIG. 23 A graph showing the solubility of ozone in various solvents.

As a potent treatment agent, $O_3$ tends to self-decompose in aqueous environment or react with organic solvents. FIG. 23 compares the solubility and stability of $O_3$ in aqueous and organic solvents of different compositions under the employed experimental conditions and equipment settings. Ozone exhibits higher solubility and stability in the bipolar solvent used in the present example than in water or heptane alone. The stability of the solvent system itself subject to ozonation was tested by conducting ozonation experiments of the solvent system with and without contaminants.

Scenarios of remediation application will likely call for continual ozonation of spilt oil (or other wastes) at higher concentrations, which will more likely result in an abundant formation of intermediates. To assess the level of ozonation pretreatment that would be required to render aromatic compounds in spilt oil and their daughter compounds co-metabolizable, the inhibitory effect of the intermediates from ozonation of spilt oil on biological treatment were studied. After varying duration of ozonation in the bipolar solvent as described previously, the separated 95% acetic acid solutions laden with intermediates were diluted to 5% acetic acid solution and were tested for $E$-coli toxicity as well as $BOD_5$.

Figure 22:
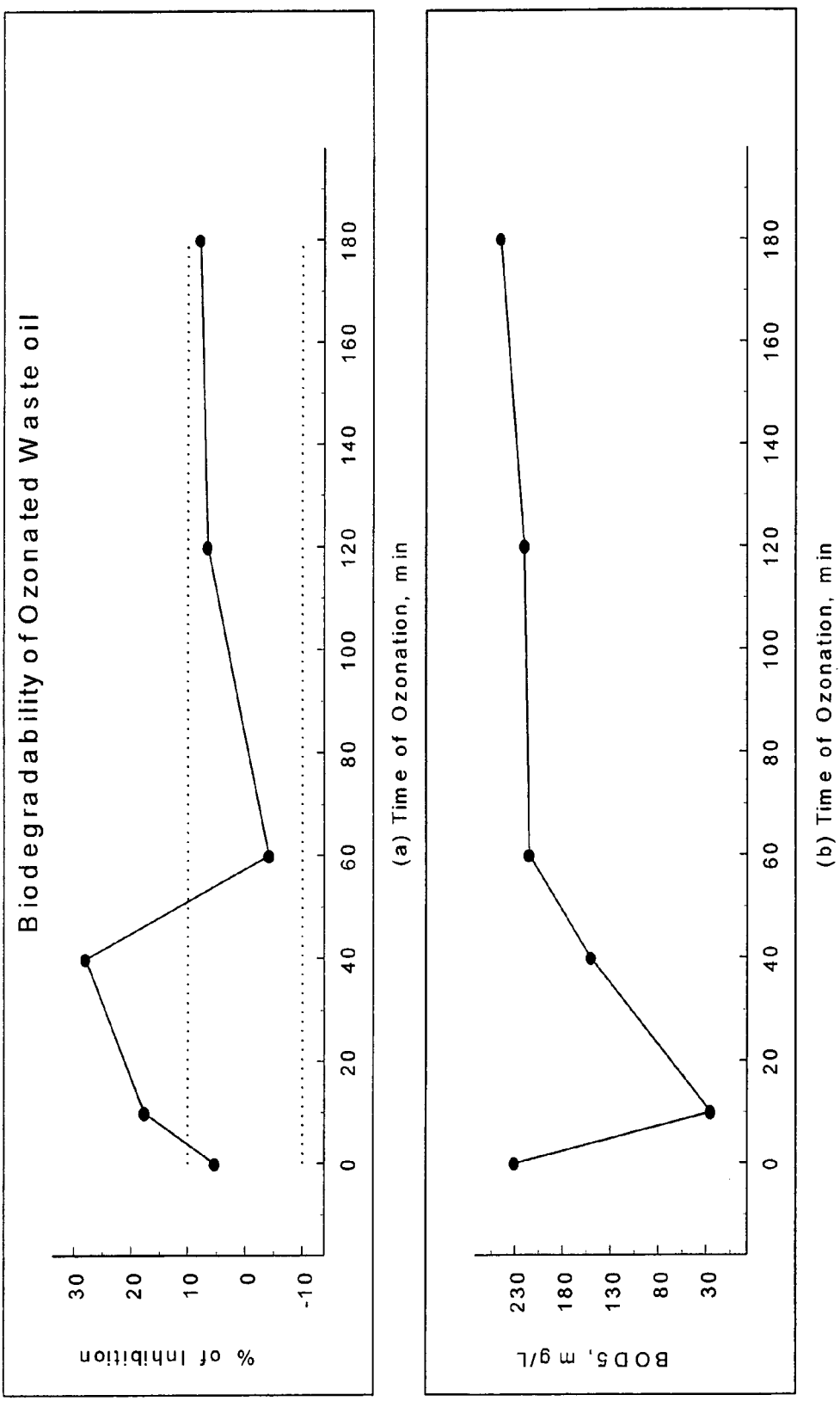
FIGS. 22a and 22b. A graph showing the toxicity and BOD of various fractions according to ozonation duration.

FIG. 22$a$ shows toxicity of the intermediates and FIG. 22$b$ the $BOD_5$ according to ozonation duration. As shown, the $E$-coli toxicity of the intermediates increased from a +5.30% initially to +17.65% after 10-min ozonation then decreased to −4.16% after 60-min ozonation and remained relatively stable and nontoxic thereafter. It should be noted for the $E$-coli test the nontoxic range is within ±10%, and the toxic range outside which. The reason of nontoxic results initially mainly due to hydrophobic nature of spilt oil, which prefer to stay with non-polar heptane and limited compounds from oil dissolved into acetic acid. After ozonation, polar intermediates formed and readily dissolved into acetic acid, which contributed to the toxicity and $BOD_5$.

The $BOD_5$ results show a gradual increase from little registered $BOD_5$ to 245 mg/L throughout the course of ozonation except initial $BOD_5$ with 230 mg/L, whereas theoretical calculation of the ultimate BOD due to acetic acid present in the sample amounts to 320 mg/L. In other words, the 5-day BOD ($BOD_5$) of 230 mg/L measured for the intermediates-laden ozonated sample constituted 72% of the ultimate BOD. This ratio of $BOD_5$ to ultimate BOD is not uncommon for readily biodegradable substances, and it indicates that the degradation of acetic acid has not been inhibited by the presence of the intermediates. The reason of 230 mg/L of initial $BOD_5$ was mostly due to hydrophobic nature of spilt oil, which prefer to stay with non-polar heptane and limited compounds from oil dissolved into acetic acid. In other word, 230 mg/L measured $BOD_5$ were primarily from 5% acetic acid. The 245 mg/L of BOD5 after 3-hours ozonation, 15 mg/L of the $BOD_5$ should be contributed from those polar intermediates.

The toxicity and BOD results are consistent with each other, suggesting that for the initial spilt oil loading of 480 mg/L, 60 min of ozonation in the bipolar system is sufficient to render it nontoxic, co-metabolizable to the $E$-coli bacteria. From a viewpoint of overall process efficiency, the results indicate viability of the bipolar solvent system in incorporating a sequential chemical-biological treatment scheme.

CONCLUSIONS

In this example, the homogeneous phase of the bipolar solvent makes the target compounds constantly susceptible to attack and degradation at the molecular level. All different fractions of constituents in the petroleum were able to react with ozone homogeneously in the bipolar solvent. The preferential degradation order of ozonation in the bipolar solvent on the oil constituents was also observed: the aromatics (i.e. PAHs and thiophines)>cyclic alkanes (i.e. steranes, terpanes, and hopanes)>branch alkanes (i.e. pristane and phytane)>n-alkanes (i.e. icosane). The toxicity and BOD results suggested that for the initial spilt oil loading of 480 mg/L, 60 min of ozonation in the bipolar system is sufficient to render it nontoxic, co-metabolizable to the $E$-coli bacteria. Therefore, the ozonation of spilt oil in the bipolar solvent can eliminate and transform the toxic and recalcitrant aromatic hydrocarbons which will undergo more oxidative degradation than saturated compounds into acetic acid with biodegradable saturated molecules for the subsequent biotreatment or reozonation.

In separate experiments of spilt oil employing heptane as the sole solvent, precipitates occurred shortly after ozonation commenced. Separation of the heptane solution from the solid precipitate and subsequent GC analyses of the solution and the solid revealed only the parent nonpolar compounds remained in solution. While a nonpolar solvent such as heptane dissolves spilt oil and makes it readily susceptible to $O_3$ attack and degradation, the nonpolar solvent fails to retain the polar intermediates in solution, resulting in the formation of a solid precipitate shortly after ozonation begins. Therefore, the use of the bipolar solvent eliminates the occurrence of a solid phase that often becomes the rate-limiting step in the waste treatment sequence. The bipolar solvent system such as the heptane/acetic acid (1:1, v/v) can be useful in tackling recalcitrant compounds such as pyrene, benzo[a]pyrene, and other heavy polycyclic aromatic hydrocarbons. These compounds are recalcitrant partly due to their hydrophobic nature that renders them highly insoluble, thus rendering inaccessible to microbes and even to chemical oxidant such as $O_3$ in the aqueous phase.

The bipolar solvent as described is readily separated into two phases. By adding a small amount of water, the two phases separate allowing the heptane devoid of the contaminant to be reused for another treatment cycle and the acetic acid now laden with biodegradable intermediates (including acetic acid itself) amenable to further biological degradation.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

TABLE A-I

BOD and COD of pyrene solutions
(means ± standard deviations of triplicates).

| Solution | $BOD_5$ (mg/L) | COD (mg/L) | $BOD_5$/COD ratio (#) |
|---|---|---|---|
| Pyrene (saturated, not ozonated) | 0.83 ± 0.15 | 1.0 ± #0.01 | 0.83 |
| Batch (ozonated, 10 min) | 1.75 ± 0.65 | 2.67 ± 1.2 | 0.66 |
| Column effluent (ozonated, composite) | 7.30 ± 0.20 | 13.7 ± 0.76 | 0.53 |

TABLE A-II

Intermediates and products in the ozonated column effluent, as identified by GC/MS.

| Retention Time (min) | Compound | before ozonation | 15-30 min | 30-60 min | 60-90 min | 90-120 min | Rinse 120 min after |
|---|---|---|---|---|---|---|---|
| 14.6 | unknown (m/z 154) (26) | • | • | • | • | • | • |
| 15.3 | unknown (m/z 139)(27) | • | • | • | • | • | • |
| 20.2 | ethanol, 2-[2-butoxyethoxy]- (14) | • | o | o | o | o | o |

TABLE A-II-continued

Intermediates and products in the ozonated column effluent, as identified by GC/MS.

| Retention Time (min) | Compound | before ozonation | Ozonated effluent at interval 15-30 min | 30-60 min | 60-90 min | 90-120 min | Rinse 120 min after |
|---|---|---|---|---|---|---|---|
| 22.5 | phthalic anhydride (7) | • | • | • | • | O | • |
| 23.2 | propanoic acid, 2-methyl-,butyl ester (15) | • | • | • | • | O | • |
| 25.3 | tetradecane (17) | • | • | • | • | O | • |
| 28.1 | pentadecane (18) | • | • | O | O | O | O |
| 28.2 | butylated hydroxytoluene (11) | • | • | O | O | O | • |
| 29.5 | diethyl phthalate (6) | • | O | O | O | O | O |
| 30.7 | hexadecane (19) | • | • | • | O | O | O |
| 33.0 | nonyl phenol (13) | • | • | • | O | O | • |
| 37.6 | 4H-cyclopenta[def]phenanthrene (8) | • | • | • | • | • | • |
| 37.9 | dibutyl phthalate (12) | • | • | • | • | • | • |
| 38.3 | hexadecanoic acid (16) | • | • | • | O | O | • |
| 38.8 | xanthone (10) | O | O | • | • | • | O |
| 41.6 | henicosane (21) | • | • | • | • | • | • |
| 41.7 | pyrene (1) | • | • | • | • | • | • |
| 43.3 | 2,2',6,6'-biphenyltetraaldehyde (3) | O | • | • | • | • | • |
| 43.5 | docosane (22) | • | • | • | • | • | • |
| 45.1 | tricosane (23) | • | • | • | • | • | • |
| 45.3 | Benzylbutyl phthalate (5) | • | • | • | • | • | • |
| 46.8 | 4,5-phenanthrenedialdehyde (2) | O | • | • | • | • | • |
| 46.9 | tetracosane (24) | • | • | • | • | • | • |
| 48.4 | Cyclopenta[def]phenanthrene (9) | • | • | • | • | • | • |
| 48.7 | 1,2-benzenedicarboxylic acid, diisooctyl (4) | • | • | • | • | • | • |
| 48.8 | dibutyl phthalate (12) | • | • | • | • | • | • |
| 48.9 | pentacosane (20) | • | • | • | • | • | • |
| 50.4 | hexacosane (28) | • | • | • | • | • | • |
| 53.6 | 6-propyl tridecane (25) | • | • | • | • | • | • |

• found; O not found

TABLE A-III

Intermediates and products in the ozonated effluent after various degree biotreatment, as identified by GC/MS.

| Retention Time (min) | Compound | Biological Incubation of Ozonated Effluent 0 day | 5 days | 10 days | 15 days | 20 days |
|---|---|---|---|---|---|---|
| 14.6 | unknown(m/z 154 )(26) | • | • | • | • | • |
| 15.3 | unknown(m/z 139) (27) | • | • | • | • | • |
| 20.2 | ethanol, 2-[2-butoxyethoxy]- (14) | O | O | O | O | O |
| 22.5 | phthalic anhydride (7) | • | O | O | O | O |
| 23.3 | propanoic acid, 2-methyl-,butyl ester (15) | • | O | O | O | O |
| 25.3 | tetradecane (17) | • | • | • | • | • |
| 28.1 | pentadecane (18) | O | O | O | O | O |
| 28.2 | butylated hydroxytoluene (11) | • | • | • | • | • |
| 29.5 | diethyl phthalate (6) | O | O | O | O | O |
| 30.7 | hexadecane (19) | • | O | O | O | O |
| 31.0 | phosphoric acid tributyl ester (31) | O | O | O | • | • |
| 33.0 | nonyl phenol (13) | • | O | O | O | O |
| 36.8 | cyclododecane (29) | • | • | • | • | • |
| 37.6 | 4H-cyclopenta[def]phenanthrene (8) | • | O | O | O | O |
| 37.9 | dibutyl phthalate (12) | • | • | • | • | • |
| 38.3 | hexadecanoic acid (16) | • | O | O | O | O |
| 38.8 | xanthone (10) | • | O | O | O | O |
| 41.6 | henicosane (21) | • | O | O | O | O |
| 41.7 | pyrene (1) | • | O | O | O | O |
| 43.0 | biological culture (m/z 226) (30) | • | • | • | • | • |
| 43.3 | 2,2',6,6'-biphenyltetraaldehyde (3) | • | O | O | O | O |
| 43.5 | docosane (22) | • | O | O | O | O |
| 45.1 | tricosane (23) | • | • | • | • | • |
| 45.3 | benzylbutyl phthalate (5) | • | • | • | • | • |
| 46.8 | 4,5-phenanthrenedialdehyde (2) | • | • | • | • | • |
| 46.9 | tetracosane (24) | • | • | • | • | • |
| 48.4 | cyclopenta[def]phenanthrene (9) | • | • | • | • | • |
| 48.7 | 1,2-benzenedicarboxylic acid, diisooctyl (4) | • | • | • | • | • |
| 48.8 | dibutyl phthalate (12) | • | • | • | • | • |
| 48.9 | pentacosane (20) | • | • | • | • | • |

TABLE A-III-continued

Intermediates and products in the ozonated effluent after various degree biotreatment, as identified by GC/MS.

| Retention Time (min) | Compound | Biological Incubation of Ozonated Effluent | | | | |
|---|---|---|---|---|---|---|
| | | 0 day | 5 days | 10 days | 15 days | 20 days |
| 50.4 | hexacosane (28) | • | • | • | • | • |
| 53.6 | 6-propyl tridecane (25) | • | • | • | • | • |

• found; O not found

TABLE A-IV

Mass balance for the pyrene-loaded column before and after ozone treatment (one typical run).

| | Column Initial loading | Column after ozonation | Effluent | Amount reduced column and efflu |
|---|---|---|---|---|
| Pyrene (mg)$^a$ | 147.2 | 74.6 | 1.24 | 147.2 + 1.24 − 74 = 73.8 (50%) |
| 4,5-Phenanthrenedialdehyde (mg)$^a$ | 0 | 0 | 1.43 | |
| 2,2',6,6'-Biphenyltetraaldehyde (mg)$^a$ | 0 | 0 | 1.72 | |
| COD (mg O$_2$)$^b$ | 432 | 280 | 116 | 432 − 116 − 280 = 36 |

$^a$Amounts of substance (mg) in the column as quantified by GC/FID.
$^b$Oxygen demand (mg O$_2$) in the column as determined by COD test.

TABLE B-I

BOD and COD of benzo[a]pyrene solutions (mean ± standard deviation of triplicates).

| Solution | BOD$_5$ (mg/L) | COD (mg/L) | BOD$_5$/COD ratio (#) |
|---|---|---|---|
| Benzo[a]pyrene (saturated, not ozonated) | — | 0.3 ± 0.5 | — |
| Batch (ozonated, 50 min) | — | 12.7 ± 1.5 | — |
| Column effluent (ozonated, composite of 4 h) | 4.2 ± 0.20 | 13.7 ± 0.76 | 0.43 |

Table B-II

Intermediates and products from ozonation of benzo[a]pyrene, as identified by GC/MS.

| Compound | Retention time (min) | m/z | Compound name |
|---|---|---|---|
| 1 | 9.83 | 168 | No ID |
| 2 | 9.89 | 112 | 1-Pentene, 2-isopropyl |
| 3 | 9.95 | 140 | 1-Hexene, 4-methyl, 2-isopropyl |
| 4 | 10.25 | 140 | 1-Pentene, 3,4-dimethyl, 2-propyl |
| 5 | 10.46 | 140 | 1-Pentene, 3,4,4-trim ethy, 2-ethyl |
| 6 | 10.93 | 140 | 1-Pentene, 3,4-methyl, 2-dimethyl |
| 7 | 11.01 | 140 | 1-Hexene, 3,4-dimethyl, 2-ethyl |
| 8 | 11.10 | 140 | No ID |
| 9 | 11.21 | 140 | 1-Hexene, 4,5-dimethyl, 2-ethyl |
| 10 | 11.27 | 140 | 1-Hexene, 4,5-dimethyl, 2-ethyl |
| 11 | 11.33 | 140 | 1-Pentene,3-methyl, 2-isobutyl |
| 12 | 11.80 | 140 | 1-Hexene, 4,5-dimethyl, 2-ethyl |
| 13 | 11.88 | 140 | 2-Hexene, 2,3,4,5-tetramethyl |
| 14 | 12.02 | 140 | 1-Hexene, 4,5-dimethyl, 3-ethyl |
| 15 | 12.51 | 154 | No ID |
| 16 | 13.37 | 154 | 3-Octene, 5-methyl, 3-ethyl |
| 17 | 13.98 | 154 | 3-Nonene, 6,8-dimethyl |
| 18 | 14.17 | 154 | 1-Hexene, 3,5-dimethyl, 2-iospropyl |
| 19 | 14.34 | 154 | 3-Nonene, 6,8-dimethyl |
| 20 | 14.96 | 154 | 13-octane, 25,7-trimethyl |
| 21 | 15.48 | 154 | 3-Decene, 9-methyl |
| 22 | 15.66 | 139 | Butanoic vinyl anhydride |
| 23 | 16.50 | 123 | No ID |
| 24 | 17.05 | 334 | Decafluorobiphenyl (Internal standard) |
| 25 | 17.42 | 182 | No ID |
| 26 | 24.16 | 429 | No ID |
| 27 | 36.81 | 242 | 3-methylchrysene |
| 28 | 37.60 | 272 | 7-methyl-8-propanalpyrene |
| 29 | 38.42 | 149 | Phthalic anhydride |
| 30 | 38.70 | 272 | 4-Methyl-5-methanal-chrysene |
| 31 | 45.66 | 127 | Pentadecane (C15) |
| 32 | 47.38 | 149 | Benzoic acid, ethyl ester |
| 33 | 47.75 | 163 | Benzoic acid, propyl ester |
| 34 | 47.92 | 141 | Tridecane (C16) |
| 35 | 49.04 | 163 | Bis (2-ethylhexyl) phthalate |
| 36 | 49.27 | 293 | 1,2-Benzenedicarboxylic acid, diisononyl ester |
| 37 | 52.16 | 293 | 1,2-Benzenedicarboxylic acid, diisononyl ester |
| 38 | 52.21 | 293 | 1,2-Benzenedicarboxylic acid, diisononyl ester |
| 39 | 52.37 | 293 | 1,2-Benzenedicarboxylic acid, diisononyl ester |
| 40 | 52.48 | 293 | 1,2-Benzenedicarboxylic acid, diisononyl ester |
| 41 | 52.57 | 293 | 1,2-Benzenedicarboxylic acid, diisononyl ester |
| 42 | 52.68 | 293 | 1,2-Benzenedicarboxylic acid, diisononyl ester |
| 43 | 52.78 | 293 | 1,2-Benzenedicarboxylic acid, diisononyl ester |
| 44 | 52.92 | 293 | 1,2-Benzenedicarboxylic acid, diisononyl ester |
| 45 | 53.10 | 293 | 1,2-Benzenedicarboxylic acid, diisononyl ester |
| 46 | 53.20 | 293 | 1,2-Benzenedicarboxylic acid, diisononyl ester |
| 47 | 53.25 | 293 | 1,2-Benzenedicarboxylic acid, diisononyl ester |
| 48 | 53.51 | 293 | 1,2-Benzenedicarboxylic acid, diisononyl ester |
| 49 | 53.65 | 293 | 1,2-Benzenedicarboxylic acid, diisononyl ester |
| 50 | 53.72 | 267 | 1,2-Benzenedicarboxylic acid, diisononyl ester |

Table B-II-continued

Intermediates and products from ozonation of benzo[a]pyrene, as identified by GC/MS.

| Compound | Retention time (min) | m/z | Compound name |
|---|---|---|---|
| 51 | 53.90 | 293 | 1,2-Benzenedicarboxylic acid, diisononyl ester |
| 52 | 54.00 | 293 | 1,2-Benzenedicarboxylic acid, diisononyl ester |
| 53 | 54.12 | 293 | 1,2-Benzenedicarboxylic acid, diisononyl ester |
| 54 | 54.42 | 293 | 1,2-Benzenedicarboxylic acid, diisononyl ester |
| 55 | 54.73 | 293 | 1,2-Benzenedicarboxylic acid, diisononyl ester |
| 56 | 55.21 | 293 | 1,2-Benzenedicarboxylic acid, diisononyl ester |
| 57 | 55.74 | 293 | 1,2-Benzenedicarboxylic acid, diisononyl ester |
| 58 | 57.82 | 197 | Octadecane (C18) |
| 59 | 60.19 | 197 | Octadecane, methyl (C19) |
| 60 | 62.98 | 197 | nonadecane (C19) |
| 61 | 66.30 | 197 | henelcosane (C21) |

TABLE B-III

Mass balance for the benzo[a]pyrene-loaded column before and after ozone treatment (one typical run).

| | Column from Initial loading column and reduced | Column effluent | Effluent After ozonation | Amount |
|---|---|---|---|---|
| Benzo[a]pyrene (mg)[a] (22.0 %) | 150 | 117 | 0.0 | 150 − 11 = 33.0 |
| COD (mg $O_2$)[b] | 436 | 340 | 78.0 | 436 − 78 = 36.0 |
| | 340 | | | |

[a]Amounts of substance (mg) in the column as quantified by GC/FID.
[b]Oxygen demand (mg $O_2$) in the column as determined by COD test.

TABLE C-1

Represent compounds and their structures

| Type | Represent Compounds | Represent Structure |
|---|---|---|
| I | Icosane | $H_3C-(CH_2)_{18}-CH_3$ |
| II | Pristane | (structure) |
| | Phytane | (structure) |
| III | Steranes | (structure), $R = C_1, C_2, C_3$ |
| | Tetracydic Terpane | (structure) |

TABLE C-1-continued

Represent compounds and their structures

| Type | Represent Compounds | Represent Structure | |
|---|---|---|---|
| | Pentacyclic Terpanes | 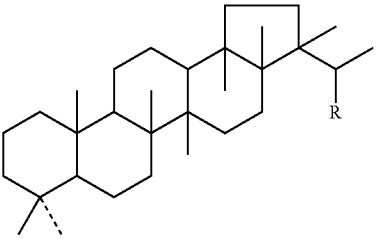 | R = C₁, C₂, C₃ |
| IV | Alkyl Benzenes[d] |  | R = C₁₇ to C₂₁; R' = C₀, C₁ |
| | Naphthalenes |  | R = C₀, C₁, C₂, C₃ |
| | Phenanthrenes | 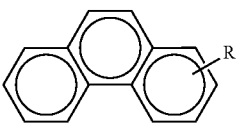 | R = C₀, C₁, C₂, C₃ |
| V | Benzothiophenes | 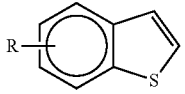 | R = C₀, C₁, C₂, C₃, C₄ |
| | Dibenzothiophenes | 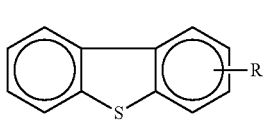 | R = C₀, C₁, C₂, C₃ |
| | Benzonaphthothiophenes | 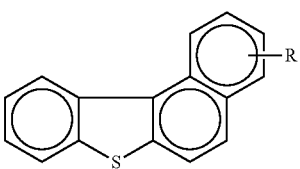 | R = C₀, C₁, C₂, C₃ |

Alkyl group : R = $C_nH_{2n+1}$

TABLE C-2

Tentative estimated pseudo-first-order rate constants under ozonated bipolar system

| Compounds | $k^1$ (s$^{-1}$) |
|---|---|
| nC20 | 1.98E−03 |
| Pristane | 1.30E−02 |
| Phytane | 1.78E−02 |
| Sum of Steranes | 4.94E+01 |
| Sum of Hopanes | 1.20E−01 |
| Sum of Alkyl Benzenes | 1.75E−01 |
| Sum of Naphthalenes | 1.08E+02 |
| Sum of Phenanthrenes | 1.12E+02 |
| Sum of Benzothiophines | 1.57E+02 |
| Sum of Dibenzothlophines | 1.96E−01 |
| Sum of Benzonaphthothiophines | 6.72E+01 |
| Straight Chain (Type I) | 1.98E−03 |
| Brainched Chain (Type II) | 1.54E−02 |
| Saturated Cydics (Type III) | 2.57E−01 |
| Aromatics (Type IV)[#] | 1.10E+02 |
| Aromatic Sulfur (Type V) | 6.82E+01 |

[#]Excluding long chain alkyl benzenes

What is claimed is:

1. A method for providing degradation of polycyclic aromatic hydrocarbon compounds, the method comprising:
providing a bipolar solvent comprising a non-polar solvent, which is immiscible with water and of a sufficiently non-polar character to dissolve the polycyclic aromatic hydrocarbon compounds, and a polar-solvent, which is soluble with water and fully miscible with the non-polar solvent to form a single phase with the non-polar solvent;

dissolving an amount of ozone in the bipolar solvent;

dissolving the polycyclic aromatic hydrocarbon compounds by contacting the bipolar solvent containing the dissolved ozone with the polycyclic aromatic hydrocarbon compounds, the duration of the contacting and concentration of the ozone is sufficient to react the dissolved polycyclic aromatic hydrocarbon compounds with the ozone to form oxygenated intermediates;

adding a first amount of water to the bipolar solvent after contacting the bipolar solvent containing the dissolved ozone with the polycyclic aromatic hydrocarbon compounds and mixing the bipolar solvent and the first amount of water to form two phases, a non-polar phase and a polar phase, the non-polar phase comprising the non-polar solvent, the polar phase comprising the polar solvent and the oxygenated intermediates; and exposing the polar phase to microbes and diluting the polar phase with a second amount of water to allow the microbes to metabolize and biodegrade the oxygenated intermediates in the diluted polar phase.

2. A method as in claim 1, wherein the exposing of the polar phase containing the oxygenated intermediates is for a sufficient duration to essentially mineralize the oxygenated intermediates.

3. A method as in claim 1, wherein the bipolar solvent is contacted with the polycyclic aromatic hydrocarbon compounds to react with the dissolved ozone when the polycyclic aromatic hydrocarbon compounds are in a solid form.

4. A method as in claim 1, wherein the bipolar solvent is contacted with the polycyclic aromatic hydrocarbon compounds to react with the dissolved ozone when the polycyclic aromatic hydrocarbon compounds are in solution in the bipolar solvent.

5. A method as in claim 1, wherein the non-polar solvent comprises hydrocarbon with at least 7 carbon atoms.

6. A method as in claim 1, wherein the polar solvent comprises an organic acid.

7. A method as in claim 1, wherein the bipolar solvent comprises heptane and acetic acid.

8. A method for the degradation of polycyclic aromatic hydrocarbon compounds, the method comprising:

dissolving the polycyclic aromatic hydrocarbon compounds by contacting a bipolar solvent containing dissolved ozone with the polycyclic aromatic hydrocarbon compounds, the duration of the contacting and concentration of the dissolved ozone being sufficient to react the dissolved polycyclic aromatic hydrocarbon compounds with the ozone to form oxygenated intermediates, the bipolar solvent comprising a non-polar solvent, which is immiscible with water and of sufficiently non-polar character to dissolve the polycyclic aromatic hydrocarbon compounds, and a polar-solvent, which is soluble with water and fully miscible with the non-polar solvent to form a single phase with the non-polar solvent;

adding about 5% of water to the bipolar solvent after contacting the bipolar solvent containing the dissolved ozone with the polycyclic aromatic hydrocarbon compounds and mixing the bipolar solvent and the water to form two phases, a non-polar phase and a polar phase, the non-polar phase comprising the non-polar solvent, and the polar phase comprising the polar solvent and the oxygenated intermediates;

exposing the polar phase to microbes and diluting the polar phase with an effective amount of water, which is sufficient to allow the microbes to metabolize and biodegrade the oxygenated intermediates in the diluted polar phase.

9. A method as in claim 8, wherein the exposing of the polar phase containing the oxygenated intermediates is for a sufficient duration to essentially mineralize the oxygenated intermediates.

10. A method as in claim 8, wherein the dissolved ozone is reacted with the polycyclic aromatic hydrocarbon compounds when the polycyclic aromatic hydrocarbon compounds are in a solid form.

11. A method as in claim 8, wherein the dissolved ozone is reacted with the polycyclic aromatic hydrocarbon compounds when the polycyclic aromatic hydrocarbon compounds are in solution.

12. A method as in claim 8, wherein the non-polar solvent comprise a hydrocarbon with at least 7 carbon atoms.

13. A method as in claim 8, wherein the polar solvent comprises an organic acid.

14. A method as in claim 8, wherein the bipolar solvent comprises hexane and acetic acid.

15. A method for degradation of polycyclic aromatic hydrocarbon compounds comprising:

contacting the polycyclic aromatic hydrocarbon compounds with ozone dissolved in a bi-polar solvent, the bi-polar solvent comprising a non-polar solvent, which is immiscible with water, and a polar solvent, which is fully miscible with the non-polar solvent forming a single phase with the non-polar solvent, the bi-polar solvent having solubility to polycyclic aromatic hydrocarbon compounds that are insoluble in water, to oxygenated intermediates, to reaction products of polycyclic aromatic hydrocarbon compounds, and to ozone, the contacting being carried out for a sufficient duration to solubilize and react the polycyclic aromatic hydrocarbon compounds with the dissolved ozone to form oxygenated intermediates in the bipolar solvent in the single phase; and after contacting the polycyclic aromatic hydrocarbon compounds with ozone dissolved in the bipolar solvent, subsequently adding a sufficient amount of water to the single phase of the bipolar solvent and mixing the bipolar solvent with the water to form two phases, a non-polar phase comprising the non-polar solvent and a polar phase containing the polar solvent and the oxygenated intermediates.

16. A method as in claim 15, additionally comprising separating the polar phase from the non-polar phase exposing the polar phase to microbes and, diluting the polar phase with water in an amount to allow microbe growth, and incubating the polar phase in the presence of the microbes to biodegrade the oxygenated intermediates in the polar phase.

17. A method as in claim 16, wherein the polar phase is biodegraded for a sufficient duration to essentially mineralize the oxygenated intermediates.

18. A method as in claim 15, wherein the non-polar solvent comprise a hydrocarbon with at least 7 carbon atoms.

* * * * *